US010307477B2

(12) United States Patent
Tomaka et al.

(10) Patent No.: US 10,307,477 B2
(45) Date of Patent: Jun. 4, 2019

(54) METHODS FOR INDUCING AN IMMUNE RESPONSE AGAINST HUMAN IMMUNODEFICIENCY VIRUS INFECTION IN SUBJECTS UNDERGOING ANTIRETROVIRAL TREATMENT

(71) Applicants: Janssen Vaccines & Prevention B.V., Leiden (NL); Beth Israel Deaconess Medical Center, Inc., Boston, MA (US); Henry M. Jackson Foundation for the Advancement of Military Medicine, Inc, Bethesda, MD (US); THE UNITED STATES OF AMERICA, AS REPRESENTED BY THE SECRETARY OF THE ARMY, Fort Datrick, MD (US)

(72) Inventors: Frank Tomaka, Titusville, NJ (US); Maria Grazia Pau, Leiden (NL); Johanna Schuitemaker, Amstelveen (NL); Dan Barouch, Newton, MA (US); Jintanat Ananworanich, Rockville, MD (US); Merlin Robb, Silver Spring, MD (US); Nelson L. Michael, Silver Spring, MD (US); Jerome Kim, Silver Spring, MD (US)

(73) Assignees: Janssen Vaccines & Prevention B.V., Leiden (NL); The Henry M. Jackson Foundation for the Advancement of Military Medicine, Inc., Bethesda, MD (US); Beth Israel Deaconess Medical Center, Inc., Boston, MA (US); The United States of America, as represented by The Secretary Of The Army, Washington, DC (US)

( * ) Notice: Subject to any disclaimer, the term of this patent is extended or adjusted under 35 U.S.C. 154(b) by 0 days.

(21) Appl. No.: 15/693,650

(22) Filed: Sep. 1, 2017

(65) Prior Publication Data

US 2018/0064803 A1 Mar. 8, 2018

Related U.S. Application Data

(60) Provisional application No. 62/383,140, filed on Sep. 2, 2016.

(51) Int. Cl.
*A61K 39/00* (2006.01)
*A61K 39/21* (2006.01)
*C07K 14/005* (2006.01)
*A61K 39/12* (2006.01)
*C12N 7/00* (2006.01)
*A61P 31/18* (2006.01)

(52) U.S. Cl.
CPC .............. *A61K 39/21* (2013.01); *A61K 39/12* (2013.01); *A61P 31/18* (2018.01); *C12N 7/00* (2013.01); *A61K 2039/5256* (2013.01); *A61K 2039/545* (2013.01); *A61K 2039/57* (2013.01); *A61K 2039/575* (2013.01); *A61K 2039/70* (2013.01); *C12N 2710/10043* (2013.01); *C12N 2710/10343* (2013.01); *C12N 2710/24043* (2013.01); *C12N 2710/24143* (2013.01); *C12N 2740/16021* (2013.01); *C12N 2740/16034* (2013.01); *C12N 2740/16134* (2013.01); *C12N 2740/16171* (2013.01); *C12N 2740/16234* (2013.01); *C12N 2740/16271* (2013.01)

(58) Field of Classification Search
CPC .... A61K 39/21; A61K 2039/53; A61K 39/12; C07K 14/005; C12N 2740/16134
See application file for complete search history.

(56) References Cited

U.S. PATENT DOCUMENTS

| | | | |
|---|---|---|---|
| 4,603,112 A | 7/1986 | Paoletti et al. |
| 5,185,146 A | 2/1993 | Altenburger |
| 5,639,649 A | 6/1997 | Almond et al. |
| 5,643,576 A | 7/1997 | Johnston et al. |
| 6,761,893 B2 | 7/2004 | Chaplin et al. |
| 6,911,205 B2 | 6/2005 | Sodroski et al. |
| 7,592,014 B2 | 9/2009 | Binley et al. |
| 7,901,690 B2 | 3/2011 | Lu et al. |
| 7,939,083 B2 | 5/2011 | Dey et al. |
| 8,197,825 B2 | 6/2012 | Sutter et al. |
| 9,017,691 B2 | 4/2015 | Barouch et al. |

(Continued)

FOREIGN PATENT DOCUMENTS

| CN | 102282175 A | 12/2011 |
|---|---|---|
| WO | 0119958 | 3/2001 |

(Continued)

OTHER PUBLICATIONS

Achenbach et al., "Effect of therapeutic intensification followed by HIV DNA prime and rAd5 boost vaccination on HIV-specific immunity and HIV reservoir (EraMune 02): a multicentre randimised clinical trial", 2015, TheLancet, vol. 2:e82-e91.*
Johannes et al., "HIV-1-Specific antibody response and function after DNA Prima nd Recombinant Adenovirus 5 boost HIV Vaccine in HIV-infected subjects", PloS ONE, 2016, 11(8):pdf pp. 1-17.*
Int'l Search Report and Written Opinion dated Apr. 23, 2010 in Int'l Application No. PCT/US2009/060494.
Int'l Search Report dated Mar. 5, 2010 in Int'l Application No. PCT/US2009/064999.

(Continued)

*Primary Examiner* — Barry A Chestnut
(74) *Attorney, Agent, or Firm* — Panitch Schwarze Belisario & Nadel LLP

(57) ABSTRACT

Methods for inducing an immune response against Human Immunodeficiency Virus (HIV) in HIV-infected subjects undergoing antiretroviral therapy (ART) are described. The methods include administering an adenovirus vector primer vaccine and a modified vaccinia virus (MVA) vector booster vaccine encoding mosaic HIV antigens.

20 Claims, No Drawings
Specification includes a Sequence Listing.

(56) References Cited

U.S. PATENT DOCUMENTS

| | | |
|---|---|---|
| 2003/0206926 A1 | 11/2003 | Chaplin et al. |
| 2003/0207287 A1 | 11/2003 | Short |
| 2006/0159699 A1 | 7/2006 | Howley et al. |
| 2007/0166784 A1 | 7/2007 | Barnett et al. |
| 2007/0298051 A1 | 12/2007 | Barouch et al. |
| 2008/0199939 A1 | 8/2008 | Havenga et al. |
| 2008/0279879 A1 | 11/2008 | Zolla-Pazner |
| 2011/0159036 A1 | 6/2011 | Moss et al. |
| 2011/0250220 A1 | 10/2011 | Dey et al. |
| 2012/0045472 A1 | 2/2012 | Harrison et al. |
| 2012/0076812 A1 | 3/2012 | Barouch et al. |
| 2013/0189754 A1 | 7/2013 | Parks et al. |
| 2014/0302080 A1 | 10/2014 | Barouch et al. |
| 2014/0348791 A1 | 11/2014 | Barouch et al. |
| 2015/0291935 A1 | 10/2015 | Barouch et al. |
| 2016/0024156 A1 | 1/2016 | Barouch et al. |
| 2016/0122392 A1 | 5/2016 | Baker et al. |
| 2017/0165355 A1 | 6/2017 | Langedijk |
| 2017/0362280 A1 | 12/2017 | Nguyen et al. |
| 2018/0064803 A1 | 3/2018 | Tomaka et al. |
| 2018/0072777 A1 | 3/2018 | Rutten et al. |

FOREIGN PATENT DOCUMENTS

| | | |
|---|---|---|
| WO | 200242480 A2 | 5/2002 |
| WO | 2003048184 A2 | 6/2003 |
| WO | 2003/104467 A1 | 12/2003 |
| WO | 2004/0044155 | 5/2004 |
| WO | 2006002079 | 1/2006 |
| WO | 2006020071 | 2/2006 |
| WO | 2006/040330 | 4/2006 |
| WO | 2007005934 | 1/2007 |
| WO | 2007/024941 A2 | 3/2007 |
| WO | 2007/104792 A2 | 9/2007 |
| WO | 2007/149491 | 12/2007 |
| WO | 2008063331 | 5/2008 |
| WO | 2008107370 A1 | 9/2008 |
| WO | 2010/042942 A2 | 4/2010 |
| WO | 2010/059732 A1 | 5/2010 |
| WO | 2010096561 A1 | 8/2010 |
| WO | 2011/082087 A2 | 7/2011 |
| WO | 2011/092029 A1 | 8/2011 |
| WO | 2012/030904 | 3/2012 |
| WO | 2013055908 | 4/2013 |
| WO | 2014/047261 | 3/2014 |
| WO | 2014107744 A1 | 7/2014 |
| WO | 2014/124301 A1 | 8/2014 |
| WO | 2015/048770 | 4/2015 |
| WO | 2016037154 A1 | 3/2016 |
| WO | 2016049287 A1 | 3/2016 |
| WO | WO2016049287 * | 3/2016 |
| WO | 2017102929 A1 | 6/2017 |

OTHER PUBLICATIONS

Int'l Search Report dated Mar. 21, 2014 in Int'l Application No. PCT/US2014/010543.
International Search Report and Written Opinion dated Sep. 13, 2017 in Intl Application No. PCT/EP2017/064665.
Janes et al., "MRKAd5 HIV-1 Gag/Pol/Nef Vaccine-Induced T-cell Responses Inadequately Predict Distance of Breakthrough HIV-1 Sequences to the Vaccine or Viral Load", PLoS One, vol. 7, No. 8, pp. e43396 (2012).
Jeffs et al, "Expression and Characterization of Recombinant Oligomeric Envelope Glycoproteins Derived From Primary Isolates of HIV-1," Vaccine, vol. 22, No. 8, pp. 1032-1046 (2004).
Jin et al., "Stabilizing Formulations for Inhalable Powders of an Adenovirus 35-Vectored Tuberculosis (TB) Vaccine (AERAS-402)", Vaccine, vol. 28, No. 27, pp. 4369-4375 (2010).
Julien et al, "Asymmetric Recognition of the HIV-1 Trimer by Broadly Neutralizing Antibody PG9," Proceedings of the National Academy of Sciences of the United States of America, vol. 110, No. 11, pp. 4351-4356 (Mar. 12, 2013).
Julien et al, "Broadly Neutralizing Antibody PGT121 Allosterically Modulates CD4 Binding via Recognition of the HIV-1 gp120 V3 Base and Multiple Surrounding Glycans," PLOS Pathogens, vol. 9, No. 5, pp. e1003342 (May 2013).
Julien et al, "Design and Structure of Two HIV-1 Clade C SOSIP. 664 Trimers That Increase the Arsenal of Native-Like Env Immunogens," PNAS, vol. 112, No. 38, pp. 11947-11952 (2015).
Kamerzell et al., "Protein-Excipient Interactions: Mechanisms and Biophysical Characterization Applied to Protein Formulation Development", Advanced Drug Delivery Review, vol. 63, pp. 1118-1159 (2011).
Kang et al, "Structural and Immunogenicity Studies of a Cleaved, Stabilized Envelope Trimer Derived from Subtype A HIV-1," Vaccine, vol. 27, pp. 5120-5132 (2009).
Kesavardhana et al, "Stabilizing the Native Trimer of HIV-1 Env by Destabilizing the Heterodimeric Interface of the gp41 Postfusion Six-Helix Bundle," Journal of Virology, vol. 88, No. 17, pp. 9590-9604 (2014).
Khoo et al., "Adenovirus Infections in Human Immunodeficiency Virus-Positive Patients: Clinical Features and Molecular Epidemiology", J. Infect. Dis, vol. 172, No. 3, pp. 629-637 (1995) (Abstract Only).
Kim et al, "Comparison of HIV Type 1 ADA gp120 Monomers Versus gp140 Trimers as Immunogens for the Induction of Neutralizing Antibodies," AIDS Research and Human Retroviruses, vol. 21, No. 1, pp. 58-67 (2005).
Kobinger et al, "Chimpanzee Adenovirus Vaccine Protects Against Zaire Ebola Virus", Virology, vol. 346, pp. 394-401 (2006).
Kochanek et al, "A New Adenoviral Vector: Replacement of All Viral Coding Sequences with 28 kb of DNA Independently Expressing Both Full-Length Dystrophin and Beta-Galactosidase," Proceedings of the National Academy of Sciences of the United States of America, vol. 93, No. 12, pp. 5731-5736 (Jun. 1996).
Kong et al, "Uncleaved Prefusion-Optimized gp140 Trimers Derived From Analysis of HIV-1 Envelope Metastability," Nature Communications, vol. 7, No. 1, pp. 1-15 (2016).
Kong et al., "Expanded Breadth of the T -Cell Response to Mosaic Human Immunodeficiency Virus Type 1 Envelope DNA Vaccination," J. Viral., vol. 83, No. 5, pp. 2201-2215 (2009).
Korber et al., "T-Cell Vaccine Strategies for Human Immunodeficiency Virus, the Virus with a Thousand Faces," J. Viral., vol. 83, No. 17, pp. 8300-8314 (2009).
Kothe et al, "Ancestral and Consensus Envelope Immunogens for HIV-1 Subtype C," Virology, vol. 352, No. 2, pp. 438-449 (2006).
Kothe et al, "Antigenicity and Immunogenicity of HIV-1 Consensus Subtype B Envelope Glycoproteins," Virology, vol. 360, No. 1, pp. 218-234 (Mar. 30, 2007).
Kovacs et al., "HIV-1 Envelope Trimer Elicits more Potent Neutralizing Antibody Responses than Monomeric gp120", Proc. Natl. Acac. Sci., vol. 109, No. 30, pp. 12111-12116 (2012).
Kuschner et al., "A Phase 3, Randomized, Double-Blind, Placebo-Controlled Study of the Safety and Efficacy of the Live, Oral Adenovirus Type 4 and Type 7 Vaccine, in U.S. Military Recruits", Vaccine, vol. 31(28), pp. 2963-2971 (2013).
Kushnir et al, "Virus-Like Particles as a Highly Efficient Vaccine Platform: Diversity of Targets and Production Systems and Advances in Clinical Development," Vaccine, vol. 31, pp. 58-83 (2012).
Kwon et al, "Crystal Structure, Conformational Fixation and Entry-Related Interactions of Mature Ligand-Free HIV-1 ENV," Nature Structural & Molecular Biology, vol. 22, No. 7, pp. 522-531 (2015).
Kwong et al, "Structure of an HIV gp120 Envelope Glycoprotein in Complex with the CD4 Receptor and a Neutralizing Human Antibody," Nature, vol. 393, No. 6686, pp. 648-659 (Jun. 18, 1998).
Lasaro et al., "New Insights on Adenovirus as Vaccine Vectors", Mol. Ther., vol. 17, No. 8, pp. 1333-1339 (2009).
Lee et al, "A Single Point Mutation in HIV-1 V3 Loop Alters the Immunogenic Properties of rgp120," Archives of Virology, vol. 145, pp. 2087-2103 (2000).
Lepe-Zuniga et al., "Toxicity of Light-Exposed Hepes Media", Journ. of Immun. Methods, vol. 103, pp. 145 (1987).
Letvin et al., "Potent, Protective Anti-HIV Immune Responses Generated by Bimodal HIV Envelope DNA Plus Protein Vaccination", Proc. Natl. Acad. Sci., vol. 94, pp. 9378-9383 (1997).

(56) References Cited

OTHER PUBLICATIONS

Levine, "Why Do We Not Yet Have a Human Immunodeficiency Virus Vaccine," J. Virol., vol. 82, No. 24, pp. 11998-12000 (Dec. 2008).
Li et al, "Broad HIV-1 Neutralization Mediated by CD4-Binding Site Antibodies," Nature Medicine, vol. 13, No. 9, pp. 1032-1039 (Sep. 2007).
Li et al, "Characterization of Antibody Responses Elicited by Human Immunodeficiency Virus Type 1 Primary Isolate Trimeric and Monomeric Envelope Glycoproteins in Selected Adjuvants," Journal of Virology, vol. 80, No. 3, pp. 1414-1426 (Feb. 2006).
Li et al, "Evidence for Potent Autologous Neutralizing Antibody Titers and Compact Envelopes in Early Infection with Subtype C Human Immunodeficiency Virus Type 1," Journal of Virology, vol. 80, No. 11, pp. 5211-5218 (Jun. 2006).
Li et al, "Human Immunodeficiency Virus Type 1 env Clones from Acute and Early Subtype B Infections for Standardized Assessments of Vaccine-Elicited Neutralizing Antibodies," Journal of Virology, vol. 79, No. 16, pp. 10108-10125 (Aug. 2005).
Li et al, "Removal of a Single N-Linked Glycan in Human Immunodeficiency Virus Type 1 gp120 Results in an Enhanced Ability to Induce Neutralizing Antibody Responses," Journal of Virology, vol. 82, No. 2, pp. 638-651 (Jan. 2008).
Li et al., "Visualizing Antigen-Specific and Infected Cells in Situ Predicts Outcomes in Early Viral Infection", Science, vol. 323, No. 5922, pp. 1726-1729 (2009).
Lian et al., "Evaluation of Envelope Vaccines Derived from the South African Subtype C Human Immunodeficiency Virus Type 1 TV1 Strain," Journal of Virology, vol. 79, No. 21, pp. 13338-13349 (Nov. 2005).
Liao et al, "A Group M Consensus Envelope Glycoprotein Induces Antibodies That Neutralize Subsets of Subtype B and C HIV-1 Primary Viruses," Virology, vol. 353, No. 2, pp. 268-282 (Sep. 30, 2006).
Liao et al, "Antigenicity and Immunogenicity of Transmitted/Founder, Consensus, and Chronic Envelope Glycoproteins of Human Immunodeficiency Virus Type 1," Journal of Virology, vol. 87, No. 8, pp. 4185-4201 (Apr. 2013).
Liao et al, "Co-Evolution of a Broadly Neutralizing HIV-1 Antibody and Founder Virus," Nature, vol. 496, No. 7446, pp. 469-476 (Apr. 25, 2013).
Lin et al, "Designing Immunogens to Elicit Broadly Neutralizing Antibodies to the HIV-1 Envelope Glycoprotein," Current HIV Research, vol. 5, No. 6, pp. 514-541 (2007).
Liu et al., "Magnitude and Phenotype of Cellular Immune Responses Elicited by Recombinant Adenovirus Vectors and Heterologous Prime-Boost Regimens in Rhesus Monkeys", J. Viol., vol. 82, No. 10, pp. 4844-4852 (2008).
Liu et al., Immune Control of an SIV Challenge by a T-Cell-Based Vaccine in Rhesus Monkeys, Nature, vol. 457, No. 7225, pp. 87-91(2009).
Li et al, "Genetic and Neutralization Properties of Subtype C Human Immunodeficiency Virus Type 1 Molecular env Clones From Acute Early Heterosexually Acquired Infections in Southern Africa," Journal of Virology, vol. 80, No. 23, 11776-11790 (Dec. 2006).
Lopez-Sagaseta et al, "Self-Assembling Protein Nanoparticles in the Design of Vaccines," Computational and Structural Biotechnology Journal, vol. 14, pp. 58-68 (2016).
Lore et al., "Myeloid and Plasmacytoid Dendritic Cells are Susceptible to Recombinant Adenovirus Vectors and Stimulate Polyfunctional Memory T Cell Responses", J. Immunol, vol. 179, No. 3, pp. 1721-1729 (2007).
Lynch et al, "The Development of CD4 Binding Site Antibodies During HIV-1 Infection," Journal of Virology, vol. 86, No. 14, pp. 7588-7595 (Jul. 2012).
Saphire et al, "Crystal Structure of a Neutralizing Human IgG Against HIV-1: A Template for Vaccine Design," Science, vol. 293, No. 5532, pp. 1155-1159 (2001).
Sarzotti-Kelsoe et al, "Optimization and Validation of the TZM-bl Assay for Standardized Assessments of Neutralizing Antibodies Against HIV-1," Journal of Immunological Methods, vol. 409, pp. 131-146 (2014).
Sattentau, "Envelope Glycoprotein Trimers as HIV-1 Vaccine Immunogens", Vaccines, vol. 1, pp. 497-512 (2013).
Scheid et al, "Broad Diversity of Neutralizing Antibodies Isolated From Memory B Cells in HIV-Infected Individuals," D Nature, vol. 458, pp. 636-640 (Apr. 2, 2009).
Scheid et al, "Sequence and Structural Convergence of Broad and Potent HIV Antibodies That Mimic CD4 Binding," Science, vol. 333, pp. 1633-1637 (2011).
Schnierle et al, "Pseudotyping of Murine Leukemia Virus with the Envelope Glycoproteins of HIV Generates a Retroviral Vector with Specificity of infection for CD4-Expressing Cells," Proceedings of the National Academy of Sciences of the United States of America, vol. 94, pp. 8640-8645 (Aug. 1997).
Seaman et al, "Multiclade Human Immunodeficiency Virus Type 1 Envelope Immunogens Elicit Broad Cellular and Humoral Immunity in Rhesus Monkeys," Journal of Virology, vol. 79, No. 5, pp. 2956-2963 (2005).
Seaman et al, "Standardized Assessment of NAb Responses Elicited in Rhesus Monkeys Immunized with Single- or Multi-Glade HIV-1 Envelope Immunogens," Virology, vol. 367, pp. 175-186 (2007).
Sharma et al, "Cleavage-Independent HIV-1 Env Trimers Engineered as Soluble Native Spike Mimetics for Vaccines Design," Cell Reports, vol. 11, pp. 1-12 (2015).
Shu et al., "Efficient Boosting After Plasmid DNA or Recombinant Adenovirus Immunization with HIV-1 Vaccine Constructs", Vaccine, vol. 25, No. 8, pp. 1398-1408 (2007).
Simek et al, "Human Immunodeficiency Virus Type 1 Elite Neutralizers: Individuals With Broad and Potent Neutralizing Activity Identified by Using a High-Throughput Neutralization Assay Together With an Analytical Selection Algorithm," Journal of Virology, vol. 83, No. 14, pp. 7337-7348 (2009).
Sok et al, "Promiscuous Glycan Site Recognition by Antibodies to the High-Mannose Patch of gp120 Broadens Neutralization of HIV," Science Translational Medicine, vol. 6, No. 236, pp. 236ra63 (May 14, 2014).
Spranger et al., "Quantifying Adenovirus-Neutralizing Antibodies by Luciferase Transgene Detection: Addressing Preexisting Immunity to Vaccine and Gene Therapy Vectors", J. Clin. Microbiol, vol. 41, No. 11, pp. 5046-5052 (2003).
Stamatatos et al, "Neutralizing Antibodies Generated During Natural HIV-1 Infection: Good News for an HIV-1 Vaccine?," Nature Medicine, vol. 15, No. 8, pp. 866-870 (2009).
Tatsis et al., "A CD46-binding Chimpanzee Adenovirus Vector as a Vaccine Carrier", Molecular Therapy, vol. 15, No. 3, pp. 608-617 (2007).
Thorner et al., "Age Dependence of Adenovirus-Specific Neutralizing Antibody Titer in Individuals From Sub-Saharan Africa", J. Clin. Microbiol, vol. 44, No. 10, pp. 3781-3783 (2006).
Thurmond et al., "Web-Based Design and Evaluation of T-cell Vaccine Candidates," Bioinformatics, vol. 24, No. 14, pp. 1639-1640 (2008).
Uchiyama, "Liquid Formulation for Antibody Drugs", Biochimica Biophysica, vol. 1844, pp. 2041-2052 (2014).
Vaine et al, "Antibody Responses Elicited through Homologous or Heterologous Prime-Boost DNA and Protein Vaccinations Differ in Functional Activity and Avidity," Vaccine, vol. 28, No. 17, pp. 2999-3007 (2010).
Vaine et al, "Improved Induction of Antibodies Against Key Neutralizing Epitopes by Human Immunodeficiency Virus Type 1 gp120 DNA Prime-Protein Boost Vaccination Compared to gp120 Protein-Only Vaccination," Journal of Virology, vol. 82, No. 15, pp. 7369-7378 (Aug. 2008).
Vaine et al, "Profiles of Human Serum Antibody Responses Elicited by Three Leading HIV Vaccines Focusing on the Induction of Env-Specific Antibodies," PLoS One, vol. 5, No. 11, pp. e13916 (Nov. 2010).
Vogel et al, "The Majority of Neutralizing Abs in HIV-1-Infected Patients Recognize Linear V3 Loop Sequences," The Journal of Immunology, vol. 153, pp. 1895-1904 (1994).

(56) References Cited

OTHER PUBLICATIONS

Vogels et al., "Replication-Deficient Human Adenovirus Type 35 Vecotrs for Gene Transfer and Vaccination: Efficient Human Cell Infection and Bypass of Preexisting Adenovirus Immunity", J. Virol, vol. 77, No. 15, pp. 8263-8271 (2003).
Walker et al, "Broad and Potent Neutralizing Antibodies from an African Donor Reveal a New HIV-1 Vaccine Target," Science, vol. 326, No. 5950, pp. 285-289 (Oct. 9, 2009).
Walker et al, "Broad Neutralization Coverage of HIV by Multiple Highly Potent Antibodies," Nature, vol. 477, No. 7365, pp. 466-470 (Sep. 22, 2011).
Walker et al, "Toward an AIDS Vaccine," Science, vol. 320, pp. 760-764 (May 9, 2008).
Wang et al, "Cross-Subtype Antibody and Cellular Immune Responses Induced by a Polyvalent DNA Prime-Protein Boost HIV-1 Vaccine in Healthy Human Volunteers," Vaccine, vol. 26, No. 31, pp. 3947-3957 (Jul. 23, 2008).
Wang et al, "Enhanced Immunogenicity of gp120 Protein when Combined with Recombinant DNA Priming to Generate Antibodies that Neutralize the JR-FL Primary Isolate of Human Immunodeficiency Virus Type 1," Journal of Virology, vol. 79, No. 12, pp. 7933-7937 (Jun. 2005).
Wang et al, "Polyvalent HIV-1 Env Vaccine Formulations Delivered by the DNA Priming Plus Protein Boosting Approach are Effective in Generating Neutralizing Antibodies Against Primary Human Immunodeficiency Virus Type 1 Isolates from Subtypes A, B, C, D and E," Virology, vol. 350, No. 1, pp. 34-47 (2006).
Watkins et al, "Immune Escape by Human Immunodeficiency Virus Type 1 from Neutralizing Antibodies: Evidence for Multiple Pathways," Journal of Virology, vol. 67, No. 12, pp. 7493-7500 (Dec. 1993).
Wattanapitayakul et al, "Recent Developments in Gene Therapy for Cardiac Disease," Biomed & Pharmacother, vol. 54, No. 1, pp. 487-504 (2000).
Wiggan et al. "Novel Formulations Enhance the Thermal Stability of Live-Attenuated Flavivirus Vaccines," Vaccine, vol. 29, pp. 7456-7462 (2011).
Wiznerowicz et al, "Harnessing HIV for Therapy, Basic Research and Biotechnology," Trends in Biotechnology, vol. 23, No. 1, pp. 42-47 (Jan. 2005).
Written Opinion dated Mar. 21, 2014 in Int'l Application No. PCT/US2014/010543.
Wu et al, "Rational Design of Envelope Identifies Broadly Neutralizing Human Monoclonal Antibodies to HIV-1," Science, vol. 329, No. 5993, pp. 856-861 (Aug. 13, 2010).
Wyatt et al, "The Antigenic Structure of the HIV gp120 Envelope Glycoprotein," Nature, vol. 393, pp. 705-711 (Jun. 18, 1998).
Yang et al, "Improved Elicitation of Neutralizing Antibodies Against Primary Human Immunodeficiency Viruses by Soluble Stabilized Envelope Glycoprotein Trimers," Journal of Virology, vol. 75, No. 3, pp. 1165-1171 (Feb. 2001).
Yang et al, "Modifications That Stabilize Human Immunodeficiency Virus Envelope Glycoprotein Trimers in Solution," Journal of Virology, vol. 74, No. 10, pp. 4746-4754 (2000).
Yang et al., "Highly Stable Trimers Formed by Human Immunodeficiency Virus Type 1 Envelope Glycoproteins Fused with the Trimeric Motif of T4 Bacteriophage Fibritin", J. Virol., vol. 76, No. 9, pp. 4634-4642 (2002).
Yasmeen et al, "Differential Binding of Neutralizing and Non-Neutralizing Antibodies to Native-Like Soluble HIV-1 Env Trimers, Uncleaved Env Proteins, and Monomeric Subunits," Retrovirology, vol. 11, No. 41 (2014).
Zhang et al, "Expression, Purification, and Characterization of Recombinant HIV gp140," Journal of Biological Chemistry, vol. 276, No. 43, pp. 39577-39585 (2001).
Zhang et al, "Extensively Cross-Reactive Anti-HIV-1 Neutralizing Antibodies Induced by gp140 Immunization," PNAS, vol. 104, No. 24, pp. 10193-10198 (2007).
Zhao et al, "Nanoparticle Vaccines," Vaccines, vol. 32, pp. 327-337 (2014).
Zhou et al, "Structural Basis for Broad and Potent Neutralization of HIV-1 by Antibody VRC01," Science, vol. 329, No. 5993, pp. 811-817 (Aug. 13, 2010).
Zigler et al., "Analysis of the Cytotoxic Effects of Light-Exposed Hepes-Containing Culture Medium", In Vitro Cell Dev. Biol., vol. 21, No. 5, pp. 282-287 (1985).
Zolla-Pazner et al, "Focusing the Immune Response on the V3 Loop, a Neutralizing Epitope of the HIV-1 gp210 Envelope," Virology, vol. 372, pp. 233-246 (2008).
Desrosiers, "Prospects for an AIDS Vaccine", Nature Medicine, vol. 10, No. 3, pp. 221-223 (2004).
Dey et al, "Characterization of Human Immunodeficiency Virus Type 1 Monomeric and Trimeric gp120 Glycoproteins Stabilized in the CD4-Bound State: Antigenicity, Biophysics, and lmmunogenicity," Journal of Virology, vol. 81, No. 11, pp. 5579-5593 (Jun. 2007).
Doores et al, "Antibody 2G12 Recognizes Di-Mannose Equivalently in Domain- and Nondomain-Exchanged Forms But Only Binds the HIV-1 Glycan Shield if Domain Exchanged," Journal of Virology, vol. 84, No. 20, pp. 10690-10699 (2010).
Doria-Rose et al, "Frequency and Phenotype of Human Immunodeficiency Virus Envelope-Specific B Cells from Patients with Broadly Cross-Neutralizing Antibodies," Journal of Virology, vol. 83, No. 1, pp. 188-199 (Jan. 2009).
Eglen et al, "The Use of AlphaScreen Technology in HTS: Current Status," Current Chemical Genomics, vol. 1, pp. 2-10 (2008).
Engelhardt et al, "Ablation of E2A in Recombinant Adenoviruses Improves Transgene Persistence and Decreases Inflammatory Response in Mouse Liver," Proceedings of the National Academy of Sciences of the United States of America, vol. 91, No. 13, pp. 6196-6200 (Jun. 1994).
Falkowska et al, "PGV04, an HIV-1 gp120 CD4 Binding Site Antibody, is Broad and Potent in Neutralization but Does Not Induce Conformational Changes Characteristic of CD4," Journal of Virology, vol. 86, No. 8, pp. 4394-4403 (2012).
Farina et al., "Replication-defective Vector Based on a Chimpanzee Adenovirus", J. Virol, vol. 75, No. 23, pp. 11603-11613 (2001).
Fiebig et al, "Neutralizing Antibodies Against Conserved Domains of p15E of Porcine Endogenous Retroviruses: Basis for a Vaccine for Xenotransplantation?" Virology, vol. 307, No. 2, pp. 406-413 (2003).
Fischer et al, "Identification of a Peptide Mimicking the Binding Pattern of an Antiphospholipid Antibody," Immunobiology, vol. 211, No. 9, pp. 695-699 (2006).
Fischer et al., "Coping with Viral Diversity in HIV vaccine Design: A Response to Nickle et al.," PLoS Comput Bioi., vol. 4, No. 1, pp. 175-179 (2008).
Flynn et al., "Placebo-controlled phase 3 trial of a recombinant glycoprotein 120 vaccine to prevent HIV-1 infection",. J. Infect Dis, vol. 191, No. 5, pp. 654-665 (2005).
Freeman et al, "Crystal Structure of HIV-1 Primary Receptor CD4 in Complex with a Potent Antiviral Antibody," Structure, vol. 18, No. 12, pp. 1632-1641 (Dec. 8, 2010).
Frey et al, "A Fusion-Intermediate State of HIV-1 gp41 Targeted by Broadly Neutralizing Antibodies," Proceedings of be National Academy of Sciences of the United States of America, vol. 105, No. 10, pp. 3739-3744 (Mar. 11, 2008).
Fynan et al, "DNA Vaccines: Protective Immunizations by Parenteral, Mucosal, and Gene-Gun Inoculations," Proceedings of the National Academy of Sciences of the United States of America, vol. 90, No. 24, pp. 11478-11482 (Dec. 1993).
Gallo et al, "The HIV Env-mediated Fusion Reaction," Biochemics et Biophysica Acta, pp. 36-50 (2003).
Gallo, "The End or the Beginning of the Drive to an HIV-Preventive Vaccine: A View from over 20 Years", The Lancet, vol. 366, No. 9500, pp. 1894-1898 (Nov. 2005).
Gao et al, "A Comprehensive Panel of Near-Full-Length Clones and Reference Sequences for Non-Subtype B Isolates of Human Immunodeficiency Virus Type 1," Journal of Virology, vol. 72, No. 7, pp. 5680-5698 (1998).
Gao et al, "Antigenicity and Immunogenicity of a Synthetic Human Immunodeficiency Virus Type 1 Group M Consensus Envelope Glycoprotein," Journal of Virology, vol. 79, No. 2, pp. 1154-1163 (Jan. 2005).

(56) References Cited

OTHER PUBLICATIONS

Gao et al, "Centralized HIV-1 Envelope Immunogens and Neutralizing Antibodies," Current HIV Research, vol. 5, No. 5, pp. 572-577 (2007).
Gao et al, "Molecular Cloning and Analysis of Functional Envelope Genes from Human Immunodeficiency Virus Type 1 Sequence Subtypes a through G" Journal of Virology, vol. 70, No. 3, pp. 1651-1667 (Mar. 1996).
Gaschen et al, "Diversity Consideration in HIV-1 Vaccine Selection," Science, vol. 296, No. 5577, pp. 2354-2360 (Jun. 28, 2002).
Genbank Accession No. AF286227.1, "HIV-1 strain 97Za012 from South Africa, complete genome." Accessed Jan. 6, 2016.
GenBank Accession No. KC769514. Retrieved on Dec. 30, 2014 (2 pages).
Georgiev et al, "Delineating Antibody Recognition in Polyclonal Sera from Patterns of HIV-1 Isolate Neutralization," Science, vol. 340, No. 6133, pp. 751-756 (2013).
Georgiev et al, "Single-Chain Soluble BG505.SOSIP gp140 Trimers as Structural and Antigenic Mimics of Mature Closed HIV-1 Env," Journal of Virology, vol. 89, pp. 5318-5329 (2015).
Girard et al., A Review of Vaccine Research and Development: The Human Immunodeficiency Virus (HIV), Vaccine, vol. 24, pp. 4062-4081 (2006).
Gomez-Roman et al., "An Adenovirus-Based HIV Subtype B Prime/Boost Vaccine Regimen Elicits Antibodies Mediating Broad Antibody-Dependent Cellular Cytotoxicity Against Non-Subtype B HIV Strains", J. Acquir. Immune Defic. Syndr., vol. 43, No. 3, pp. 270-277 (Nov. 2006).
Gotch et al., "Candidate Vaccines for Immunotherapy in HIV", HIV Medicine, vol. 2, pp. 260-265 (2001).
Graham et al, "Phase 1 Safety and Immunogenicity Evaluation of a Multiclade HIV-1 DNA Candidate Vaccine," The Journal of Infectious Diseases, vol. 194, No. 12, pp. 1650-1660 (Dec. 15, 2006).
Gray et al, "Isolation of a Monoclonal Antibody That Targets the Alpha-2 Helix of gp120 and Represents the Initial Autologous Neutralizing-Antibody Response in an HIV-1 Subtype C-Infected Individual," Journal of Virology, vol. 85, No. 15, pp. 7719-7729 (Aug. 2011).
Gray et al., "Safety and Efficacy of the HVTN 503/Phambili Study of a Clade-B-based HIV-1 Vaccine in South Africa: A Double-Blind, Randomised, Placebo-Controlled Test-of-Concept Phase 2b Study", Lancet Infect Dis, vol. 11, No. 7, pp. 507-515 (2011).
Grundner et al, "Analysis of the Neutralizing Antibody Response Elicited in Rabbits by Repeated Inoculation with Trimeric HIV-1 Envelope Glycoproteins," Virology, vol. 331, No. 1, pp. 33-46 (2005).
Guenaga et al, "Glycine Substitution at Helix-To-Coil Transitions Facilitates the Structural Determination of a Stabilized Subtype C HIV Envelope Glycoprotein," Immunity, vol. 46, pp. 792-803 (2017).
Gurwith et al, "Safety and Immunogenicity of an Oral, Replicating Adenovirus Serotype 4 Vector Vaccine for H5N1 Influenza: A Randomised, Double-Blind, Placebo-Controlled, Phase 1 Study", Lancet Infect Dis, vol. 13, No. 3, pp. 238-250 (2013).
Hammer et al, "Efficacy Trial of a DNA/rAd5 HIV-1 Preventive Vaccine," The New England Journal of Medicine, vol. 369, No. 22, pp. 2083-2092 (Nov. 28, 2013).
Harris et al, "Trimeric HIV-1 Glycoprotein gp140 Immunogens and Native HIV-1 Envelope Glycoproteins Display the Same Closed and Open Quaternary Molecular Architectures," PNAS, vol. 108, No. 28, pp. 11440-11445 (2011).
Haslett et al., "Strong Human Immunodeficiency Virus (HIV)-Specific CD4+ T Cell Responses in a Cohort of Chronically Infected Patients are Associated with Interruptions in Anti-HIV Chemotherapy," J. Infect. Dis, vol. 81, No. 4, pp. 1264-1272 (2000).
Haynes et al, "Immune-Correlates Analysis of an HIV-1 Vaccine Efficacy Trial," The New England Journal of Medicine, vol. 366, No. 14, pp. 1275-1286 (2012).

He et al, "Presenting Native-Like Trimeric HIV-1 Antigens With Self-Assembling Nanoparticles," Nature Communications, vol. 7, No. 1, pp. 1-15 (2016).
Hierholzer et al., "Adenoviruses from Patients with AIDS: A Plethora of Serotypes and a Description of Five New Serotypes of Subgenus D (types 43-47).", J. Infect. Dis., vol. 158, No. 4 pp. 804-813 (1988) (Abstract Only).
Hoganson et al., "Development of a Stable Adenoviral Vector Formulation", BioProcessing Journ., pp. 43-48 (Mar. 2002).
Huang et al, "Broad and Potent Neutralization of HIV-1 by a gp41-Specific Human Antibody," Nature, vol. 491, No. 7424, pp. 406-412 (2012).
Int'l Preliminary Report on Patentability and Written Opinion dated May 24, 2011 in Int'l Application No. PCT/US2009/064999.
Int'l Preliminary Report on Patentability dated Jan. 26, 2017 in Int'l Application No. PCT/US2015/51891.
Int'l Preliminary Report on Patentability dated Apr. 5, 2016 in Int'l Application No. PCT/US2014/059093.
Int'l Preliminary Report on Patentability dated Jul. 7, 2015 in Int'l Application No. PCT/US2014/010543.
Int'l Preliminary Search Report on Patentability dated Apr. 12, 2011 in Int'l Application No. PCT/US2009/060494.
Int'l Search Report and Written Opinion dated Jan. 22, 2015 in Int'l Patent Application No. PCT/US2014/059093.
Int'l Search Report and Written Opinion dated Feb. 5, 2016 in Int'l Application No. PCT/US2015/051891.
"Endogenous Retrovirus Group K Member 25 Env Polyprotein", Database UNIPROT, Accession No. Q5GI17, 2 pages (Mar. 1, 2005).
"GCN4 Fusion Linker Peptide, SEQ ID No. 3," Database Geneseq, Accession No. AEN61500, 1 page (Mar. 8, 2007).
"Recombinant Protein gp41 Heterologous Transmembrane Region, SEQ ID1," Database Geneseq, Accession No. AUR74751, 1 page, (Mar. 19, 2009).
"Transmembrane Domain Peptide, SEQ ID 14," Database Geneseq, Accession No. AEF06609, 1 page (Mar. 23, 2006).
Abrahams et al, "Quantitating the Multiplicity of Infection with Human Immunodeficiency Virus Type 1 Subtype C Reveals a Non-Poisson Distribution of Transmitted Variants," Journal of Virology, vol. 83, No. 8, pp. 3556-3567 (Apr. 2009).
Abrahamyan et al, "The Cytoplasmic Tail Slows the Folding of Human Immunodeficiency Virus Type 1 Env from a late Prebundle Configuration into the Six-Helix Bundle", Journal of Virology, vol. 79, No. 1, pp. 106-115 (2005).
Altschul et al, "Gapped BLAST and PSI-BLAST: A New Generation of Protein Database Search Programs," Nucleic Acids Research, vol. 25, No. 17, pp. 3389-3402 (1997).
Amanna et al, "Contributions of Humoral and Cellular Immunity to Vaccine-Induced Protection in Humans," Virology, vol. 411, No. 2, pp. 206-215 (2011).
Ambrosini et al., "Gene Transfer in Astrocytes: Comparison Between Different Delivering Methods and Expression of the HIV-1 Protein Nef.", J. Neurosci. Res., vol. 55, p. 569 (1999) (Abstract Only).
Baba et al, "Human Neutralizing Monoclonal Antibodies of the IgG1 Subtype Protect Against Mucosal Simian-Human Immunodeficiency Virus Infection," Nature Medicine, vol. 6, No. 2, pp. 200-206 (2000).
Baden et al., "First-in-human Evalutation of the Safety and Immunogenicity of a Recombinant Adenovirus Serotype 26 HIV-1 Env Vaccine (IPCAVD 001)", J. Infect. Dis., vol. 207, No. 2, pp. 240-247 (2013).
Baicu et al., "Acid-base Buffering in Organ Preservation Solutions as a Function of Temperature: New Parameters for Comparing Buffer Capacity and Effciency", Cryobiology, vol. 45, pp. 33-48 (2002).
Bale et al, "Covalent Linkage of HIV-1 Trimers to Synthetic Liposomes Elicits Improved B Cell and Antibody Responses," Journal of Virology, vol. 91, No. 16, pp. e00443-17 (2017).
Bangari et al., "Development of Nonhuman Adenoviruses as Vaccine Vectors", Vaccine, vol. 24, No. 7, pp. 849-26 (2006).

(56) References Cited

OTHER PUBLICATIONS

Barnett et al, "Development of V2-deleted trimeric envelope vaccine candidates from human immunodeficiency virus type 1 (HIV-1) subtypes B and C," Microbes Infect., vol. 7, vol. 14, pp. 1386-1391 (2005).
Barouch et al., "Accelerating HIV-1 Vaccine Efficacy Trials", Cell, vol. 159, No. 5, pp. 969-792 (Nov. 2014).
Barouch et al., "Characterization of Humoral and Cellular Immune Responses Elicited by a Recombinant Adenovirus Serotype 26 HIV-1 Env Vaccine in Healthy Adults (IPCAVD 001)", J. Infect. Dis, vol. 207, No. 2, pp. 248-256 (2013).
Barouch et al., "International Seroepidemiology of Adenovirus Serotypes 5, 36, 35 and 48 in Pediatric and Adult Populations", Vaccine, vol. 29: pp. 5203-5209 (2011).
Barouch et al., "Protective Efficacy of Adenovirus/Protein Vaccines Against SIV Challenges in Rhesus Monkeys", Science, vol. 349, No. 6245, pp. 320-324 (Jul. 2015).
Barouch, "Challenges in the Development of an HIV-1 Vaccine", Nature, vol. 455, No. 2, pp. 613-619 (2008).
Beddows et al, "A Comparative Immunogenicity Study in Rabbits of Disulfide-Stablized, Proteolytically Cleaved, Soluble Trimeric Human Immunodeficiency Virus Type 1 gp140, Trimeric Cleavage-Defective gp140 and Monomeric gp120," Virology, vol. 360, pp. 329-340 (2007).
Berger et al, "Chemokine Receptors as HIV-1 Coreceptors: Roles in Viral Entry, Tropism and Disease," Annu. Rev. Immunol., vol. 17, pp. 657-700 (1999).
Berman et al, "Comparison of the Immune Response to Recombinant gp120 in Humans and Chimpanzees," AIDS, vol. 8, pp. 591-601 (1994).
Binley et al "A Recombinant Human Immunodeficiency Virus Type 1 Envelope Glycoprotein Complex Stabilized by 6 an Intermolecular Disulfide Bond Between the gp120 and gp41 Subunits is an Antigenic Mimic of the Trimeric Virion-Associated Structure," Journal of Virology, vol. 74, No. 2, pp. 627-643 (Jan. 2000).
Blondelle et al., "Immunogenically Optimized Peptides Derived from Natural Mutants of HIV CTL Epitopes and Peptide Combinational Libraries", Biopolymers, vol. 90(5), pp. 683-694 (2008).
Bower et al, "Elicitation of Neutralizing Antibodies with DNA Vaccines Expressing Soluble Stabilized Human Immunodefiency Virus Type 1 Envelope Glycoprotein Trimers Conjugated to C3d", Journ. of Viro., vol. 78, No. 9, pp. 4710-4719 (May 2004).
Bower et al, "HIV-1 Env gp 140 Trimers Elicit Neutralizing Antibodies Without Efficient Induction of Conformational Antibodies," Vaccine, vol. 24, pp. 5442-5451 (2006).
Buchbinder et al., Efficacy Assessment of a Cell-Mediated Immunity HIV-1 Vaccine (The Step Study): A Double-Blind, Randomised, Placebo-Controlled, Test-of-Concept Trial, Lancet, vol. 372 No. 9653, pp. 1881-1893 (2008).
Burke et al. "Neutralizing Antibody Responses to Subtype B and C Adjuvanted HIV Envelope Protein Vaccination in Rabbits," Virology, vol. 387, No. 1, pp. 147-156 (Apr. 2009).
Burton et al, "HIV Vaccine Design and the Neutralizing Antibody Problem," Nature Immunology, vol. 5, No. 3, pp. 233-236 (Mar. 2004).
Calarese et al, "Antibody Domain Exchange is an Immunological Solution to Carbohydrate Cluster Recognition," Science, vol. 300, No. 5628, pp. 2065-2071 (2003).
Cardoso et al, "Broadly Neutralizing Anti-HIV Antibody 4E10 Recognizes a Helical Conformation of a Highly Conserved Fusion-Associated Motif in gp41," Immunity, vol. 22, No. 2, pp. 163-173 (Feb. 2005).
Cardoso et al, "Structural Basis of Enhanced Binding of Extended and Helically Constrained Peptide Epitopes of the Broadly Neutralizing HIV-1 Antibody 4E1 0," Journal of Molecular Biology, vol. 365, No. 5, pp. 1533-1544 (2007).
Carrow et al, "High Prevalance of Antibodies to the gp120 V3 Regional Principal Neutralizing Determinant of HIV-1 MN in Sera from Africa and the Americas," Aids Research and Human Retroviruses, vol. 7, No. 10, pp. 831-838 (1991).

Catanzaro et al, "Phase I Clinical Evaluation of a Six-Plasmid Multiclade HIV-1 DNA Candidate Vaccine," Vaccine, vol. 25, No. 20, pp. 4085-4092 (2007).
Centlivre et al., "In HIV-1 Pathogenesis the Die is Cast During Primary Infections", AIDS, vol. 21, No. 1, pp. 1-11 (2007).
Checkley et al, "HIV-1 Envelope Glycoprotein Biosynthesis, Trafficking, and Incorporation," Journal of Molecular Biology, vol. 410, No. 4, pp. 582-608 (2011).
Chen et al, "Expression, Purification, and Characterization of gp160e, the Soluble, Trimeric Ectodomain of the Simian Immunodeficiency Virus Envelope Glycoprotein, gp160," The Journal of Biological Chemistry, vol. 275, No. 45, pp. 34946-34953 (Nov. 10, 2000).
Chen et al., A Chimeric Protein of Simian Immunodeficiency Virus Envelope Glycoprotein gp140 and *Escherichia coli* Asparatate Transcarbamoylase, J. Virol, vol. 78, No. 9, pp. 4508-4516 (2004).
Chen et al., "Adenovirus-Based Vaccines: Comparison of Vectors from Three Species of Adenoviridae", J. Virol, vol. 84, No. 20, pp. 10522-10532 (2010).
Cho et al, "Polyvalent Envelope Glycoprotein Vaccine Elicits a Broader Neutralizing Antibody Response But is Unable to Provide Sterilizing Protection Against Heterologous Simian/Human Immunodeficiency Virus Infection in Pigtailed Macaques," Journal of Virology, vol. 75, No. 5, pp. 2224-2234 (Mar. 2001).
Clapp et al. "Vaccines with Aluminum-Containing Adjuvants: Optimizing Vaccine Efficacy and Thermal Stability", J. Pharm. Sci. vol. 100, No. 2: pp. 388-401 (2011).
Cohen et al, "Chimpanzee Adenovirus CV-68 Adapted as a Gene Delivery Vector Interacts with the Coxsackievirus and Adenovirus Receptor", J. Gen. Virol., vol. 83, pp. 151-155 (2002).
Cohen, "Did Merck's Failed HIV Vaccine Cause Harm?" Science, vol. 318, pp. 1048-1049 (2007).
Cohen, "Naked DNA Points Way to Vaccines," Science, vol. 259, pp. 1691-1692 (Mar. 1993).
Crooks et al, "A Comparative Immunogenicity Study of HIV-1 Virus-Like Particles Bearing Various Forms of Envelope Proteins, Particles Bearing No Envelope and Soluble Monomeric gp120," ScienceDirect, Virology vol. 366, pp. 245-262 (2007).
Davenport et al, "Binding Interactions Between Soluble HIV Envelope Glycoproteins and Quaternary-Structure-Specific Monoclonal Antibodies PG9 and PG16," Journal of Virology, vol. 85, No. 14, pp. 7095-7107 (Jul. 2011).
De Gruijl et al., Intradermal Delivery of Adenoviral Type-35 Vectors Leads to High Efficiency Transduction of Mature, CD8+ T Cell-Stimulating Skin-Emigrated Dendritic Cells, J. Immunol, vol. 177, No. 4, pp. 2208-2215 (2006).
De Taeye et al, "Immunogenicity of Stabilized HIV-1 Envelope Trimers With Reduced Exposure of Non-Neutralizing Epitopes," Cell, vol. 163, pp. 1702-1715 (2015).
Derby et al, "Isolation and Characterization of Monoclonal Antibodies Elicited by Trimeric HIV-1 ENV gp140 Protein 14 Immunogens," Virology, vol. 366, pp. 433-445 (2007).
Int'l Search Report and Written Opinion dated Nov. 6, 2017 in Int'l Application No. PCT/US2017/049817.
Achenbach et al., "Effect of Therapeutic Intensification Followed by HIV DNA Prime AND rAd5 Boost Vaccination on HIV-specific Immunity and HIV Reservoir (EraMune 02): a Multicentre Randomised Clinical Trial", The Lancet, vol. 2, No. 3, pp. e82-e91 (Mar. 2015).
Gach et al., "HIV-1-Specific Antibody Response and Function after DNA Prime and Recombinant Adenovirus 5 Boost HIV Vaccine in HIV-Infected Subjects", PLOS One, vol. 11, No. 8, pp. 17 (Aug. 2016) e0160341.
Katlama et al., "Barriers to a Cure for HIV: New Ways to Target and Eradicate HIV-1 Reservoirs", The Lancet, vol. 381, No. 988., pp. 2109-2117 (Jun. 2013).
Thompson et al., "DNA/MVA Vaccination of HIV-1 Infected Participants with Viral Suppression on Antiretroviral Therapy, followed by Treatment Interruption: Elicitation of Immune Responses without Control of Re-Emergent Virus", PLOS ONE, vol. 11, No. 10, pp. 25 (Oct. 2016) e0163164.
Abbink et al., "Comparative Seroprevalence and Immunogenicity of Six Rare Serotype Recombinant Adenovirus Vaccine Vectors from Subgroups B and D", Jour. of Viro., vol. 81, No. 9, pp. 4654-4663 (May 2007).

(56) References Cited

OTHER PUBLICATIONS

Barouch et al., "Mosaic HIV-1 Vaccines Expand the Breadth and Depth of Cellular Immune Responses in Rhesus Monkeys", Nat. Med., vol. 16, No. 3, pp. 319-323 (Mar. 2010).
Barouch et al., "Protective Efficacy of a Global HIV-1 Mosaic Vaccine against Heterologous SHIV Challenges in Rhesus Monkeys", Cell, vol. 155, pp. 531-539 (Oct. 2013).
Blanchard et al., "Modified Vaccinia Virus Ankara Undergoes Limited Replication in Human Cells and Lacks Several Immunomodulatory Proteins: Implications for Use as a Human Vaccine", Journ. of Gen. Viro., vol. 79, pp. 1159-1167 (1998).
Carcelain et al., "Immune Interventions in HIV Infection", Immunol Rev., vol. 254, No. 1, pp. 355-371 (2013).
Carroll et al., "Host Range and Cytopathogenicity of the Highly Attenuated MVA Strain of Vaccinia Virus: Propagation and Generation of Recombinant Viruses in a Nonhuman Mammalian Cell Line", Virology, vol. 238, pp. 198-211 (1997).
Chen et al., "Protection of Rhesus Macaques Against Disease Progression from Pathogenic SHIV-89.6PD by Vaccination with Phage-Displayed HIV-1 Epitopes", Nat. Med., vol. 7, No. 11, pp. 1225-1231 (2001).
Fischer et al., "Polyvalent Vaccines for Optimal Coverage of Potential T-Cell Epitopes in Global HIV-1 Variants", Nat. Med., vol. 13, No. 1, pp. 100-106 (Jan. 2007).
Gianella et al., "Effect of Early Antiretroviral Therapy During Primary HIV-1 Infection on Cell-Associated HIV-1 DNA and Plasma HIV-1 RNA", Antiviral Therapy, vol. 16, No. 4, pp. 535-545 (2011).
Goujard et al., "HIV-1 Control After Transient Antiretroviral Treatment Initiated in Primary Infection: Role of Patient Characteristics and Effect of Therapy", Antiviral Therapy, vol. 17, No. 6, pp. 1001-1009 (2012).
Hamlyn et al., "Plasma HIV Viral Rebound Following Protocol-Indicated Cessation of ART Commenced in Primary and Chronic HIV Infection", PLOS ONE, vol. 7, No. 8, 8 pgs (Aug. 2012) e43754.
Havenga et al., "Novel Replication-Incompetent Adenoviral B-Group Vectors: High Vector Stability and Yield in PER. C6 Cells", Journ. of Gen Viro., vol. 87, pp. 2135-2143 (2006).
Lodi et al., "Immunovirologic Control 24 Months After Interruption of Antiretroviral Therapy Initiated Close to HIV Seroconversion", Archives of Internal Medicine, vol. 172, No. 16, pp. 1252-1255 (2012).
Saez-Cirion et al., "Post-Treatment HIV-1 Controllers with a Long-Term Virological Remission after the Interruption of Early Initiated Antiretroviral Therapy ANRS VISCONTI Study", PLOS Pathogens, vol. 9, No. 3, 12 pgs. (Mar. 2013) e1003211.
UNAIDS, "Report on the Global AIDS Epidemic" 198 pgs (2013).
Williams et al., "HIV-1 DNA Predicts Disease Progression and Post-Treatment Virological Control", eLIfe, vol. 3, 16 pgs (2014).
Stickl, "Smallpox Vaccination and it's Consequences: First Experiences with the Highly Attenuated Smallpox Vaccine MVA", Preventive Medicine, vol. 3, pp. 97-101 (1974).
Malherbe et al, "Sequential Immunization with a Subtype B HIV-1 Envelope Quasispecies Partially Mimics the In Vivo Development of Neutralizing Antibodies," Journal of Virology, vol. 85, No. 11, pp. 5262-5274 (Jun. 2011).
Mangeat et al, "Lentiviral Vectors and Antiretroviral Intrinsic Immunity," Human Gene Therapy, vol. 16, No. 8, pp. 913-920 (Aug. 2005).
Mascola et al, "Protection of Macaques Against Pathogenic Simian/Human Immunodeficiency Virus 89.6PD by Passive Transfer of Neutralizing Antibodies," Journal of Virology, vol. 73, No. 5, pp. 4009-4018 (May 1999).
Mascola et al, "Protection of Macaques Against Vaginal Transmission of a Pathogenic HIV-1/SIV Chimeric Virus by Passive Infusion of Neutralizing Antibodies," Nature Medicine, vol. 6, No. 2, pp. 207-210 (Feb. 2000).
Masopust et al., "Hidden Memories: Frontline Memory T Cells and Early Pathogen Interception", J. Immunol., vol. 188, No. 12, pp. 5811-5817 (2012).

Mast et al., "International Epidemiology of Human Pre-Existing Adenovirus (Ad) Type-5, Type-6, Type-26 and Type-36 Neutralizing Antibodies: Correlates of High Ad5 Titers and Implications for Potential HIV Vaccine Trials", Vaccine, vol. 28: pp. 950-957 (2010).
Mayr et al., "The Small Pox Vaccination Strain MVA: Marker, Genetic Structure, Experience Gained with the Parenteral Vaccination and Behavior in Organisms with a Debilitated Defence Mechanism," Zentralbl Bacteriol. vol. 167, pp. 375-390 (1978) (Abstract Only).
McBurney et al, "Evaluation of Heterologous Vaginal SHIV SF162p4 Infection Following Vaccination with a Polyvalent Clade B Virus-Like Particle Vaccine," AIDS Research and Humam Retroviruses, vol. 28, No. 9, pp. 863-872 (2012).
McBurney et al, "Human Immunodeficiency Virus-Like Particles with Consensus Envelopes Elicited Broader Cell-Mediated Peripheral and Mucosal Immune Responses than Polyvalent and Monovalent Env Vaccines," Vaccine, vol. 27, No. 32, pp. 4337-4349 (2009).
McCoy et al, "Potent and Broad Neutralization of HIV-1 by a Llama Antibody Elicited by Immunization," The Journal of Experimental Medicine, vol. 209, No. 6, pp. 1091-1103 (2012).
McElrath et al, "Induction of Immunity to Human Immunodeficiency Virus Type-1 by Vaccination," Immunity, vol. 33, pp. 542-554 (Oct. 29, 2010).
McElrath et al., "HIV-1 Vaccine-Induced Immunity in the Test-of-Concept Step Study: A Case-Cohort Analysis", Lancet, vol. 372, No. 9653, pp. 1894-1905 (2008).
McGuire et al, "Engineering HIV Envelope Protein to Activate Germline B Cell Receptors of Broadly Neutralizing Anti-CD4 Binding Site Antibodies," The Journal of Experimental Medicine, vol. 210, No. 4, pp. 655-663 (2013).
McLellan et al, "Structure of HIV-1 gp120 V1/V2 Domain with Broadly Neutralizing Antibody PG9," Nature, vol. 480, No. 7377, pp. 336-343 (2011).
Montefiori et al, "Antibody-Based HIV-1 Vaccines: Recent Developments and Future Directions," PLOS Medicine, vol. 4, No. 12, pp. e348 (2007).
Montefiori, "Evaluating Neutralizing Antibodies Against HIV, SIV, and SHIV in Luciferase Reporter Gene Assays," Current Protocols in Immunology, vol. 12, No. 11, pp. 1-17 (2004).
Montefiori, "Measuring HIV Neutralization in a Luciferase Reporter Gene Assay," HIV Protocols Second 25 Edition, vol. 485, pp. 395-405 (2009).
Morner et al, "Human Immunodeficiency Virus Type 1 ENV Trimer Immunization of Macaques and Impact of D Priming with Viral Vector or Stabilized Core Protein," Journal of Virology, vol. 83, No. 2, pp. 540-551 (Jan. 2009).
Mouquet et al, "Complex-Type N-Glycan Recognition by Potent Broadly Neutralizing HIV Antibodies," Proceedings of the National Academy of Sciences of the United States of America, vol. 109, No. 47, pp. E3268-E3277 (2012).
Muthumani et al., "HIV-1 Env DNA Vaccine plus PRotein Boost Delivered by EP Expands B- and T-Cell Responses and Neutralizing Phenotype In Vivo", PLOS One, vol. 8, No. 12, 12 pgs (Dec. 2013).
Nara et al, "Purified Envelope Glycoproteins from Human Immunodeficiency Virus Type 1 Variants Induce Individual, Type-Specific Neutralizing Antibodies," Journal of Virology, vol. 62, No. 8, pp. 2622-2628 (Aug. 1988).
NCBI Blast for GenBank AAY23526.1, Jul. 2016, "Envelope glycoprotein Human immunodeficiency virus 1", downloaded from web page: http://www.ncbi.nlm.nih.gov/protein/62956393, Download date: Feb. 8, 2018 (2 pages).
Nkolola et al, "Stability and Neutralization Capacity of a Novel Mosaic HIV-1 gp140 trimer in a Guinea Pig Model" AIDS Vaccine Poster, Ragon Institute, 1 pg. (2012).
Nkolola et al, "Stability and Neutralization Capacity of a Novel Mosaic HIV-1 gp140 Trimer in a Guinea Pig Model," Retrovirology, vol. 9, Supp. 2, pp. 299 (2012).
Nkolola et al., "Breadth of Neutralizing Antibodies Elicited by Stable, Homogeneous Clade A and Clade C HIV-1 gp140 Envelope Trimers in Guinea Pigs", Journ. of Viro., vol. 84. No. 7, pp. 3270-3279 (Apr. 2010).

(56) References Cited

OTHER PUBLICATIONS

Nkolola et al., "Characterization and Immunogenicity of a Novel Mosaic M HIV-1 gp140 Trimer", Journ. of Virology, vol. 88, No. 17, pp. 9538-9552 (Sep. 2014).

Ofek et al, "Structure and Mechanistic Analysis of the Anti-Human Immunodeficiency Virus Type 1 Antibody 2F5 in Complex with Its gp41 Epitope," Journal of Virology, vol. 78, No. 19, pp. 10724-10737 (Oct. 2004).

Page et al, "Studies on the Immunogenicity of Chinese Hamster Ovary Cell-Derived Recombinant gp120 (HIV-1111B)," Vaccine, vol. 9, pp. 47-52 (Jan. 1991).

Pancera et al, "Crystal Structure of PG16 and Chimeric Dissection with Somatically Related PG9: Structure-Function Analysis of Two Quaternary-Specific Antibodies That Effectively Neutralize HIV-1," Journal of Virology, vol. 84, No. 16, pp. 8098-8110 (Aug. 2010).

Pancera et al, "Structure of HIV-1 gp120 with gp41-Interactive Region Reveals Layered Envelope Architecture and Basis of Conformational Mobility," Procedures of the National Academy of Sciences of the United States of America, vol. 107, No. 3, pp. 1166-1171 (2010).

Pantophlet et al, "GP120: Target for Neutralizing HIV-1 Antibodies," Annu. Rev. Immunol., vol. 24, pp. 739-769 (2006).

Patterson et al. "Protection Against Mucosal Simian Immunodeficiency Virus SIVmac251 Challenge by Using Replicating Adenovirus-SIV Multigene Vaccine Priming and Subunit Boosting," Journal of Virology, vol. 78, No. 5, pp. 2212-2221 (Mar. 2004).

Pejchal et al, "A Potent and Broad Neutralizing Antibody Recognizes and Penetrates the HIV Glycan Shield," Science, vol. 334, No. 6059, pp. 1097-1103 (2011).

Pejchal et al, "Structure and Function of Broadly Reactive Antibody PG16 Reveal an H3 Subdomain that Mediates Potent Neutralization of HIV-1," Proceedings of the National Academy of Sciences of the United States of America, vol. 107, No. 25, pp. 11483-11488 (2010).

Peng et al. "Replicating Rather than Nonreplicating Adenovirus-Human Immunodeficiency Virus Recombinant Vaccines Are Better at Eliciting Potent Cellular Immunity and Priming High-Titer Antibodies," Journal of Virology, vol. 79, No. 16, pp. 10200-10209 (Aug. 2005).

Pinter, "Roles of HIV-1 Env Variable Regions in Viral Neutralization and Vaccine Development", Current HIV Research, vol. 5, No. 6, pp. 542-553 (2007).

Pitisuttihum et al., "Randomized, Double-Blind, Placebo-Controlled Efficacy Trial of a Bivalent Recombinant Glycoprotein 120 HIV-1 Vaccine Among Injection Drug Users in Bangkok, Thailand", J. Infect. Dis., vol. 194, No. 12, pp. 1661-1671 (2006).

Plotkin et al, "Postscript Relating to New Allegations Made by Edward Hooper at the Royal Society Discussion Meeting on Sep. 11, 2000," Philosophical Transactions of the Royal Society of London B: Biological Sciences, vol. 356, No. 1410, pp. 825-829 (2001).

Plotkin, "Correlates of Protection Induced by Vaccination," Clinical and Vaccine Immunology, vol. 17, No. 7, pp. 1055-1065 (Jul. 2010).

Plotkin, "Immunologic Correlates of Protection Induced by Vaccination," Pediatric Infectious Disease Journal, vol. 20, No. 1, pp. 63-75 (2001).

Plotkin, "The RV144 Thai HIV Vaccine Trial," Human Vaccines, vol. 6, No. 2, p. 159 (Feb. 2010).

Polonis et al, "Recent Advances in the Characterization of HIV-1 Neutralization Assays for Standardized Evaluation of the Antibody Response to Infection and Vaccination," Virology, vol. 375, pp. 315-320 (2008).

Pugach et al, "A Native-Like SOSIP.664 Trimer Based on an HIV-! Subtype B Env Gene," Journal of Virology, vol. 39, No. 6, pp. 3380-3395 (2015).

Rerks-Ngarm et al.", Vaccination with ALVAC and AIDSVAX to Prevent HIV-1 Infection in Thailand", N. Engl J Med., vol. 361, No. 23, pp. 2209-2220 (2009).

Rodenburg et al, "Near Full-Length Clones and Reference Sequences for Subtype C Isolates of HIV Type 1 from Three Different Continents," AIDS Research and Human Retroviruses, vol. 17, No. 2, pp. 161-168 (2001).

Salminen et al, "Full-length Sequence of an Ethiopian Human Immunodeficiency Virus Type 1 (HIV-1) Isolate of Genetic Subtype C," AIDS Res. Human Retroviruses, vol. 12, No. 14, pp. 1329-1339 (1996).

Sanders et al, "HIV-1 Neutralizing Antibodies Induced by Native-Like Envelope Trimers," Science, vol. 349, Issue 6244, pp. 1-17 (2015).

Sanders et al, "Stabilization of the Solubale, Cleaved, Trimeric Form of the Envelope Glycoprotein Complex of Human Immunodeficiency Virus Type 1," Journal of Virology, vol. 76, No. 17, pp. 8875-8889 (2002).

Sanders et al., "Brunenders: A Partially Attenuated Historic Poliovirus Type 1 Vaccine Strain", Journ. of General Viro., vol. 96, pp. 2614-2622 (2015).

Santra et al., "Mosaic Vaccines Elicit CD8+ T Lymphocyte Responses That Confer Enhanced Immune Coverage of Diverse HIV Strains in Monkeys", Nat Med., vol. 16, No. 3, pp. 324-328 (2010).

* cited by examiner

SEQUENCE LISTING

<160> NUMBER OF SEQ ID NOS: 8

<210> SEQ ID NO 1
<211> LENGTH: 685
<212> TYPE: PRT
<213> ORGANISM: Artificial Sequence
<220> FEATURE:
<223> OTHER INFORMATION: Mos1.Env protein sequence

<400> SEQUENCE: 1

```
Met Arg Val Thr Gly Ile Arg Lys Asn Tyr Gln His Leu Trp Arg Trp
1               5                   10                  15

Gly Thr Met Leu Leu Gly Ile Leu Met Ile Cys Ser Ala Ala Gly Lys
            20                  25                  30

Leu Trp Val Thr Val Tyr Tyr Gly Val Pro Val Trp Lys Glu Ala Thr
        35                  40                  45

Thr Thr Leu Phe Cys Ala Ser Asp Ala Lys Ala Tyr Asp Thr Glu Val
    50                  55                  60

His Asn Val Trp Ala Thr His Ala Cys Val Pro Thr Asp Pro Asn Pro
65                  70                  75                  80

Gln Glu Val Val Leu Glu Asn Val Thr Glu Asn Phe Asn Met Trp Lys
                85                  90                  95

Asn Asn Met Val Glu Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Asn Cys Thr Asp Asp Val Arg Asn Val Thr Asn Asn Ala Thr Asn Thr
    130                 135                 140

Asn Ser Ser Trp Gly Glu Pro Met Glu Lys Gly Glu Ile Lys Asn Cys
145                 150                 155                 160

Ser Phe Asn Ile Thr Thr Ser Ile Arg Asn Lys Val Gln Lys Gln Tyr
                165                 170                 175

Ala Leu Phe Tyr Lys Leu Asp Val Val Pro Ile Asp Asn Asp Ser Asn
            180                 185                 190

Asn Thr Asn Tyr Arg Leu Ile Ser Cys Asn Thr Ser Val Ile Thr Gln
        195                 200                 205

Ala Cys Pro Lys Val Ser Phe Glu Pro Ile Pro Ile His Tyr Cys Ala
    210                 215                 220

Pro Ala Gly Phe Ala Ile Leu Lys Cys Asn Asp Lys Lys Phe Asn Gly
225                 230                 235                 240

Thr Gly Pro Cys Thr Asn Val Ser Thr Val Gln Cys Thr His Gly Ile
                245                 250                 255

Arg Pro Val Val Ser Thr Gln Leu Leu Leu Asn Gly Ser Leu Ala Glu
            260                 265                 270

Glu Glu Val Val Ile Arg Ser Glu Asn Phe Thr Asn Asn Ala Lys Thr
        275                 280                 285

Ile Met Val Gln Leu Asn Val Ser Val Glu Ile Asn Cys Thr Arg Pro
    290                 295                 300

Asn Asn Asn Thr Arg Lys Ser Ile His Ile Gly Pro Gly Arg Ala Phe
305                 310                 315                 320

Tyr Thr Ala Gly Asp Ile Ile Gly Asp Ile Arg Gln Ala His Cys Asn
```

```
            325                 330                 335
Ile Ser Arg Ala Asn Trp Asn Asn Thr Leu Arg Gln Ile Val Glu Lys
            340                 345                 350

Leu Gly Lys Gln Phe Gly Asn Asn Lys Thr Ile Val Phe Asn His Ser
            355                 360                 365

Ser Gly Gly Asp Pro Glu Ile Val Met His Ser Phe Asn Cys Gly Gly
            370                 375                 380

Glu Phe Phe Tyr Cys Asn Ser Thr Lys Leu Phe Asn Ser Thr Trp Thr
385                 390                 395                 400

Trp Asn Asn Ser Thr Trp Asn Asn Thr Lys Arg Ser Asn Asp Thr Glu
                405                 410                 415

Glu His Ile Thr Leu Pro Cys Arg Ile Lys Gln Ile Ile Asn Met Trp
                420                 425                 430

Gln Glu Val Gly Lys Ala Met Tyr Ala Pro Pro Ile Arg Gly Gln Ile
                435                 440                 445

Arg Cys Ser Ser Asn Ile Thr Gly Leu Leu Leu Thr Arg Asp Gly Gly
            450                 455                 460

Asn Asp Thr Ser Gly Thr Glu Ile Phe Arg Pro Gly Gly Gly Asp Met
465                 470                 475                 480

Arg Asp Asn Trp Arg Ser Glu Leu Tyr Lys Tyr Lys Val Val Lys Ile
                485                 490                 495

Glu Pro Leu Gly Val Ala Pro Thr Lys Ala Lys Arg Arg Val Val Gln
                500                 505                 510

Ser Glu Lys Ser Ala Val Gly Ile Gly Ala Val Phe Leu Gly Phe Leu
            515                 520                 525

Gly Ala Ala Gly Ser Thr Met Gly Ala Ala Ser Met Thr Leu Thr Val
            530                 535                 540

Gln Ala Arg Leu Leu Leu Ser Gly Ile Val Gln Gln Asn Asn Leu
545                 550                 555                 560

Leu Arg Ala Ile Glu Ala Gln Gln His Leu Leu Gln Leu Thr Val Trp
                565                 570                 575

Gly Ile Lys Gln Leu Gln Ala Arg Val Leu Ala Val Glu Arg Tyr Leu
                580                 585                 590

Lys Asp Gln Gln Leu Leu Gly Ile Trp Gly Cys Ser Gly Lys Leu Ile
                595                 600                 605

Cys Thr Thr Thr Val Pro Trp Asn Ala Ser Trp Ser Asn Lys Ser Leu
            610                 615                 620

Asp Lys Ile Trp Asn Asn Met Thr Trp Met Glu Trp Glu Arg Glu Ile
625                 630                 635                 640

Asn Asn Tyr Thr Ser Leu Ile Tyr Thr Leu Ile Glu Glu Ser Gln Asn
                645                 650                 655

Gln Gln Glu Lys Asn Glu Gln Glu Leu Leu Glu Leu Asp Lys Trp Ala
                660                 665                 670

Ser Leu Trp Asn Trp Phe Asp Ile Ser Asn Trp Leu Trp
            675                 680                 685

<210> SEQ ID NO 2
<211> LENGTH: 684
<212> TYPE: PRT
<213> ORGANISM: Artificial Sequence
<220> FEATURE:
<223> OTHER INFORMATION: Mos2.Env protein sequence

<400> SEQUENCE: 2

Met Arg Val Arg Gly Ile Gln Arg Asn Trp Pro Gln Trp Trp Ile Trp
```

-continued

```
1               5                   10                  15
Gly Ile Leu Gly Phe Trp Met Ile Ile Cys Arg Val Met Gly Asn
                20                  25                  30

Leu Trp Val Thr Val Tyr Tyr Gly Val Pro Val Trp Lys Glu Ala Lys
                35                  40                  45

Thr Thr Leu Phe Cys Ala Ser Asp Ala Lys Ala Tyr Glu Lys Glu Val
        50                  55                  60

His Asn Val Trp Ala Thr His Ala Cys Val Pro Thr Asp Pro Asn Pro
65                  70                  75                  80

Gln Glu Met Val Leu Glu Asn Val Thr Glu Asn Phe Asn Met Trp Lys
                85                  90                  95

Asn Asp Met Val Asp Gln Met His Glu Asp Ile Ile Arg Leu Trp Asp
                100                 105                 110

Gln Ser Leu Lys Pro Cys Val Lys Leu Thr Pro Leu Cys Val Thr Leu
                115                 120                 125

Glu Cys Arg Asn Val Arg Asn Val Ser Ser Asn Gly Thr Tyr Asn Ile
        130                 135                 140

Ile His Asn Glu Thr Tyr Lys Glu Met Lys Asn Cys Ser Phe Asn Ala
145                 150                 155                 160

Thr Thr Val Val Glu Asp Arg Lys Gln Lys Val His Ala Leu Phe Tyr
                165                 170                 175

Arg Leu Asp Ile Val Pro Leu Asp Glu Asn Asn Ser Ser Glu Lys Ser
                180                 185                 190

Ser Glu Asn Ser Ser Glu Tyr Tyr Arg Leu Ile Asn Cys Asn Thr Ser
        195                 200                 205

Ala Ile Thr Gln Ala Cys Pro Lys Val Ser Phe Asp Pro Ile Pro Ile
210                 215                 220

His Tyr Cys Ala Pro Ala Gly Tyr Ala Ile Leu Lys Cys Asn Asn Lys
225                 230                 235                 240

Thr Phe Asn Gly Thr Gly Pro Cys Asn Asn Val Ser Thr Val Gln Cys
                245                 250                 255

Thr His Gly Ile Lys Pro Val Val Ser Thr Gln Leu Leu Leu Asn Gly
        260                 265                 270

Ser Leu Ala Glu Glu Ile Ile Ile Arg Ser Glu Asn Leu Thr Asn
        275                 280                 285

Asn Ala Lys Thr Ile Ile Val His Leu Asn Glu Thr Val Asn Ile Thr
290                 295                 300

Cys Thr Arg Pro Asn Asn Asn Thr Arg Lys Ser Ile Arg Ile Gly Pro
305                 310                 315                 320

Gly Gln Thr Phe Tyr Ala Thr Gly Asp Ile Ile Gly Asp Ile Arg Gln
                325                 330                 335

Ala His Cys Asn Leu Ser Arg Asp Gly Trp Asn Lys Thr Leu Gln Gly
        340                 345                 350

Val Lys Lys Lys Leu Ala Glu His Phe Pro Asn Lys Thr Ile Asn Phe
        355                 360                 365

Thr Ser Ser Ser Gly Gly Asp Leu Glu Ile Thr Thr His Ser Phe Asn
        370                 375                 380

Cys Arg Gly Glu Phe Phe Tyr Cys Asn Thr Ser Gly Leu Phe Asn Gly
385                 390                 395                 400

Thr Tyr Met Pro Asn Gly Thr Asn Ser Asn Ser Ser Asn Ile Thr
                405                 410                 415

Leu Pro Cys Arg Ile Lys Gln Ile Ile Asn Met Trp Gln Glu Val Gly
                420                 425                 430
```

-continued

Arg Ala Met Tyr Ala Pro Pro Ile Ala Gly Asn Ile Thr Cys Arg Ser
            435                 440                 445

Asn Ile Thr Gly Leu Leu Thr Arg Asp Gly Gly Ser Asn Asn Gly
    450                 455                 460

Val Pro Asn Asp Thr Glu Thr Phe Arg Pro Gly Gly Gly Asp Met Arg
465                 470                 475                 480

Asn Asn Trp Arg Ser Glu Leu Tyr Lys Tyr Lys Val Val Glu Val Lys
                485                 490                 495

Pro Leu Gly Val Ala Pro Thr Glu Ala Lys Arg Arg Val Val Glu Ser
            500                 505                 510

Glu Lys Ser Ala Val Gly Ile Gly Ala Val Phe Leu Gly Ile Leu Gly
        515                 520                 525

Ala Ala Gly Ser Thr Met Gly Ala Ala Ser Ile Thr Leu Thr Val Gln
    530                 535                 540

Ala Arg Gln Leu Leu Ser Gly Ile Val Gln Gln Ser Asn Leu Leu
545                 550                 555                 560

Arg Ala Ile Glu Ala Gln Gln His Met Leu Gln Leu Thr Val Trp Gly
                565                 570                 575

Ile Lys Gln Leu Gln Thr Arg Val Leu Ala Ile Glu Arg Tyr Leu Gln
            580                 585                 590

Asp Gln Gln Leu Leu Gly Leu Trp Gly Cys Ser Gly Lys Leu Ile Cys
        595                 600                 605

Thr Thr Ala Val Pro Trp Asn Thr Ser Trp Ser Asn Lys Ser Gln Thr
    610                 615                 620

Asp Ile Trp Asp Asn Met Thr Trp Met Gln Trp Asp Lys Glu Ile Gly
625                 630                 635                 640

Asn Tyr Thr Gly Glu Ile Tyr Arg Leu Leu Glu Glu Ser Gln Asn Gln
                645                 650                 655

Gln Glu Lys Asn Glu Lys Asp Leu Leu Ala Leu Asp Ser Trp Lys Asn
            660                 665                 670

Leu Trp Asn Trp Phe Asp Ile Thr Asn Trp Leu Trp
        675                 680

<210> SEQ ID NO 3
<211> LENGTH: 1350
<212> TYPE: PRT
<213> ORGANISM: Artificial Sequence
<220> FEATURE:
<223> OTHER INFORMATION: Mos1.Gag-Pol protein sequence

<400> SEQUENCE: 3

Met Gly Ala Arg Ala Ser Val Leu Ser Gly Gly Glu Leu Asp Arg Trp
1               5                   10                  15

Glu Lys Ile Arg Leu Arg Pro Gly Gly Lys Lys Tyr Arg Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Val Ala Thr Leu Tyr Cys Val His Gln Arg Ile Glu Ile Lys Asp
                85                  90                  95

Thr Lys Glu Ala Leu Glu Lys Ile Glu Glu Glu Gln Asn Lys Ser Lys
            100                 105                 110

```
Lys Lys Ala Gln Gln Ala Ala Asp Thr Gly Asn Ser Ser Gln Val
        115                 120                 125
Ser Gln Asn Tyr Pro Ile Val Gln Asn Ile Gln Gly Gln Met Val His
    130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
        195                 200                 205
Ala Ala Glu Trp Asp Arg Val His Pro Val His Ala Gly Pro Ile Ala
    210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr Asn Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Val Ser Ile Leu Asp Ile Arg Gln Gly
        275                 280                 285
Pro Lys Glu Pro Phe Arg Asp Tyr Val Asp Arg Phe Tyr Lys Thr Leu
    290                 295                 300
Arg Ala Glu Gln Ala Ser Gln Asp Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Ala Ala Thr Leu Glu Glu Met Met Thr Ala Cys Gln Gly
            340                 345                 350
Val Gly Gly Pro Gly His Lys Ala Arg Val Leu Ala Glu Ala Met Ser
        355                 360                 365
Gln Val Thr Asn Ser Ala Thr Ile Met Met Gln Arg Gly Asn Phe Arg
    370                 375                 380
Asn Gln Arg Lys Thr Val Lys Cys Phe Asn Cys Gly Lys Glu Gly His
385                 390                 395                 400
Ile Ala Lys Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
Phe Leu Gly Lys Ile Trp Pro Ser Asn Lys Gly Arg Pro Gly Asn Phe
        435                 440                 445
Leu Gln Asn Arg Pro Glu Pro Thr Ala Pro Pro Glu Glu Ser Phe Arg
    450                 455                 460
Phe Gly Glu Glu Thr Thr Thr Pro Ser Gln Lys Gln Glu Pro Ile Asp
465                 470                 475                 480
Lys Glu Met Tyr Pro Leu Ala Ser Leu Lys Ser Leu Phe Gly Asn Asp
                485                 490                 495
Pro Ser Ser Gln Met Ala Pro Ile Ser Pro Ile Glu Thr Val Pro Val
            500                 505                 510
Lys Leu Lys Pro Gly Met Asp Gly Pro Arg Val Lys Gln Trp Pro Leu
        515                 520                 525
```

```
Thr Glu Glu Lys Ile Lys Ala Leu Thr Ala Ile Cys Glu Glu Met Glu
    530                 535                 540
Lys Glu Gly Lys Ile Thr Lys Ile Gly Pro Glu Asn Pro Tyr Asn Thr
545                 550                 555                 560
Pro Val Phe Ala Ile Lys Lys Lys Asp Ser Thr Lys Trp Arg Lys Leu
                565                 570                 575
Val Asp Phe Arg Glu Leu Asn Lys Arg Thr Gln Asp Phe Trp Glu Val
            580                 585                 590
Gln Leu Gly Ile Pro His Pro Ala Gly Leu Lys Lys Lys Ser Val
        595                 600                 605
Thr Val Leu Ala Val Gly Asp Ala Tyr Phe Ser Val Pro Leu Asp Glu
    610                 615                 620
Gly Phe Arg Lys Tyr Thr Ala Phe Thr Ile Pro Ser Thr Asn Asn Glu
625                 630                 635                 640
Thr Pro Gly Ile Arg Tyr Gln Tyr Asn Val Leu Pro Gln Gly Trp Lys
                645                 650                 655
Gly Ser Pro Ala Ile Phe Gln Cys Ser Met Thr Arg Ile Leu Glu Pro
            660                 665                 670
Phe Arg Ala Lys Asn Pro Glu Ile Val Ile Tyr Gln Tyr Met Ala Ala
        675                 680                 685
Leu Tyr Val Gly Ser Asp Leu Glu Ile Gly Gln His Arg Ala Lys Ile
    690                 695                 700
Glu Glu Leu Arg Glu His Leu Leu Lys Trp Gly Phe Thr Thr Pro Asp
705                 710                 715                 720
Lys Lys His Gln Lys Glu Pro Pro Phe Leu Trp Met Gly Tyr Glu Leu
                725                 730                 735
His Pro Asp Lys Trp Thr Val Gln Pro Ile Gln Leu Pro Glu Lys Asp
            740                 745                 750
Ser Trp Thr Val Asn Asp Ile Gln Lys Leu Val Gly Lys Leu Asn Trp
        755                 760                 765
Ala Ser Gln Ile Tyr Pro Gly Ile Lys Val Arg Gln Leu Cys Lys Leu
    770                 775                 780
Leu Arg Gly Ala Lys Ala Leu Thr Asp Ile Val Pro Leu Thr Glu Glu
785                 790                 795                 800
Ala Glu Leu Glu Leu Ala Glu Asn Arg Glu Ile Leu Lys Glu Pro Val
                805                 810                 815
His Gly Val Tyr Tyr Asp Pro Ser Lys Asp Leu Ile Ala Glu Ile Gln
            820                 825                 830
Lys Gln Gly His Asp Gln Trp Thr Tyr Gln Ile Tyr Gln Glu Pro Phe
        835                 840                 845
Lys Asn Leu Lys Thr Gly Lys Tyr Ala Lys Met Arg Thr Ala His Thr
    850                 855                 860
Asn Asp Val Lys Gln Leu Thr Glu Ala Val Gln Lys Ile Ala Met Glu
865                 870                 875                 880
Ser Ile Val Ile Trp Gly Lys Thr Pro Lys Phe Arg Leu Pro Ile Gln
                885                 890                 895
Lys Glu Thr Trp Glu Thr Trp Trp Thr Asp Tyr Trp Gln Ala Thr Trp
            900                 905                 910
Ile Pro Glu Trp Glu Phe Val Asn Thr Pro Pro Leu Val Lys Leu Trp
        915                 920                 925
Tyr Gln Leu Glu Lys Asp Pro Ile Ala Gly Val Glu Thr Phe Tyr Val
    930                 935                 940
Ala Gly Ala Ala Asn Arg Glu Thr Lys Leu Gly Lys Ala Gly Tyr Val
```

-continued

```
945                 950                 955                 960
Thr Asp Arg Gly Arg Gln Lys Ile Val Ser Leu Thr Glu Thr Thr Asn
                965                 970                 975
Gln Lys Thr Ala Leu Gln Ala Ile Tyr Leu Ala Leu Gln Asp Ser Gly
                980                 985                 990
Ser Glu Val Asn Ile Val Thr Ala Ser Gln Tyr Ala Leu Gly Ile Ile
                995                1000                1005
Gln Ala Gln Pro Asp Lys Ser Glu Ser Glu Leu Val Asn Gln Ile
       1010                1015                1020
Ile Glu Gln Leu Ile Lys Lys Glu Arg Val Tyr Leu Ser Trp Val
       1025                1030                1035
Pro Ala His Lys Gly Ile Gly Gly Asn Glu Gln Val Asp Lys Leu
       1040                1045                1050
Val Ser Ser Gly Ile Arg Lys Val Leu Phe Leu Asp Gly Ile Asp
       1055                1060                1065
Lys Ala Gln Glu Glu His Glu Lys Tyr His Ser Asn Trp Arg Ala
       1070                1075                1080
Met Ala Ser Asp Phe Asn Leu Pro Pro Val Val Ala Lys Glu Ile
       1085                1090                1095
Val Ala Ser Cys Asp Gln Cys Gln Leu Lys Gly Glu Ala Met His
       1100                1105                1110
Gly Gln Val Asp Cys Ser Pro Gly Ile Trp Gln Leu Ala Cys Thr
       1115                1120                1125
His Leu Glu Gly Lys Ile Ile Leu Val Ala Val His Val Ala Ser
       1130                1135                1140
Gly Tyr Ile Glu Ala Glu Val Ile Pro Ala Glu Thr Gly Gln Glu
       1145                1150                1155
Thr Ala Tyr Phe Ile Leu Lys Leu Ala Gly Arg Trp Pro Val Lys
       1160                1165                1170
Val Ile His Thr Ala Asn Gly Ser Asn Phe Thr Ser Ala Ala Val
       1175                1180                1185
Lys Ala Ala Cys Trp Trp Ala Gly Ile Gln Gln Glu Phe Gly Ile
       1190                1195                1200
Pro Tyr Asn Pro Gln Ser Gln Gly Val Val Ala Ser Met Asn Lys
       1205                1210                1215
Glu Leu Lys Lys Ile Ile Gly Gln Val Arg Asp Gln Ala Glu His
       1220                1225                1230
Leu Lys Thr Ala Val Gln Met Ala Val Phe Ile His Asn Phe Lys
       1235                1240                1245
Arg Lys Gly Gly Ile Gly Gly Tyr Ser Ala Gly Glu Arg Ile Ile
       1250                1255                1260
Asp Ile Ile Ala Thr Asp Ile Gln Thr Lys Glu Leu Gln Lys Gln
       1265                1270                1275
Ile Ile Lys Ile Gln Asn Phe Arg Val Tyr Tyr Arg Asp Ser Arg
       1280                1285                1290
Asp Pro Ile Trp Lys Gly Pro Ala Lys Leu Leu Trp Lys Gly Glu
       1295                1300                1305
Gly Ala Val Val Ile Gln Asp Asn Ser Asp Ile Lys Val Val Pro
       1310                1315                1320
Arg Arg Lys Val Lys Ile Ile Lys Asp Tyr Gly Lys Gln Met Ala
       1325                1330                1335
Gly Ala Asp Cys Val Ala Gly Arg Gln Asp Glu Asp
       1340                1345                1350
```

<210> SEQ ID NO 4
<211> LENGTH: 1341
<212> TYPE: PRT
<213> ORGANISM: Artificial Sequence
<220> FEATURE:
<223> OTHER INFORMATION: Mos2.Gag-Pol protein sequence

<400> SEQUENCE: 4

```
Met Gly Ala Arg Ala Ser Ile Leu Arg Gly Gly Lys Leu Asp Lys Trp
1               5                   10                  15

Glu Lys Ile Arg Leu Arg Pro Gly Gly Lys Lys His Tyr Met Leu Lys
            20                  25                  30

His Leu Val Trp Ala Ser Arg Glu Leu Glu Arg Phe Ala Leu Asn Pro
        35                  40                  45

Gly Leu Leu Glu Thr Ser Glu Gly Cys Lys Gln Ile Ile Lys Gln Leu
    50                  55                  60

Gln Pro Ala Leu Gln Thr Gly Thr Glu Glu Leu Arg Ser Leu Phe Asn
65                  70                  75                  80

Thr Val Ala Thr Leu Tyr Cys Val His Ala Glu Ile Glu Val Arg Asp
                85                  90                  95

Thr Lys Glu Ala Leu Asp Lys Ile Glu Glu Gln Asn Lys Ser Gln
            100                 105                 110

Gln Lys Thr Gln Gln Ala Lys Glu Ala Asp Gly Lys Val Ser Gln Asn
        115                 120                 125

Tyr Pro Ile Val Gln Asn Leu Gln Gly Gln Met Val His Gln Pro Ile
    130                 135                 140

Ser Pro Arg Thr Leu Asn Ala Trp Val Lys Val Ile Glu Glu Lys Ala
145                 150                 155                 160

Phe Ser Pro Glu Val Ile Pro Met Phe Thr Ala Leu Ser Glu Gly Ala
                165                 170                 175

Thr Pro Gln Asp Leu Asn Thr Met Leu Asn Thr Val Gly Gly His Gln
            180                 185                 190

Ala Ala Met Gln Met Leu Lys Asp Thr Ile Asn Glu Glu Ala Ala Glu
        195                 200                 205

Trp Asp Arg Leu His Pro Val His Ala Gly Pro Val Ala Pro Gly Gln
    210                 215                 220

Met Arg Glu Pro Arg Gly Ser Asp Ile Ala Gly Thr Thr Ser Asn Leu
225                 230                 235                 240

Gln Glu Gln Ile Ala Trp Met Thr Ser Asn Pro Pro Ile Pro Val Gly
                245                 250                 255

Asp Ile Tyr Lys Arg Trp Ile Ile Leu Gly Leu Asn Lys Ile Val Arg
            260                 265                 270

Met Tyr Ser Pro Thr Ser Ile Leu Asp Ile Lys Gln Gly Pro Lys Glu
        275                 280                 285

Pro Phe Arg Asp Tyr Val Asp Arg Phe Phe Lys Thr Leu Arg Ala Glu
    290                 295                 300

Gln Ala Thr Gln Asp Val Lys Asn Trp Met Thr Asp Thr Leu Leu Val
305                 310                 315                 320

Gln Asn Ala Asn Pro Asp Cys Lys Thr Ile Leu Arg Ala Leu Gly Pro
                325                 330                 335

Gly Ala Thr Leu Glu Glu Met Met Thr Ala Cys Gln Gly Val Gly Gly
            340                 345                 350

Pro Ser His Lys Ala Arg Val Leu Ala Glu Ala Met Ser Gln Thr Asn
        355                 360                 365
```

```
Ser Thr Ile Leu Met Gln Arg Ser Asn Phe Lys Gly Ser Lys Arg Ile
    370                 375                 380

Val Lys Cys Phe Asn Cys Gly Lys Glu Gly His Ile Ala Arg Asn Cys
385                 390                 395                 400

Arg Ala Pro Arg Lys Gly Cys Trp Lys Cys Gly Lys Glu Gly His
                405                 410                 415

Gln Met Lys Asp Cys Thr Glu Arg Gln Ala Asn Phe Leu Gly Lys Ile
            420                 425                 430

Trp Pro Ser His Lys Gly Arg Pro Gly Asn Phe Leu Gln Ser Arg Pro
                435                 440                 445

Glu Pro Thr Ala Pro Ala Glu Ser Phe Arg Phe Glu Glu Thr Thr
    450                 455                 460

Pro Ala Pro Lys Gln Glu Pro Lys Asp Arg Glu Pro Leu Thr Ser Leu
465                 470                 475                 480

Arg Ser Leu Phe Gly Ser Asp Pro Leu Ser Gln Met Ala Pro Ile Ser
                485                 490                 495

Pro Ile Glu Thr Val Pro Val Lys Leu Lys Pro Gly Met Asp Gly Pro
            500                 505                 510

Lys Val Lys Gln Trp Pro Leu Thr Glu Glu Lys Ile Lys Ala Leu Val
    515                 520                 525

Glu Ile Cys Thr Glu Met Glu Lys Glu Gly Lys Ile Ser Lys Ile Gly
    530                 535                 540

Pro Glu Asn Pro Tyr Asn Thr Pro Ile Phe Ala Ile Lys Lys Lys Asp
545                 550                 555                 560

Ser Thr Lys Trp Arg Lys Leu Val Asp Phe Arg Glu Leu Asn Lys Arg
                565                 570                 575

Thr Gln Asp Phe Trp Glu Val Gln Leu Gly Ile Pro His Pro Ala Gly
            580                 585                 590

Leu Lys Lys Lys Lys Ser Val Thr Val Leu Ala Val Gly Asp Ala Tyr
                595                 600                 605

Phe Ser Val Pro Leu Asp Glu Asp Phe Arg Lys Tyr Thr Ala Phe Thr
    610                 615                 620

Ile Pro Ser Ile Asn Asn Glu Thr Pro Gly Ile Arg Tyr Gln Tyr Asn
625                 630                 635                 640

Val Leu Pro Gln Gly Trp Lys Gly Ser Pro Ala Ile Phe Gln Ser Ser
                645                 650                 655

Met Thr Lys Ile Leu Glu Pro Phe Arg Lys Gln Asn Pro Asp Ile Val
            660                 665                 670

Ile Tyr Gln Tyr Met Ala Ala Leu Tyr Val Gly Ser Asp Leu Glu Ile
    675                 680                 685

Gly Gln His Arg Thr Lys Ile Glu Glu Leu Arg Gln His Leu Leu Arg
    690                 695                 700

Trp Gly Phe Thr Thr Pro Asp Lys Lys His Gln Lys Glu Pro Pro Phe
705                 710                 715                 720

Leu Trp Met Gly Tyr Glu Leu His Pro Asp Lys Trp Thr Val Gln Pro
                725                 730                 735

Ile Val Leu Pro Glu Lys Asp Ser Trp Thr Val Asn Asp Ile Gln Lys
            740                 745                 750

Leu Val Gly Lys Leu Asn Trp Ala Ser Gln Ile Tyr Ala Gly Ile Lys
                755                 760                 765

Val Lys Gln Leu Cys Lys Leu Leu Arg Gly Thr Lys Ala Leu Thr Glu
    770                 775                 780
```

-continued

Val Val Pro Leu Thr Glu Glu Ala Glu Leu Glu Leu Ala Glu Asn Arg
785                 790                 795                 800

Glu Ile Leu Lys Glu Pro Val His Gly Val Tyr Tyr Asp Pro Ser Lys
        805                 810                 815

Asp Leu Ile Ala Glu Ile Gln Lys Gln Gly Gln Gly Gln Trp Thr Tyr
            820                 825                 830

Gln Ile Tyr Gln Glu Pro Phe Lys Asn Leu Lys Thr Gly Lys Tyr Ala
        835                 840                 845

Arg Met Arg Gly Ala His Thr Asn Asp Val Lys Gln Leu Thr Glu Ala
    850                 855                 860

Val Gln Lys Ile Ala Thr Glu Ser Ile Val Ile Trp Gly Lys Thr Pro
865                 870                 875                 880

Lys Phe Lys Leu Pro Ile Gln Lys Glu Thr Trp Glu Ala Trp Trp Thr
                885                 890                 895

Glu Tyr Trp Gln Ala Thr Trp Ile Pro Glu Trp Glu Phe Val Asn Thr
            900                 905                 910

Pro Pro Leu Val Lys Leu Trp Tyr Gln Leu Glu Lys Glu Pro Ile Val
        915                 920                 925

Gly Ala Glu Thr Phe Tyr Val Ala Gly Ala Ala Asn Arg Glu Thr Lys
    930                 935                 940

Leu Gly Lys Ala Gly Tyr Val Thr Asp Arg Gly Arg Gln Lys Val Val
945                 950                 955                 960

Ser Leu Thr Asp Thr Thr Asn Gln Lys Thr Ala Leu Gln Ala Ile His
                965                 970                 975

Leu Ala Leu Gln Asp Ser Gly Leu Glu Val Asn Ile Val Thr Ala Ser
            980                 985                 990

Gln Tyr Ala Leu Gly Ile Ile Gln Ala Gln Pro Asp Lys Ser Glu Ser
        995                 1000                1005

Glu Leu Val Ser Gln Ile Ile Glu Gln Leu Ile Lys Lys Glu Lys
    1010                1015                1020

Val Tyr Leu Ala Trp Val Pro Ala His Lys Gly Ile Gly Gly Asn
    1025                1030                1035

Glu Gln Val Asp Lys Leu Val Ser Arg Gly Ile Arg Lys Val Leu
    1040                1045                1050

Phe Leu Asp Gly Ile Asp Lys Ala Gln Glu Glu His Glu Lys Tyr
    1055                1060                1065

His Ser Asn Trp Arg Ala Met Ala Ser Glu Phe Asn Leu Pro Pro
    1070                1075                1080

Ile Val Ala Lys Glu Ile Val Ala Ser Cys Asp Lys Cys Gln Leu
    1085                1090                1095

Lys Gly Glu Ala Ile His Gly Gln Val Asp Cys Ser Pro Gly Ile
    1100                1105                1110

Trp Gln Leu Ala Cys Thr His Leu Glu Gly Lys Val Ile Leu Val
    1115                1120                1125

Ala Val His Val Ala Ser Gly Tyr Ile Glu Ala Glu Val Ile Pro
    1130                1135                1140

Ala Glu Thr Gly Gln Glu Thr Ala Tyr Phe Leu Leu Lys Leu Ala
    1145                1150                1155

Gly Arg Trp Pro Val Lys Thr Ile His Thr Ala Asn Gly Ser Asn
    1160                1165                1170

Phe Thr Ser Ala Thr Val Lys Ala Ala Cys Trp Trp Ala Gly Ile
    1175                1180                1185

Lys Gln Glu Phe Gly Ile Pro Tyr Asn Pro Gln Ser Gln Gly Val

```
       1190                1195                1200
Val Ala Ser Ile Asn Lys Glu Leu Lys Lys Ile Ile Gly Gln Val
       1205                1210                1215

Arg Asp Gln Ala Glu His Leu Lys Thr Ala Val Gln Met Ala Val
       1220                1225                1230

Phe Ile His Asn Phe Lys Arg Lys Gly Gly Ile Gly Glu Tyr Ser
       1235                1240                1245

Ala Gly Glu Arg Ile Val Asp Ile Ile Ala Ser Asp Ile Gln Thr
       1250                1255                1260

Lys Glu Leu Gln Lys Gln Ile Thr Lys Ile Gln Asn Phe Arg Val
       1265                1270                1275

Tyr Tyr Arg Asp Ser Arg Asp Pro Leu Trp Lys Gly Pro Ala Lys
       1280                1285                1290

Leu Leu Trp Lys Gly Glu Gly Ala Val Val Ile Gln Asp Asn Ser
       1295                1300                1305

Asp Ile Lys Val Val Pro Arg Arg Lys Ala Lys Ile Ile Arg Asp
       1310                1315                1320

Tyr Gly Lys Gln Met Ala Gly Asp Asp Cys Val Ala Ser Arg Gln
       1325                1330                1335

Asp Glu Asp
       1340

<210> SEQ ID NO 5
<211> LENGTH: 2055
<212> TYPE: DNA
<213> ORGANISM: Artificial Sequence
<220> FEATURE:
<223> OTHER INFORMATION: Mos1.Env DNA

<400> SEQUENCE: 5
atgcgggtga ccggcatccg aagaactac cagcacctgt ggcggtgggg caccatgctg      60
ctgggcatcc tgatgatttg ctctgccgcc ggaaagctgt gggtgaccgt gtactacggc     120
gtgcccgtgt ggaaagaggc caccaccacc ctgttctgcg ccagcgacgc caaggcctac    180
gacaccgagg tgcacaacgt gtgggccacc cacgcctgcg tgcccaccga ccccaacccc    240
caggaagtgg tcctggaaaa cgtgaccgag aacttcaaca tgtggaagaa caacatggtg    300
gagcagatgc acgaggacat catcagcctg tgggaccaga gcctgaagcc ctgcgtgaag    360
ctgacccccc tgtgcgtgac cctgaactgc accgacgacg tgcggaacgt gaccaacaac    420
gccaccaaca ccaacagcag ctggggcgag cctatggaaa agggcgagat caagaactgc    480
agcttcaaca tcaccaccct catccggaac aaggtgcaga agcagtacgc cctgttctac    540
aagctggacg tggtgcccat cgacaacgac agcaacaaca ccaactaccg gctgatcagc    600
tgcaacacca gcgtgatcac ccaggcctgc cccaaggtgt ccttcgagcc catccccatc    660
cactactgcg cccctgccgg cttcgccatc ctgaagtgca acgacaagaa gttcaacggc    720
accggcccct gcaccaacgt gagcaccgtg cagtgcaccc acggcatccg gcccgtggtg    780
tccacccagc tgctgctgaa cggcagcctg gccgaggaag aggtggtgat cagaagcgag    840
aatttcacca caaatgccaa gaccatcatg gtgcagctga acgtgagcgt ggagatcaac    900
tgcacccggc ccaacaacaa cacccggaag agcatccaca tcggccctgg cagggccttc    960
tacacagccg cgacatcat cggcgacatc cggcaggccc actgcaacat cagccgggcc   1020
aactggaaca cacccctgcg gcagatcgtg gagaagctgg gcaagcagtt cggcaacaac   1080
aagaccatcg tgttcaacca gcagcggcc ggagaccccg agatcgtgat gcacagcttc   1140
```

```
aactgtggcg gcgagttctt ctactgcaac agcaccaagc tgttcaacag cacctggacc   1200
tggaacaact ccacctggaa taacaccaag cggagcaacg acaccgaaga gcacatcacc   1260 ctgcccctgcc ggatcaagca gattatcaat atgtggcagg aggtcggcaa ggccatgtac  1320
gcccctccca tccggggcca gatccggtgc agcagcaaca tcaccggcct gctgctgacc   1380
cgggacggcg gcaacgatac cagcggcacc gagatcttcc ggcctggcgg cggagatatg   1440
cgggacaact ggcggagcga gctgtacaag tacaaggtgg tgaagatcga gcccctgggc   1500
gtggctccca ccaaggccaa gcggcgggtg gtgcagagcg agaagagcgc cgtgggcatc   1560
ggcgccgtgt ttctgggctt cctgggagcc gccggaagca ccatgggagc cgccagcatg   1620
accctgaccg tgcaggcccg gctgctgctg tccggcatcg tgcagcagca gaacaacctg   1680
ctccgggcca tcgaggccca gcagcacctg ctgcagctga ccgtgtgggg catcaagcag   1740
ctgcaggcca gggtgctggc cgtggagaga tacctgaagg atcagcagct cctggggatc   1800
tggggctgca gcggcaagct gatctgcacc accaccgtgc cctggaacgc cagctggtcc   1860
aacaagagcc tggacaagat ctggaacaat atgacctgga tggaatggga gcgcgagatc   1920
aacaattaca ccagcctgat ctacaccctg atcgaggaaa gccagaacca gcaggaaaag   1980
aacgagcagg aactgctgga actggacaag tgggccagcc tgtggaactg gttcgacatc   2040
agcaactggc tgtgg                                                   2055

<210> SEQ ID NO 6
<211> LENGTH: 2052
<212> TYPE: DNA
<213> ORGANISM: Artificial Sequence
<220> FEATURE:
<223> OTHER INFORMATION: Mos2.Env DNA

<400> SEQUENCE: 6
atgagagtgc ggggcatcca gcggaactgg ccccagtggt ggatctgggg catcctgggc    60
ttttggatga tcatcatctg ccgggtgatg ggcaacctgt gggtgaccgt gtactacggc   120
gtgcccgtgt ggaaagaggc caagaccacc ctgttctgcg ccagcgacgc caaggcctac   180
gagaaagagg tgcacaacgt gtgggccacc cacgcctgcg tgcccaccga ccccaacccc   240
caggaaatgg tcctgaaaaa cgtgaccgag aacttcaaca tgtggaagaa cgacatggtg   300
gaccagatgc acgaggacat catccggctg tgggaccaga gcctgaagcc ctgcgtgaag   360
ctgacccccc tgtgcgtgac cctggaatgc ggaacgtga gaaacgtgag cagcaacggc   420
acctacaaca tcatccacaa cgagacctac aaagagatga gaactgcag cttcaacgcc   480 accaccgtgg tggaggaccg gaagcagaag gtgcacgccc tgttctaccg gctggacatc   540
gtgcccctgg acgagaacaa cagcagcgag aagtccagcg agaacagctc cgagtactac   600
cggctgatca actgcaacac cagcgccatc acccaggcct gccccaaggt gtccttcgac   660
cccatcccca tccactactg cgcccctgcc ggctacgcca tcctgaagtg caacaacaag   720 acccttcaacg gcaccggccc ctgcaacaac gtgagcaccg tgcagtgcac ccacggcatc   780
aagcccgtgg tgtccacccca gctgctgctg aacggcagcc tggccgagga agagatcatc   840
atccggtccg agaacctgac caacaacgcc aagaccatca tcgtgcacct gaatgagacc   900
gtgaacatca cctgcacccg gcccaacaac aacacccgga gagcatccg gatcggccct   960 ggccagacct tttacgccac cggcgacatc atcggcgaca tccggcaggc ccactgcaac  1020
ctgagccggg acggctggaa caagaccctg cagggcgtga gaagaagct ggccgagcac  1080
```

-continued

| | |
|---|---|
| ttccccaata agaccatcaa cttcaccagc agcagcggcg gagacctgga aatcaccacc | 1140 |
| cacagcttca actgcagggg cgagttcttc tactgcaata cctccggcct gttcaatggc | 1200 |
| acctacatgc ccaacggcac caacagcaac agcagcagca acatcaccct gccctgccgg | 1260 |
| atcaagcaga tcatcaatat gtggcaggag gtcggcaggg ccatgtacgc ccctcccatc | 1320 |
| gccggcaata tcacctgccg gtccaacatc accggcctgc tgctgaccag ggacggcggc | 1380 |
| agcaacaacg gcgtgcctaa cgacaccgag accttccggc ctggcggcgg agatatgcgg | 1440 |
| aacaactggc ggagcgagct gtacaagtac aaggtggtgg aggtgaagcc cctgggcgtg | 1500 |
| gctcctaccg aggccaagcg gcgggtggtg gagagcgaga gagcgccgt gggcatcggc | 1560 |
| gccgtgtttc tgggcattct gggagccgcc ggaagcacca tgggagccgc cagcatcacc | 1620 |
| ctgaccgtgc aggcccggca gctgctgtcc ggcatcgtgc agcagcagag caacctgctg | 1680 |
| agagccatcg aggcccagca gcacatgctg cagctgaccg tgtggggcat caagcagctg | 1740 |
| cagacccggg tgctggccat cgagagatac ctgcaggatc agcagctcct gggcctgtgg | 1800 |
| ggctgcagcg gcaagctgat ctgcaccacc gccgtgccct ggaacaccag ctggtccaac | 1860 |
| aagagccaga ccgacatctg gacaacatg acctggatgc agtgggacaa agatcggc | 1920 |
| aactacaccg gcgagatcta caggctgctg aagagagcc agaaccagca ggaaaagaac | 1980 |
| gagaaggacc tgctggccct ggacagctgg aagaacctgt ggaactggtt cgacatcacc | 2040 |
| aactggctgt gg | 2052 |

<210> SEQ ID NO 7
<211> LENGTH: 4050
<212> TYPE: DNA
<213> ORGANISM: Artificial Sequence
<220> FEATURE:
<223> OTHER INFORMATION: Mos1.Gag-Pol DNA

<400> SEQUENCE: 7

| | |
|---|---|
| atgggagcca gagccagcgt gctgtccgga ggggagctgg accgctggga gaagatcagg | 60 |
| ctgaggcctg gagggaagaa gaagtacagg ctgaagcaca tcgtgtgggc cagcagagag | 120 |
| ctggaacggt tgccgtgaa ccctggcctg ctggaaacca gcgagggctg taggcagatt | 180 |
| ctgggacagc tgcagcccag cctgcagaca ggcagcgagg aactgcggag cctgtacaac | 240 |
| accgtggcca ccctgtactg cgtgcaccag cggatcgaga tcaaggacac caaagaagcc | 300 |
| ctggaaaaga tcgaggaaga gcagaacaag agcaagaaga agcccagca ggctgccgct | 360 |
| gacacaggca acagcagcca ggtgtccag aactaccca tcgtgcagaa catccaggga | 420 |
| cagatggtgc accaggccat cagccctcgg accctgaacg cctgggtgaa ggtggtggag | 480 |
| gaaaaggcct tcagccctga ggtgatcccc atgttctctg ccctgagcga gggagccaca | 540 |
| ccccaggacc tgaacaccat gctgaacacc gtgggagggc accaggctgc catgcagatg | 600 |
| ctgaaagaga caatcaacga ggaagctgcc gagtgggaca gggtccaccc agtgcacgct | 660 |
| ggacctatcg ctcctggcca gatgagagag cccagaggca gcgatattgc tggcaccacc | 720 |
| tccacactgc aggaacagat cggctggatg accaacaacc ctcccatccc tgtgggagag | 780 |
| atctacaagc ggtggatcat tctgggactg aacaagatcg tgcggatgta cagccctgtg | 840 |
| agcatcctgg acatcaggca gggacccaaa gagcccttca gggactacgt ggaccggttc | 900 |
| tacaagaccc tgagagccga gcaggccagc caggacgtga agaactggat gaccgagaca | 960 |
| ctgctggtgc agaacgccaa ccctgactgc aagaccatcc tgaaagccct ggacctgct | 1020 |
| gccacctgg aagagatgat gacagcctgc cagggagtgg gaggacctgg ccacaaggcc | 1080 |

```
agggtgctgg ccgaggccat gagccaggtg accaactctg ccaccatcat gatgcagaga    1140
ggcaacttcc ggaaccagag aaagaccgtg aagtgcttca actgtggcaa agagggacac    1200
attgccaaga actgcagggc tcccaggaag aaaggctgct ggaagtgcgg aaaagaaggc    1260
caccagatga aggactgcac cgagaggcag gccaacttcc tgggcaagat ctggcctagc    1320
aacaagggca ggcctggcaa cttcctgcag aacagacccg agcccaccgc tcctcccgag    1380
gaaagcttcc ggtttggcga ggaaaccacc acccctagcc agaagcagga acccatcgac    1440
aaagagatgt accctctggc cagcctgaag agcctgttcg gcaacgaccc cagcagccag    1500
atggctccca tcagcccaat cgagacagtg cctgtgaagc tgaagcctgg catggacgga    1560
cccagggtga agcagtggcc tctgaccgag gaaaagatca agccctgac agccatctgc    1620 gaggaaatgg aaaagagggg caagatcacc aagatcggac ccgagaaccc ctacaacacc    1680
cctgtgttcg ccatcaagaa gaaagacagc accaagtgga ggaaactggt ggacttcaga    1740
gagctgaaca gcggacccca ggacttctgg gaggtgcagc tgggcatccc tcaccctgct    1800
ggcctgaaga aaagaaaag cgtgaccgtg ctggctgtgg agatgcctac cttcagcgtg    1860
cctctggacg agggcttccg gaagtacaca gccttcacca tccccagcac caacaacgag    1920
acacctggca tcagatacca gtacaacgtg ctgcctcagg gctggaaagg cagccctgcc    1980
atcttccagt gcagcatgac cagaatcctg gaacccttca gagccaagaa ccctgagatc    2040
gtgatctacc agtatatggc tgccctctac gtgggcagcg acctggaaat cggacagcac    2100
agagccaaaa tcgaagaact ccgcgagcac ctgctgaagt ggggattcac caccccctgac    2160 aagaagcacc agaaagagcc tccccttcctg tggatgggct acgagctgca ccctgacaag    2220
tggaccgtgc agcccatcca gctgccagag aaggactcct ggaccgtgaa cgacatccag    2280
aaactggtcg gcaagctgaa ctgggccagc cagatctacc ctggcatcaa agtcagacag    2340
ctgtgtaagc tgctgagggg agccaaagca ctgaccgaca tcgtgcctct gacagaagaa    2400
gccgagctgg aactggccga aacagagag atcctgaaag aacccgtgca cggagtgtac    2460
tacgacccct ccaaggacct gattgccgag atccagaaac agggacacga ccagtggacc    2520
taccagatct atcaggaacc tttcaagaac ctgaaaacag gcaagtacgc caagatgcgg    2580
acagcccaca ccaacgacgt gaagcagctg accgaagccg tgcagaaaat cgccatggaa    2640
agcatcgtga tctggggaaa gacacccaag ttcaggctgc ccatccagaa agagacatgg    2700
gaaacctggt ggaccgacta ctggcaggcc acctggattc ccgagtggga gttcgtgaac    2760 accccaccccc tggtgaagct gtggtatcag ctggaaaagg accctatcgc tggcgtggag    2820
acattctacg tggctggagc tgccaacaga gagacaaagc tgggcaaggc tggctacgtg    2880
accgacagag gcagacagaa atcgtgagc ctgaccgaaa ccaccaacca gaaacagcc    2940 ctgcaggcca tctatctggc actgcaggac agcggaagcg aggtgaacat cgtgacagcc    3000
agccagtatg ccctgggcat catccaggcc agcctgaca gagcgagag cgagctggtg    3060 aaccagatca tcgagcagct gatcaagaaa gaacgggtgt acctgagctg ggtgccagcc    3120
cacaagggca tcgagggaa cgagcaggtg acaagctgg tgtccagcgg aatccggaag    3180
gtgctgttcc tggacggcat cgataaagcc caggaagagc acgagaagta ccacagcaat    3240
tggagagcca tggccagcga cttcaacctg cctcccgtgg tggccaaaga aatcgtggcc    3300
agctgcgacc agtgccagct gaaaggcgag gccatgcacg gacaggtgga ctgctccccct    3360 ggcatctggc agctggcatg cacccaccctg gaaggcaaga tcattctggt ggccgtgcac    3420
```

| | |
|---|---|
| gtggccagcg gatacatcga agccgaagtg atccctgccg agacagggca ggaaacagcc | 3480 |
| tacttcatcc tgaagctggc tggcagatgg cctgtgaagg tgatccacac agccaacggc | 3540 |
| agcaacttca cctctgctgc cgtgaaggct gcctgttggt gggctggcat tcagcaggaa | 3600 |
| tttggcatcc cctacaatcc ccagtctcag ggagtggtgg ccagcatgaa caaagagctg | 3660 |
| aagaagatca tcggacaggt cagggatcag gccgagcacc tgaaaactgc cgtccagatg | 3720 |
| gccgtgttca tccacaactt caagcggaag ggagggatcg gagggtactc tgctggcgag | 3780 |
| cggatcatcg acatcattgc caccgatatc cagaccaaag agctgcagaa acagatcatc | 3840 |
| aagatccaga acttcagggt gtactacagg gacagcaggg accccatctg gaagggacct | 3900 |
| gccaagctgc tgtggaaagg cgaaggagcc gtcgtcatcc aggacaacag cgacatcaag | 3960 |
| gtggtgccca cacggaaggt gaaaatcatc aaggactacg gcaaacagat ggctggagcc | 4020 |
| gactgtgtcg ctggcaggca ggacgaggac | 4050 |

<210> SEQ ID NO 8
<211> LENGTH: 4023
<212> TYPE: DNA
<213> ORGANISM: Artificial Sequence
<220> FEATURE:
<223> OTHER INFORMATION: Mos2.Gag-Pol DNA

<400> SEQUENCE: 8

| | |
|---|---|
| atgggagcca gagccagcat cctgcgagga gggaagctgg acaagtggga gaagatcagg | 60 |
| ctgaggcctg gagggaagaa acactacatg ctgaagcacc tggtctgggc cagcagagag | 120 |
| ctggaacggt ttgccctcaa tcctggcctg ctggaaccag cgagggctg caagcagatc | 180 |
| atcaagcagc tgcagcctgc cctgcagaca ggcaccgagg aactgcggag cctgttcaac | 240 |
| accgtggcca ccctgtactg cgtgcatgcc gagatcgaag tgagggacac caaagaagcc | 300 |
| ctggacaaga tcgaggaaga gcagaacaag agccagcaga aacccagca ggccaaagaa | 360 |
| gccgacggca aggtctccca gaactacccc atcgtgcaga acctgcaggg acagatggtg | 420 |
| caccagccca tcagccctcg acactgaat gcctgggtga aggtgatcga ggaaaaggcc | 480 |
| ttcagccctg aggtgatccc catgttcaca gccctgagcg agggagccac accccaggac | 540 |
| ctgaacacca tgctgaacac cgtgggaggg caccaggctg ccatgcagat gctgaaggac | 600 |
| accatcaacg aggaagctgc cgagtgggac aggctgcacc ctgtgcacgc tggacctgtg | 660 |
| gctcctggcc agatgagaga gcccagaggc agcgatattg ctggcaccac ctccaatctg | 720 |
| caggaacaga tcgcctggat gaccagcaac cctcccatcc tgtgggaga catctacaag | 780 |
| cggtggatca tcctgggact gaacaagatc gtgcggatgt acagccctac ctccatcctg | 840 |
| gacatcaagc agggacccaa agagcctttc agggactacg tggaccggtt cttcaagacc | 900 |
| ctgagagccg agcaggccac ccaggacgtg aagaactgga tgaccgacac cctgctggtg | 960 |
| cagaacgcca ccctgactg caagaccatc ctgagagccc tgggacctgg agccaccctg | 1020 |
| gaagagatga tgacagcctg ccaggagtg gaggacccct ctcacaaggc tagggtgctg | 1080 |
| gccgaggcca tgagccagac caacagcacc atcctgatgc agcggagcaa cttcaagggc | 1140 |
| agcaagcgga tcgtgaagtg cttcaactgt ggcaaagagg gacacattgc cagaaactgt | 1200 |
| agggcaccca ggaagaaagg ctgctggaag tgcggaaaag aaggccacca gatgaaggac | 1260 |
| tgcacccgag gcaggccaa cttcctgggc aagatctggc ctagccacaa gggcagacct | 1320 |
| ggcaacttcc tgcagagcag acccgagccc acgctcctc cagccgagag cttccggttc | 1380 |
| gaggaaacca cccctgctcc caagcaggaa cctaaggaca gagagcctct gaccagcctg | 1440 |

```
agaagcctgt tcggcagcga ccctctgagc cagatggctc ccatctcccc tatcgagaca   1500
gtgcctgtga agctgaagcc tggcatggac ggacccaagg tgaaacagtg gcctctgacc   1560
gaggaaaaga tcaaagccct ggtggagatc tgtaccgaga tggaaaaaga gggcaagatc   1620
agcaagatcg gacccgagaa cccctacaac accectatct cgccatcaa gaagaaagac   1680
agcaccaagt ggaggaaact ggtggacttc agagagctga acaagcggac ccaggacttc   1740
tgggaggtgc agctgggcat ccctcaccct gctggcctga agaaaagaa aagcgtgacc   1800
gtgctggccg tgggagatgc ctacttcagc gtgcctctgg acgaggactt cagaaagtac   1860
acagccttca ccatccccag catcaacaac agagacacctg gcatcagata ccagtacaac   1920
gtgctgcctc agggatggaa gggctctcct gcaatcttcc agagcagcat gaccaagatc   1980
ctggaaccct tccggaagca gaaccctgac atcgtgatct accagtacat ggcagccctg   2040
tacgtcggca gcgacctgga atcggacag caccggacca agatcgaaga actcaggcag   2100
cacctgctgc ggtggggatt caccacccct gacaagaagc accagaaaga gcctcccttc   2160
ctgtggatgg gctacgagct gcacccagac aagtggaccg tgcagcccat cgtgctgcct   2220
gagaaggact cctggaccgt gaacgacatc cagaaactgg tcggcaagct gaactgggcc   2280
agccagatct acgctggcat caaagtgaag cagctgtgta agtcctgag aggcaccaaa   2340
gccctgaccg aggtggtgcc actgacagag gaagccgagc tggaactggc cgagaacaga   2400
gagatcctga agaacccgt gcacggagtg tactacgacc ccagcaagga cctgattgcc   2460
gagatccaga gcagggaca gggacagtgg acctaccaga tctaccagga accccttcaag   2520
aacctgaaaa caggcaagta cgccaggatg agggagccc acaccaacga cgtcaaacag   2580
ctgaccgaag ccgtgcagaa gatcgccacc gagagcatcg tgatttgggg aaagacaccc   2640
aagttcaagc tgcccatcca gaaagagaca tgggaggcct ggtggaccga gtactggcag   2700
gccacctgga ttcccgagtg ggagttcgtg aacacccca ccctggtgaa gctgtggtat   2760
cagctggaaa agaacccat cgtgggagcc gagacattct acgtggctgg agctgccaac   2820
agagagacaa agctgggcaa ggctggctac gtgaccgaca gaggcaggca gaaagtggtg   2880
tccctgaccg ataccaccaa ccagaaaaca gccctgcagg ccatccacct ggctctgcag   2940
gactctggcc tggaagtgaa catcgtgaca gccagccagt atgccctggg catcattcag   3000
gcacagcctg acaagagcga gagcgagctg gtgtctcaga tcattgagca gctgatcaag   3060
aaagaaaagg tgtacctggc ctgggtgcca gcccacaagg ggatcggagg aacgagcag   3120
gtggacaagc tggtgtccag gggcatccgg aaggtgctgt ttctggacgg catcgacaaa   3180
gcccaggaag agcacgagaa gtaccacagc aattggagag ccatggccag cgagttcaac   3240
ctgcctccca tcgtggccaa agaaatcgtg gcctcttgcg acaagtgcca gctgaaaggc   3300
gaggccattc acggacaggt ggactgcagc ccaggcatct ggcagctggc ctgcacccac   3360
ctggaaggca aggtgatcct ggtggccgtg cacgtggcct ctggatacat cgaagccgaa   3420
gtgatccctg ccgagacagg ccaggaaaca gcctacttcc tgctgaagct ggctggcagg   3480
tggcctgtga aaaccatcca cacagccaac ggcagcaact tcacctctgc caccgtgaag   3540
gctgcctgtt ggtgggctgg cattaagcag gaatttggca tccccctacaa ccctcagtct   3600
cagggagtgg tggcctccat caacaaagag ctgaagaaga tcatcggaca ggtcagggat   3660
caggccgagc atctgaaaac agccgtccag atggccgtgt tcatccacaa cttcaagcgg   3720
aagggaggga tcggagagta ctctgctggc gagaggatcg tggacattat cgccagcgat   3780
```

```
atccagacca aagaactgca gaagcagatc acaaagatcc agaacttcag ggtgtactac    3840
agggacagca gagatcccct gtggaaggga cctgccaagc tgctgtggaa aggcgaagga    3900
gccgtcgtca tccaggacaa cagcgacatc aaggtggtgc ccagacggaa ggccaagatc    3960
atcagagact acggcaaaca gatggctggc gacgactgcg tcgcctctag gcaggacgag    4020
gac                                                                  4023
```

METHODS FOR INDUCING AN IMMUNE RESPONSE AGAINST HUMAN IMMUNODEFICIENCY VIRUS INFECTION IN SUBJECTS UNDERGOING ANTIRETROVIRAL TREATMENT

CROSS REFERENCE TO RELATED APPLICATION

This application is entitled to priority pursuant to 35 U.S.C. § 119(e) to U.S. Provisional Patent Application No. 62/383,140, filed Sep. 2, 2016, the disclosure of which is incorporated by reference herein in its entirety.

REFERENCE TO SEQUENCE LISTING SUBMITTED ELECTRONICALLY

This application contains a sequence listing, which is submitted electronically via EFS-Web as an ASCII formatted sequence listing with a file name "688097-149 Sequence Listing", creation date of Sep. 1, 2016, and having a size of 52.4 kB. The sequence listing submitted via EFS-Web is part of the specification and is herein incorporated by reference in its entirety

BACKGROUND OF THE INVENTION

Globally, an estimated 35.3 million people were living with human immunodeficiency virus (HIV) in 2012, which is an increase from previous years as a result of the wider availability of life-saving antiretroviral therapies (ART). There were 2.3 million new HIV infections globally, representing a 33% decline in the number of new infections from 3.4 million in 2001. At the same time, the number of acquired immunodeficiency syndrome (AIDS) deaths is also declining with 1.6 million AIDS deaths in 2012, down from 2.3 million in 2005. From 1996 to 2012, ART averted 6.6 million AIDS-related deaths worldwide, including 5.5 million deaths in low- and middle-income countries (UNAIDS Report on the Global AIDS Epidemic 2013). In 2012, 9.7 million people in low- and middle-income countries received ART, representing 61% of all who were eligible under the 2010 World Health Organization (WHO) HIV treatment guidelines. However, under the 2013 WHO guidelines, the HIV treatment coverage in low- and middle-income countries represented only 34% of the 28.3 million people eligible in 2013.

Despite its proven success at saving lives, there are significant challenges to initiating and maintaining ART for all of those HIV-infected patients that need it in the world. ART must be taken life-long with near perfect adherence in order to be effective. This places extreme pressure and costs on international donors and over-taxed health systems in developing countries where HIV prevalence rates are highest. Moreover, ART has both short-term and long-term side effects for users, and drug resistance rates rise as more people are on treatment for longer periods of time. Thus, alternative or complementary treatments, including a therapeutic vaccine, which could induce a true or "functional" cure of HIV infection and lessen or eliminate the need for lifelong ART for HIV infected individuals, would therefore be of great benefit.

Studies of HIV vaccine in HIV-uninfected and infected subjects suggest that a successful HIV vaccine program will need to induce immunity against the diverse strains and subtypes that are predominant in the target populations. Improving magnitude, breadth and depth of epitope coverage is thought to be a key to developing a successful T-cell based preventive HIV vaccine. Published primate data indicate that the number of epitope specific responses induced by a vaccine may be an important immune correlate of viral load control in the simian immunodeficiency virus (SIV) challenge system (Chen et al. Nat Med. (2001) 7(11), 1225-31). Strategies to accomplish this include using multivalent vaccines containing immunogens from a number of prevalent subtypes or using mosaic sequences, proteins assembled from natural sequences by in silico recombination, which are optimized for potential T-cell epitopes.

The enhancement of host-mediated clearance of residual virus represents a new additional approach to an HIV functional cure (Carcelain et al. Immunol Rev. (2013) 254 (1), 355-71). Findings of several studies have shown the importance of cellular immunity in the control of HIV reservoir size. HIV-1 Gag-specific CD8+ T cells isolated from elite controllers, but not from patients given ART, were shown to kill autologous resting CD4+ T cells in which the virus was reactivated with vorinostat. Moreover, functional anti-viral CD8 T cells are associated with reduced size of the central memory CD4 T cell reservoir in patients controlling their virus without ART. High-avidity multifunctional CD8 cytotoxic T lymphocytes (CTL) that target vulnerable regions in Gag are especially important in limiting virus diversity and reservoirs in individuals infected with HIV who have protective human leukocyte antigen (HLA) class I alleles. Therapeutic vaccines could re-stimulate CD8+ CTL to prevent or control virus relapses and re-establish latent infection in CD4+ T cells after treatment interruptions. A few therapeutic vaccine studies, such as the Ad5 HIV-1 gag vaccine (ACTG A5197 NCT00080106), and infusions of dendritic cells pulsed with inactivated HIV particles have shown transient viral suppression after treatment interruption. Eramune-02 is testing whether a deoxyribonucleic acid (DNA) prime, replication defective, recombinant adenovirus serotype-5 boost strategy, with the Vaccine Research Center's polyvalent HIV-Gag, Pol, Nef, and Env vaccine can reduce the viral reservoir in patients undergoing an ARV-intensification regimen (Katlama Lancet. (2013) 381(9883), 2109-17).

In contrast to patients who initiated ART in the course of chronic HIV infection, many patients who begin ART at the time of acute HIV infection demonstrate blunted or delayed rebound viremia after analytical treatment interruption (ATI) (Gianella et al. Antiviral therapy. (2011) 16(4), 535-45; Goujard et al. (2012) Antiviral therapy. 17(6), 1001-9; Hamlyn et al. (2012) PloS one. 7(8), e43754; Lodi et al. (2012) Archives of internal medicine. 172(16), 1252-5; Saez-Cirion et al. (2013) PLoS pathogens 9(3), e1003211). Several studies have shown sustained viremic control after treatment interruption in 5%-16% of patients initiated on ART at the time of acute infection (Gianella 2011, supra; Goujard 2012, supra; Grijsen 2012, supra; Lodi 2012, supra; Saez-Cirion 2013, supra). In these studies, factors associated with successful viremic control included shorter duration from HIV onset to ART initiation, longer duration on ART and low PBMC-associated HIV DNA (Williams et al. (2014) Elife 3, e03821).

However, ATI is not the standard of care for HIV infection. The Thai National HIV Treatment Guidelines, recently revised in 2014, now recommend lifelong ART for all persons living with HIV (PLHIV). However, the possibility of safely stopping or interrupting ART would hold great benefit both for patients, who are inconvenienced by having to take medications that require strict adherence and have a number of proven short-term and long-term toxicities, and by national health programs, which are committed to providing medications to hundreds of thousands or even millions of patients for decades to come.

Accordingly, there is a need in the art for improved methods of treating HIV-infected subjects, particularly HIV-infected subjects undergoing antiretroviral therapy (ART), such as therapeutic vaccines. Such a therapeutic vaccine preferably would improve immune responses to HIV and allow treated subjects to discontinue ART while maintaining viremic control.

BRIEF SUMMARY OF THE INVENTION

The invention relates to methods for inducing an immune response against human immunodeficiency virus (HIV) in HIV-infected subjects undergoing antiretroviral therapy (ART) with a primer vaccine of adenovirus 26 (Ad26) vectors encoding mosaic HIV antigens and a booster vaccine of modified vaccinia ankara (MVA) vectors encoding mosaic HIV antigens. Vaccine therapy using an adenovirus primer vaccine and an MVA booster vaccine according to embodiments of the invention among individuals with fully suppressed HIV can result in a measurable immune response and maintain viremic control after ART interruption.

Accordingly, one general aspect of the invention relates to a method of inducing an immune response against a human immunodeficiency virus (HIV) in an HIV-infected human subject undergoing antiretroviral therapy (ART), the method comprising:
(i) administering to the human subject a primer vaccine comprising an immunogenically effective amount of one or more adenovirus 26 (Ad26) vectors encoding one or more mosaic HIV gag, pol and/or env antigens and a pharmaceutically acceptable carrier; and
(ii) administering to the human subject a booster vaccine comprising an immunogenically effective amount of one or more modified vaccinia ankara (MVA) vectors encoding one or more mosaic HIV gag, pol and/or env antigens and a pharmaceutically acceptable carrier.

In certain embodiments, the booster vaccine is first administered at about 12-52 weeks after the primer vaccine is initially administered. In certain embodiments the booster vaccine is first administered at about 22-26 weeks, e.g. about 24 weeks, after the primer vaccine is initially administered.

In one embodiment of the invention, the primer vaccine comprises Ad26 vectors encoding one or more mosaic HIV gag, pol and/or env antigens comprising the amino acid sequences selected from the group consisting of SEQ ID NOs: 1, 3, and 4; and the booster vaccine comprises MVA vectors encoding one or more mosaic HIV gag, pol, and/or env antigens comprising the amino acid sequences selected from the group consisting of SEQ ID NOs: 1-4.

In one embodiment of the invention, the primer vaccine comprises Ad26 vectors encoding three mosaic HIV antigens having the amino acid sequences of SEQ ID NO: 1, SEQ ID NO: 3, and SEQ ID NO: 4; and the booster vaccine comprises MVA vectors encoding four mosaic HIV antigens having the amino acid sequences of SEQ ID NO: 1, SEQ ID NO: 2, SEQ ID NO: 3, and SEQ ID NO: 4.

In one embodiment of the invention, the primer vaccine is re-administered at about 10-14 weeks after the primer vaccine is initially administered; and the booster vaccine is re-administered at about 46 to 50 weeks after the primer vaccine is initially administered.

In some embodiments, the human subject initiated ART during acute HIV infection.

In a preferred embodiment of the invention, a method of inducing an immune response against a human immunodeficiency virus (HIV) in an HIV-infected human subject undergoing antiretroviral therapy (ART), wherein the human subject initiated ART during acute HIV infection comprises:
(i) administering to the human subject a primer vaccine comprising an immunogenically effective amount of one or more adenovirus 26 (Ad26) vectors encoding one or more mosaic HIV antigens comprising the amino acid sequences selected from the group consisting of SEQ ID NOs: 1, 3, and 4 and a pharmaceutically acceptable carrier; and
(ii) administering to the human subject a booster composition comprising an immunogenically effective amount of one or more MVA vectors encoding one or more mosaic HIV antigens comprising the amino acid sequences selected from the group consisting of SEQ ID NOs: 1-4 and a pharmaceutically acceptable carrier,
wherein the primer vaccine is re-administered at about 10-14 weeks after the primer vaccine is initially administered; the booster vaccine is first administered at about 22-26 weeks after the primer vaccine is initially administered; and the booster vaccine is re-administered at about 46-50 weeks after primer vaccine is initially administered.

In particular embodiments of the invention, the immunogenically effective amount of the Ad26 vectors encoding mosaic HIV antigens of SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen of SEQ ID NO: 4. In certain embodiments, the first, second, and third Ad26 vectors are administered at a total dose of about $5 \times 10^{10}$ viral particles (vp).

In other particular embodiments of the invention, the immunogenically effective amount of the MVA vectors encoding mosaic HIV antigens of SEQ ID NOs: 1, 2, 3, and 4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4. In certain embodiments, the first and second MVA vectors are administered at a total dose of about $1 \times 10^8$ plaque forming units (pfu).

In other preferred embodiments, the primer vaccine is re-administered at about 12 weeks after the primer vaccine is initially administered, the booster vaccine is first administered at about 24 weeks after the primer vaccine is initially administered, and the booster vaccine is re-administered at about 48 weeks after the primer vaccine is initially administered.

In some embodiments, the ART is discontinued at about 10-14 weeks after the last booster vaccine is administered.

In preferred embodiments, a human subject to which a primer vaccine and a booster vaccine has been administered according to the invention, maintains viral suppression for at least 24 weeks after discontinuing ART.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or," a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means a human, who will be or has been treated by a method according to an embodiment of the invention.

The invention relates to methods of priming and boosting an immune response against human immunodeficiency virus (HIV) in an HIV-infected human subject undergoing anti-retroviral treatment (ART). According to embodiments of the invention, a primer vaccine and a booster vaccine are administered to the HIV-infected human subject, wherein the primer vaccine comprises an immunogenically effective amount of one or more adenovirus 26 (Ad26) vectors encoding one or more mosaic HIV gag, pol, and/or env antigens; and the booster vaccine comprises an immunogenically effective amount of one or more modified vaccinia ankara (MVA) vectors encoding one or more mosaic HIV gag, pol, and/or env antigens.

Human Immunodeficiency Virus (HIV)

Human immunodeficiency virus (HIV) is a member of the genus Lentivirinae, which is part of the family of Retroviridae. Two species of HIV infect humans: HIV-1 and HIV-2. HIV-1 is the most common strain of HIV virus, and is known to be more pathogenic than HIV-2. As used herein, the terms "human immunodeficiency virus" and "HIV" refer, but are not limited to, HIV-1 and HIV-2. In certain exemplary embodiments, the envelope proteins described herein refer to those present on HIV-1 or HIV-2, preferably on HIV-1.

HIV is categorized into multiple clades with a high degree of genetic divergence. As used herein, the term "HIV clade" or "HIV subtype" refers to related human immunodeficiency viruses classified according to their degree of genetic similarity. There are currently three groups of HIV-1 isolates: M, N and O. Group M (major strains) consists of at least ten clades, A through J. Group O (outer strains) can consist of a similar number of clades. Group N is a new HIV-1 isolate that has not been categorized in either group M or O.

According to embodiments of the invention, the methods described herein can be used to induce an immune response against one or more clades of HIV.

HIV Antigens

As used herein, the terms "HIV antigen," "antigenic polypeptide of an HIV," "HIV antigenic polypeptide," "HIV antigenic protein," "HIV immunogenic polypeptide," and "HIV immunogen" all refer to a polypeptide capable of inducing an immune response, e.g., a humoral and/or cellular mediated response, against HIV in a subject. The HIV antigen can be a protein of HIV, a fragment or epitope thereof, or a combination of multiple HIV proteins or portions thereof, that can induce an immune response against HIV in a subject. An HIV antigen is capable of raising in a host a protective immune response, e.g., inducing an immune response against a viral disease or infection, and/or producing an immunity in (i.e., vaccinates) a subject against a viral disease or infection, that protects the subject against the viral disease or infection. For example, the HIV antigen can comprise a protein or fragment(s) thereof from HIV, such as the HIV gag, pol and env gene products.

According to embodiments of the invention, the HIV antigen can be an HIV-1 or HIV-2 antigen or fragment(s) thereof. Examples of HIV antigens include, but are not limited to gag, pol, and env gene products, which encode structural proteins and essential enzymes. Gag, pol, and env gene products are synthesized as polyproteins, which are further processed into multiple other protein products. The primary protein product of the gag gene is the viral structural protein gag polyprotein, which is further processed into MA, CA, SP1, NC, SP2, and P6 protein products. The pol gene encodes viral enzymes (Pol, polymerase), and the primary protein product is further processed into RT, RNase H, IN, and PR protein products. The env gene encodes structural proteins, specifically glycoproteins of the virion envelope. The primary protein product of the env gene is gp160, which is further processed into gp120 and gp41. A heterologous nucleic acid sequence according to the invention preferably encodes a gag, env, and/or pol gene product, or portion thereof.

According to embodiments of the invention, an HIV antigen is a mosaic HIV antigen. As used herein, "mosaic antigen" refers to a recombinant protein assembled from fragments of natural sequences. The "mosaic antigen" can be computationally generated and optimized using a genetic algorithm. Mosaic antigens resemble natural antigens, but are optimized to maximize the coverage of potential T-cell epitopes found in the natural sequences, which improves the breadth and coverage of the immune response.

A "mosaic HIV antigen" according to the invention is a mosaic HIV gag, env, or pol antigen, or any portion or combination thereof, more preferably a mosaic HIV-1 gag, env, or pol antigen, or any portion or combination thereof. Mosaic HIV gag, env, and/or pol antigens are mosaic antigens comprising multiple epitopes derived from one or more of the gag, pol and env polyprotein sequences of HIV. The epitope sequences of the mosaic HIV gag, pol, and/or env antigens according to the invention resemble the sequences of the natural HIV antigens, but are optimized to present a broader possible array of T cell epitopes to improve coverage of epitopes found in circulating HIV sequences.

For example, to provide maximal coverage of potential T-cell epitopes, mosaic gag, pol, and env antigens are designed to provide optimal coverage of one or more HIV clades. Sequence Database in silico recombinant sequences of fragments of 9 contiguous amino acids (9-mers) are selected that resemble real proteins and that maximize the number of 9-mer sequence matches between vaccine candidates and the global database. The mosaic HIV gag, pol, and env antigens have similar domain structure to natural antigens and consist entirely of natural sequences with no artificial junctions. The pol antigens can contain mutants to eliminate catalytic activity. The monomeric env gp140 mosaic antigens can contain point mutations to eliminate cleavage and fusion activity.

In one embodiment, a mosaic HIV antigen is a mosaic HIV gag antigen comprising epitopes derived from the sequences of gag gene products; a mosaic HIV pol antigen comprising epitopes derived from the sequences of pol gene products; or a mosaic HIV env antigen comprising epitopes derived from the sequences of env gene products.

In other embodiments, a mosaic HIV antigen according to the invention comprises a combination of epitopes derived from sequences of gag, pol, and/or env gene products. Illustrative and non-limiting examples include mosaic env-pol antigens with epitopes derived from the sequences of env and pot gene products; mosaic env-gag antigens with epitopes derived from the sequences of env and gag gene products; mosaic gag-pol antigens with epitopes derived from the sequences of gag and pol gene products; and mosaic gag-env antigens with epitopes derived from the sequences of gag and env gene products.

According to embodiments of the invention, the mosaic HIV gag, pol, and/or env antigens can comprise a combination of epitopes derived from sequences of gag, pol, and env gene products from one or more clades.

Examples of mosaic HIV Gag-Pol-Env antigens include those described in, e.g., US20120076812, Barouch et al., *Nat Med* 2010, 16:319-323; Barouch et al., *Cell* 155:1-9, 2013, all of which are incorporated herein by reference in their entirety. In certain embodiments of the invention, the mosaic HIV antigens encoded by the vectors comprise the amino acid sequences selected from the group consisting of SEQ ID NOs: 1-4. Alternative and/or additional HIV antigens could be encoded by the primer vaccine and/or the booster vaccine of the invention in certain embodiments, e.g. to further broaden the immune response.

In view of the present disclosure, a mosaic HIV antigen can be produced using methods known in the art. See, e.g., US20120076812, Fischer et al, *Nat Med,* 2007. 13(1): p. 100-6; Barouch et al., *Nat Med* 2010, 16:319-323, all of which are incorporated herein by reference in their entirety.

Adenovirus Vector

Primer vaccines used in the methods of the invention comprise one or more adenovirus vectors, particularly human adenovirus 26 vectors encoding one more HIV antigens, e.g., mosaic HIV antigens, for instance mosaic HIV gag, pol, and/or env antigens. As used herein, the notation "rAd" means recombinant adenovirus, e.g., "rAd26" refers to recombinant human adenovirus 26.

An advantage of human adenovirus serotype 26 is a low seroprevalence and/or low pre-existing neutralizing antibody titers in the human population. In some embodiments, the adenovirus vector is a replication deficient recombinant viral vector, such as a replication deficient recombinant adenovirus 26 vector.

An "adenovirus capsid protein" refers to a protein on the capsid of an adenovirus (e.g., Ad26 vectors) that is involved in determining the serotype and/or tropism of a particular adenovirus. Adenoviral capsid proteins typically include the fiber, penton and/or hexon proteins. An rAd26 vector comprises at least the hexon of Ad26, preferably at least the hexon and fiber of Ad26. In preferred embodiments, the hexon, penton and fiber are of Ad26. Preferably, also the non-capsid proteins are from Ad26.

In certain embodiments, the recombinant adenovirus vector useful in the invention is derived mainly or entirely from Ad26 (i.e., the vector is rAd26). In some embodiments, the adenovirus is replication deficient, e.g., because it contains a deletion in the E1 region of the genome. For the adenoviruses derived from Ad26 used in the invention, it is typical to exchange the E4-orf6 coding sequence of the adenovirus with the E4-orf6 of an adenovirus of human subgroup C such as Ad5. This allows propagation of such adenoviruses in well-known complementing cell lines that express the E1 genes of Ad5, such as for example 293 cells, PER.C6 cells, and the like (see, e.g. Havenga, et al., 2006, *J Gen Virol* 87: 2135-43; WO 03/104467). However, such adenoviruses will not be capable of replicating in non-complementing cells that do not express the E1 genes of Ad5. Thus, in certain embodiments, the adenovirus is a human adenovirus of serotype 26, with a deletion in the E1 region into which the nucleic acid encoding one or more mosaic HIV antigens has been cloned, and with an E4 orf6 region of Ad5.

The preparation of recombinant adenoviral vectors is well known in the art. Preparation of rAd26 vectors is described, for example, in WO 2007/104792 and in Abbink et al., (2007) *Virol* 81(9): 4654-63, both of which are incorporated by reference herein in their entirety. Exemplary genome sequences of Ad26 are found in GenBank Accession EF 153474 and in SEQ ID NO: 1 of WO 2007/104792.

Typically, an adenovirus vector useful in the invention is produced using a nucleic acid comprising the entire recombinant adenoviral genome (e.g., a plasmid, cosmid, or baculovirus vector).

The adenovirus vectors useful in the invention are typically replication deficient. In these embodiments, the virus is rendered replication deficient by deletion or inactivation of regions critical to replication of the virus, such as the E1 region. The regions can be substantially deleted or inactivated by, for example, inserting a gene of interest, such as a gene encoding an HIV antigen (usually linked to a promoter) within the region. In some embodiments, the vectors of the invention can contain deletions in other regions, such as the E3 region, or insertions of heterologous genes linked to a promoter within such regions. Mutations in the E3 region of the adenovirus need not be complemented by the cell line, since E3 is not required for replication.

A packaging cell line is typically used to produce sufficient amounts of adenovirus vectors for use in the invention. A packaging cell is a cell that comprises those genes that have been deleted or inactivated in a replication deficient vector, thus allowing the virus to replicate in the cell. Suitable packaging cell lines include, for example, PER.C6, 911, and HEK293.

According to embodiments of the invention, any mosaic HIV gag, pol and/or env antigen can be expressed in the adenovirus 26 vectors described herein. Optionally, the heterologous gene encoding the mosaic HIV antigen can be codon-optimized to ensure proper expression in the treated host (e.g., human). Codon-optimization is a technology widely applied in the art. Typically, the heterologous gene encoding the mosaic HIV antigen is cloned into the E1 and/or the E3 region of the adenoviral genome. Non-limiting embodiments of codon optimized nucleotide sequences encoding HIV antigens with SEQ ID NOs: 1-4, respectively, are provided herein as SEQ ID NOs: 5-8, respectively.

In a preferred embodiment of the invention, one or more adenovirus 26 (Ad26) vectors comprise nucleic acid that encodes one or more mosaic HIV env, gag, and/or pol antigens. In other preferred embodiments, the one or more Ad26 vectors encode one or more mosaic HIV antigens comprising the amino acid sequences selected from the group consisting of SEQ ID NOs: 1-4, and more preferably encode three mosaic HIV antigens having the amino acid sequences of SEQ ID NO: 1, SEQ ID NO: 3, and SEQ ID NO: 4.

The heterologous gene encoding the mosaic HIV antigen can be under the control of (i.e., operably linked to) an adenovirus-derived promoter (e.g., the Major Late Promoter), or can be under the control of a heterologous promoter. Examples of suitable heterologous promoters include the cytomegalovirus (CMV) promoter and the Rous sarcoma virus (RSV) promoter. Preferably, the promoter is located upstream of the heterologous gene encoding the mosaic HIV antigen within an expression cassette. In a preferred embodiment, the heterologous promoter is a CMV promoter.

MVA Vectors

Booster vaccines used in the methods of the invention comprise one or more Modified Vaccinia Ankara (MVA) vectors encoding one more HIV antigens, e.g., mosaic HIV antigens, for instance mosaic HIV gag, pol, and/or env antigens. MVA vectors useful in the invention utilize attenuated virus derived from MVA virus, which is characterized by the loss of their capabilities to reproductively replicate in human cell lines. The MVA vectors can express any mosaic HIV antigen known to those of skill in the art, including but not limited to the mosaic HIV antigens discussed herein, such as the mosaic HIV gag, pol, and/or env antigens.

MVA has been generated by more than 570 serial passages on chicken embryo fibroblasts of the dermal vaccinia strain Ankara (Chorioallantois vaccinia virus Ankara virus, CVA; for review see Mayr et al. (1975) *Infection* 3, 6-14) that was maintained in the Vaccination Institute, Ankara, Turkey for many years and used as the basis for vaccination of humans. However, due to the often severe post-vaccination complications associated with vaccinia viruses, there were several attempts to generate a more attenuated, safer smallpox vaccine.

During the period of 1960 to 1974, Prof. Anton Mayr succeeded in attenuating CVA by over 570 continuous passages in CEF cells (Mayr et al. (1975), *Infection* 3, 6-14). It was shown in a variety of animal models that the resulting MVA was avirulent (Mayr, A. & Danner, K. (1978), *Dev. Biol. Stand.* 41: 225-234). As part of the early development of MVA as a pre-smallpox vaccine, there were clinical trials using MVA-517 in combination with Lister Elstree (Stickl (1974), *Prev. Med.* 3: 97-101; Stickl and Hochstein-Mintzel (1971), *Munch. Med. Wochenschr.* 113: 1149-1153) in subjects at risk for adverse reactions from vaccinia. In 1976, MVA derived from MVA-571 seed stock (corresponding to the 571st passage) was registered in Germany as the primer vaccine in a two-stage parenteral smallpox vaccination program. Subsequently, MVA-572 was used in approximately 120,000 Caucasian individuals, the majority children between 1 and 3 years of age, with no reported severe side effects, even though many of the subjects were among the population with high risk of complications associated with vaccinia (Mayr et al. (1978), *Zentralbl. Bacteriol.* (B) 167: 375-390). MVA-572 was deposited at the European Collection of Animal Cell Cultures as ECACC V94012707.

As a result of the passaging used to attenuate MVA, there are a number of different strains or isolates, depending on the number of passages conducted in CEF cells. For example, MVA-572 was used in a small dose as a pre-vaccine in Germany during the smallpox eradication program, and MVA-575 was extensively used as a veterinary vaccine. MVA as well as MVA-BN lacks approximately 15% (31 kb from six regions) of the genome compared with ancestral CVA virus. The deletions affect a number of virulence and host range genes, as well as the gene for Type A inclusion bodies. MVA-575 was deposited on Dec. 7, 2000, at the European Collection of Animal Cell Cultures (ECACC) under Accession No. V00120707. The attenuated CVA-virus MVA (Modified Vaccinia Virus Ankara) was obtained by serial propagation (more than 570 passages) of the CVA on primary chicken embryo fibroblasts.

Even though Mayr et al. demonstrated during the 1970s that MVA is highly attenuated and avirulent in humans and mammals, certain investigators have reported that MVA is not fully attenuated in mammalian and human cell lines since residual replication might occur in these cells (Blanchard et al. (1998), *J. Gen. Virol.* 79:1159-116779; Carroll & Moss (1997), *Virology* 238:198-211; U.S. Pat. No. 5,185,146; 81). It is assumed that the results reported in these publications have been obtained with various known strains of MVA, since the viruses used essentially differ in their properties, particularly in their growth behavior in various cell lines. Such residual replication is undesirable for various reasons, including safety concerns in connection with use in humans.

Strains of MVA having enhanced safety profiles for the development of safer products, such as vaccines or pharmaceuticals, have been developed, for example by Bavarian Nordic. MVA was further passaged by Bavarian Nordic and is designated MVA-BNA. A representative sample of MVA-BN was deposited on Aug. 30, 2000 at the European Collection of Cell Cultures (ECACC) under Accession No. V00083008. MVA-BN is further described in WO 02/42480 (US 2003/0206926) and WO 03/048184 (US 2006/0159699), both of which are incorporated by reference herein in their entirety.

"Derivatives" or "variants" of MVA refer to viruses exhibiting essentially the same replication characteristics as MVA as described herein, but exhibiting differences in one or more parts of their genomes. For example, MVA-BN as well as a derivative or variant of MVA-BN fails to reproductively replicate in vivo in humans and mice, even in severely immune suppressed mice. More specifically, MVA-BN or a derivative or variant of MVA-BN has preferably also the capability of reproductive replication in chicken embryo fibroblasts (CEF), but no capability of reproductive replication in the human keratinocyte cell line HaCat (Boukamp et al (1988), *J. Cell Biol.* 106: 761-771), the human bone osteosarcoma cell line 143B (ECACC Deposit No. 91112502), the human embryo kidney cell line 293 (ECACC Deposit No. 85120602), and the human cervix adenocarcinoma cell line HeLa (ATCC Deposit No. CCL-2). Additionally, a derivative or variant of MVA-BN has a virus amplification ratio at least two fold less, more preferably threefold less than MVA-575 in Hela cells and HaCaT cell lines. Tests and assays for these properties of MVA variants are described in WO 02/42480 (US 2003/0206926) and WO 03/048184 (US 2006/0159699).

The term "not capable of reproductive replication" or "no capability of reproductive replication" is, for example, described in WO 02/42480, which also teaches how to obtain MVA having the desired properties as mentioned above. The term applies to a virus that has a virus amplification ratio at 4 days after infection of less than 1 using the assays described in WO 02/42480 or in U.S. Pat. No. 6,761,893, both of which are incorporated by reference herein in their entirety.

The term "fails to reproductively replicate" refers to a virus that has a virus amplification ratio at 4 days after infection of less than 1. Assays described in WO 02/42480 or in U.S. Pat. No. 6,761,893 are applicable for the determination of the virus amplification ratio.

The amplification or replication of a virus is normally expressed as the ratio of virus produced from an infected cell (output) to the amount originally used to infect the cell in the first place (input), and is referred to as the "amplification ratio." An amplification ratio of "1" defines an amplification status where the amount of virus produced from the infected cells is the same as the amount initially used to infect the cells, meaning that the infected cells are permissive for virus infection and reproduction. In contrast, an amplification ratio of less than 1, i.e., a decrease in output compared to the input level, indicates a lack of reproductive replication and therefore attenuation of the virus.

The advantages of MVA-based vaccine include their safety profile as well as availability for large scale vaccine production. Furthermore, in addition to its efficacy, the feasibility of industrial scale manufacturing can be beneficial. Additionally, MVA-based vaccines can deliver multiple heterologous antigens and allow for simultaneous induction of humoral and cellular immunity.

MVA vectors useful for the invention can be prepared using methods known in the art, such as those described in WO/2002/042480, WO/2002/24224, US20110159036, U.S. Pat. No. 8,197,825, etc., the relevant disclosures of which are incorporated herein by references.

In another aspect, replication deficient MVA viral strains can also be suitable for use in the invention, such as strains MVA-572 and MVA-575, or any other similarly attenuated MVA strain. Also suitable can be a mutant MVA, such as the deleted chorioallantois vaccinia virus Ankara (dCVA). A dCVA comprises del I, del II, del III, del IV, del V, and del VI deletion sites of the MVA genome. The sites are particularly useful for the insertion of multiple heterologous sequences. The dCVA can reproductively replicate (with an amplification ratio of greater than 10) in a human cell line (such as human 293, 143B, and MRC-5 cell lines), which then enable the optimization by further mutation useful for a virus-based vaccination strategy (see, e.g., WO 2011/092029).

In a preferred embodiment of the invention, the one or more MVA vectors comprise a nucleic acid that encodes one or more mosaic HIV env, gag, and/or pol antigens. In other preferred embodiments, the one or more MVA vectors encode one or more mosaic HIV antigens comprising the amino acid sequences selected from the group consisting of SEQ ID NOs: 1-4, and more preferably encode four mosaic HIV antigens having the amino acid sequences of SEQ ID NO: 1, SEQ ID NO: 2, SEQ ID NO: 3, and SEQ ID NO: 4.

Nucleic acid sequences encoding the mosaic HIV antigens can be inserted into one or more intergenic regions (IGR) of the MVA. In certain embodiments, the IGR is selected from IGR07/08, IGR 44/45, IGR 64/65, IGR 88/89, IGR 136/137, and IGR 148/149. In certain embodiments, less than 5, 4, 3, or 2 IGRs of the recombinant MVA comprise heterologous nucleotide sequences encoding an HIV antigen, such as a mosaic HIV antigen. The heterologous nucleotide sequences can, additionally or alternatively, be inserted into one or more of the naturally occurring deletion sites, in particular into the main deletion sites I, II, III, IV, V, or VI of the MVA genome. In certain embodiments, less than 5, 4, 3, or 2 of the naturally occurring deletion sites of the recombinant MVA comprise heterologous nucleotide sequences encoding mosaic HIV antigens.

The number of insertion sites of MVA comprising heterologous nucleotide sequences encoding HIV antigens can be 1, 2, 3, 4, 5, or more. In certain embodiments, the heterologous nucleotide sequences are inserted into 4, 3, 2, or fewer insertion sites. Preferably, two insertion sites are used. In certain embodiments, three insertion sites are used. Preferably, the recombinant MVA comprises at least 2, 3, 4, 5, 6, or 7 genes inserted into 2 or 3 insertion sites.

The recombinant MVA viruses provided herein can be generated by routine methods known in the art. Methods to obtain recombinant poxviruses or to insert exogenous coding sequences into a poxviral genome are well known to the person skilled in the art. For example, methods for standard molecular biology techniques such as cloning of DNA, DNA and RNA isolation, Western blot analysis, RT-PCR and PCR amplification techniques are described in Molecular Cloning, A laboratory Manual (2nd Ed.) (J. Sambrook et al., Cold Spring Harbor Laboratory Press (1989)), and techniques for the handling and manipulation of viruses are described in Virology Methods Manual (B. W. J. Mahy et al. (eds.), Academic Press (1996)). Similarly, techniques and know-how for the handling, manipulation and genetic engineering of MVA are described in Molecular Virology: A Practical Approach (A. J. Davison & R. M. Elliott (Eds.), The Practical Approach Series, IRL Press at Oxford University Press, Oxford, UK (1993) (see, e.g., Chapter 9: Expression of genes by Vaccinia virus vectors)) and Current Protocols in Molecular Biology (John Wiley & Son, Inc. (1998) (see, e.g., Chapter 16, Section IV: Expression of proteins in mammalian cells using vaccinia viral vector)).

For the generation of the various recombinant MVAs disclosed herein, different methods can be applicable. The DNA sequence to be inserted into the virus can be placed into an *E. coli* plasmid construct into which DNA homologous to a section of DNA of the MVA has been inserted. Separately, the DNA sequence to be inserted can be ligated to a promoter. The promoter-gene linkage can be positioned in the plasmid construct so that the promoter-gene linkage is flanked on both ends by DNA homologous to a DNA sequence flanking a region of MVA DNA containing a non-essential locus. The resulting plasmid construct can be amplified by propagation within *E. coli* bacteria and isolated. The isolated plasmid containing the DNA gene sequence to be inserted can be transfected into a cell culture, e.g., of chicken embryo fibroblasts (CEFs), at the same time the culture is infected with MVA. Recombination between homologous MVA DNA in the plasmid and the viral genome, respectively, can generate an MVA modified by the presence of foreign DNA sequences.

According to a preferred embodiment, a cell of a suitable cell culture such as, e.g., CEF cells, can be infected with a poxvirus. The infected cell can be, subsequently, transfected with a first plasmid vector comprising a foreign or heterologous gene or genes, preferably under the transcriptional control of a poxvirus expression control element. As explained above, the plasmid vector also comprises sequences capable of directing the insertion of the exogenous sequence into a selected part of the poxviral genome. Optionally, the plasmid vector also contains a cassette comprising a marker and/or selection gene operably linked to a poxviral promoter.

Suitable marker or selection genes are, e.g., the genes encoding the green fluorescent protein, β-galactosidase, neomycin-phosphoribosyltransferase or other markers. The use of selection or marker cassettes simplifies the identification and isolation of the generated recombinant poxvirus. However, a recombinant poxvirus can also be identified by PCR technology. Subsequently, a further cell can be infected with the recombinant poxvirus obtained as described above and transfected with a second vector comprising a second foreign or heterologous gene or genes. In case, this gene shall be introduced into a different insertion site of the poxviral genome, the second vector also differs in the poxvirus-homologous sequences directing the integration of the second foreign gene or genes into the genome of the poxvirus. After homologous recombination has occurred, the recombinant virus comprising two or more foreign or heterologous genes can be isolated. For introducing additional foreign genes into the recombinant virus, the steps of infection and transfection can be repeated by using the recombinant virus isolated in previous steps for infection and by using a further vector comprising a further foreign gene or genes for transfection.

Alternatively, the steps of infection and transfection as described above are interchangeable, i.e., a suitable cell can at first be transfected by the plasmid vector comprising the foreign gene and, then, infected with the poxvirus. As a further alternative, it is also possible to introduce each foreign gene into different viruses, co-infect a cell with all the obtained recombinant viruses and screen for a recombinant including all foreign genes. A third alternative is ligation of DNA genome and foreign sequences in vitro and reconstitution of the recombined vaccinia virus DNA genome using a helper virus. A fourth alternative is homologous recombination in *E. coli* or another bacterial species between a vaccinia virus genome cloned as a bacterial artificial chromosome (BAC) and a linear foreign sequence flanked with DNA sequences homologous to sequences flanking the desired site of integration in the vaccinia virus genome.

The heterologous nucleic acid encoding one or more mosaic HIV antigens can be under the control of (i.e., operably linked to) one or more poxvirus promoters. In certain embodiments, the poxvirus promoter is a Pr7.5 promoter, a hybrid early/late promoter, or a PrS promoter, a PrS5E promoter, a synthetic or natural early or late promoter, or a cowpox virus ATI promoter.

In certain embodiments, a first MVA vector expresses antigens having SEQ ID NO:1 and SEQ ID NO: 3, and a second MVA vector expresses antigens having SEQ ID NO: 2 and SEQ ID NO: 4.

Immunogenic Compositions

Immunogenic compositions are compositions comprising an immunogenically effective amount of a purified or partially purified adenovirus 26 or MVA vector for use in the invention. A vector can encode one mosaic HIV antigen or multiple mosaic HIV antigens, such as mosaic HIV gag, pol, and/or env antigens. The adenovirus 26 and MVA vectors can encode any mosaic HIV gag, pol, and/or env antigen in view of the present disclosure. The one or more mosaic HIV antigens encoded by the adenovirus 26 vector can be the same or different as the one or more mosaic HIV antigens encoded by the MVA vector. Said compositions can be formulated as a vaccine (also referred to as an "immunogenic composition"), such as a primer vaccine or a booster vaccine, according to methods well known in the art. Such compositions can include adjuvants to enhance immune responses. The optimal ratios of each component in the formulation can be determined by techniques well known to those skilled in the art in view of the present disclosure.

As used herein, "an immunogenically effective amount" or "immunologically effective amount" means an amount of a composition or vector sufficient to induce a desired immune effect or immune response in a subject in need thereof. In one embodiment, an immunogenically effective amount means an amount sufficient to induce an immune response in a subject in need thereof. In another embodiment, an immunogenically effective amount means an amount sufficient to produce immunity in a subject in need thereof, e.g., provide a therapeutic effect against a disease such as HIV infection. An immunogenically effective amount can vary depending upon a variety of factors, such as the physical condition of the subject, age, weight, health, etc. An immunogenically effective amount can readily be determined by one of ordinary skill in the art in view of the present disclosure.

As general guidance, an immunogenically effective amount when used with reference to a recombinant viral vector can range from about $10^6$ viral particles (vps) or plaque forming units (pfus) to about $10^{12}$ viral particles or plaque forming unites, for example $10^6$, $10^7$, $10^8$, $10^9$, $10^{10}$, $10^{11}$, or $10^{12}$ viral particles or plaque forming units. An immunogenically effective amount can be administered in a single composition, or in multiple compositions, such as 1, 2, 3, 4, 5, 6, 7, 8, 9, or 10 compositions (e.g., tablets, capsules or injectable), wherein the administration of the multiple tablets, capsules or injections collectively provides a subject with the immunogenically effective amount. It is also possible to administer an immunogenically effective amount to a subject, and subsequently administer another dose of an immunogenically effective amount to the same subject, in a so-called prime-boost regimen. This general concept of a prime-boost regimen is well known to the skill person in the vaccine field. Further booster administrations can optionally be added to the regimen, as needed.

In one embodiment, an immunogenic composition is a primer vaccine used for priming an immune response. According to embodiments of the invention, a primer vaccine comprises an immunogenically effective amount of one or more adenovirus 26 (Ad26) vectors encoding one or more mosaic HIV gag, pol, and/or env antigens and a pharmaceutically acceptable carrier. In some embodiments, the Ad26 vectors encode one or more mosaic HIV antigens comprising the amino acid sequences selected from the group consisting of SEQ ID NOs: 1, 3 and 4. In some embodiments, the Ad26 vectors encode three mosaic HIV antigens having the amino acid sequences of SEQ ID NO: 1, SEQ ID NO: 3, and SEQ ID NO: 4. The mosaic HIV antigens can be encoded by the same Ad26 vector or different Ad26 vector, such as one, two, three, four or more Ad26 vectors.

The immunogenically effective amount of the one or more Ad26 vectors can be about $10^8$, $10^9$, $10^{10}$, $10^{11}$, or $10^{12}$ viral particles (vps), preferably about $10^9$ to $10^{11}$ viral particles, and more preferably about $10^{10}$ viral particles, such as for instance about $0.5 \times 10^{10}$, $1 \times 10^{10}$, $2 \times 10^{10}$, $3 \times 10^{10}$, $4 \times 10^{10}$, $5 \times 10^{10}$, $6 \times 10^{10}$, $7 \times 10^{10}$, $8 \times 10^{10}$, $9 \times 10^{10}$, or $10 \times 10^{10}$ viral particles. In certain embodiments, the immunogenically effective amount is about $5 \times 10^{10}$ viral particles, such that the one or more Ad26 vectors are administered at a total dose of about $5 \times 10^{10}$ viral particles.

A primer vaccine for use in the invention can comprise one Ad26 vector, or multiple Ad26 vectors, such as 2, 3, 4, or more Ad26 vectors, encoding the same or different mosaic HIV gag, pol, and/or env antigens. Thus, an immunogenically effective amount can be from one Ad26 vector or multiple Ad26 vectors. For example, a total administered dose of about $10^8$ to $10^{12}$ viral particles, such as for instance about $5 \times 10^{10}$ viral particles, in the primer vaccine can be from three Ad26 vectors each encoding a different mosaic HIV antigen, such as those shown in SEQ ID NOs: 1, 3, and 4.

In a particular embodiment, the immunogenically effective amount of Ad26 vectors encoding SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen sequence of SEQ ID NO: 4. Preferably, the first, second, and third Ad26 vectors are administered at a total dose of about $10^{10}$-$10^{11}$ viral particles, for instance about $5 \times 10^{10}$ viral particles.

According to embodiments of the invention, when a primer vaccine comprises more than one Ad26 vector, the Ad26 vectors can be included in the composition in any ratio to achieve the desired immunogenically effective amount. As an illustrative and non-limiting example, two Ad26 vectors can be included in a ratio of about 1:2, 1:1, or 2:1; and three Ad26 vectors consisting of a first, second, and third Ad26 vector can in non-limiting exemplary embodiments be included in a ratio of about 1:1:1, 1:1:2, 1:2:1, or 2:1:1, respectively. In a particular embodiment, a primer vaccine comprises three Ad26 vectors consisting of a first, second, and third Ad26 vector encoding mosaic HIV antigens of SEQ ID NO: 1, SEQ ID NO: 3 and SEQ ID NO: 4, respectively, at a ratio of about 2:1:1.

In another embodiment, an immunogenic composition is a booster vaccine. According to embodiments of the invention, a booster vaccine comprises an immunogenically effective amount of one or more MVA vectors encoding one or more mosaic HIV gag, pol, and/or env antigens and a pharmaceutically acceptable carrier. In some embodiments, the MVA vectors encode one or more mosaic HIV antigens comprising the amino acid sequences selected from the group consisting of SEQ ID NOs: 1-4. In other embodiments, the MVA vectors encode four mosaic HIV antigens having the amino acid sequences of SEQ ID NO: 1, SEQ ID NO: 2, SEQ ID NO: 3, and SEQ ID NO: 4. The mosaic HIV antigens can be encoded by the same MVA vector, or different MVA vectors, such as one, two, three, four or more MVA vectors.

The immunogenically effective amount of the one or more MVA vectors in the booster vaccine can be about $10^6$, $10^7$, $10^8$, $10^9$, or $10^{10}$ plaque forming units (pfus), preferably about $10^7$ to $10^9$ pfus, and more preferably about $10^8$ pfus, such as for instance about $0.5 \times 10^8$, $1 \times 10^8$, $2 \times 10^8$, $3 \times 10^8$, $4 \times 10^8$, or $5 \times 10^8$ pfus. In certain embodiments, the immunogenically effective amount is about $1 \times 10^8$ pfus, such that the one or more MVA vectors are administered at a total dose of about $1 \times 10^8$ pfus.

A booster vaccine for use in the invention can comprise one MVA vector, or multiple MVA vectors, such as 2, 3, 4, or more MVA vectors, encoding the same or different mosaic HIV gag, pol, and/or env antigens. Thus, an immunogenically effective amount can be from one MVA vector or multiple MVA vectors. For example, a total administered dose of about $10^6$ to $10^{10}$ pfus, such as for instance about $1 \times 10^8$ pfus, in the booster vaccine can be from two MVA vectors each encoding different mosaic HIV antigens, such as those shown in SEQ ID NOs: 1, 2, 3, and 4.

In a particular embodiment, the immunogenically effective amount of MVA vectors encoding SEQ ID NOs: 1, 2, 3, and 4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4. Preferably, the first and second MVA vectors are administered at a total dose of about $10^8$ pfus, for instance about $1 \times 10^8$ pfus.

According to embodiments of the invention, when a booster vaccine comprises more than one MVA vector, the MVA vectors can be included in the composition in any ratio to achieve the desired immunogenically effective amount. As an illustrative and non-limiting example, two MVA vectors can be included in a ratio of about 1:2, 1:1, or 2:1. In a particular embodiment, a primer vaccine comprises two MVA vectors consisting of a first MVA vector encoding mosaic HIV antigens of SEQ ID NOs: 1 and 3, and a second MVA vector encoding mosaic HIV antigens of SEQ ID NOs: 2 and 4 at a ratio of about 1:1.

The preparation and use of immunogenic compositions are well known to those of ordinary skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can also be included. The immunogenic compositions used in the invention, e.g., primer vaccines and booster vaccines, can be formulated for administration according to any method known in the art in view of the present disclosure, and are preferably formulated for intramuscular administration.

In addition to the adenovirus 26 or MVA vectors encoding the one or more mosaic HIV gag, pol, and/or env antigens, the priming and/or boosting immunizations can comprise other antigens. The other antigens used in combination with the adenovirus 26 and/or MVA vectors are not critical to the invention and can be, for example, other HIV antigens and nucleic acids expressing them.

The immunogenic compositions useful in the invention can further optionally comprise adjuvants. Adjuvants suitable for co-administration in accordance with the invention should be ones that are potentially safe, well tolerated and effective in people. Non-limiting examples include QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Aluminium salts such as Aluminium Phosphate (e.g. AdjuPhos) or Aluminium Hydroxide, and MF59.

The immunogenic compositions used for priming and boosting an immune response according to embodiments of the invention comprise a pharmaceutically acceptable carrier, such as a pharmaceutically acceptable excipient, carrier, buffer, stabilizer or other materials well known to those skilled in the art. Such materials should be non-toxic and should not interfere with the efficacy of the active ingredient. The precise nature of the carrier or other material can depend on the route of administration, e.g., intramuscular, subcutaneous, oral, intradermal, cutaneous, intramucosal (e.g., gut), intranasal or intraperitoneal routes. Preferably, the pharmaceutically acceptable carrier included in the primer and booster vaccines is suitable for intramuscular administration.

Method of Inducing an Immune Response

The invention provides a method of priming and boosting an immune response against a human immunodeficiency virus (HIV) in an HIV-infected subject undergoing antiretroviral therapy using an adenovirus primer vaccine in combination with an MVA booster vaccine. The methods of priming and boosting an immune response according to embodiments of the invention are effective to induce an immune response against one or multiple clades of HIV.

In one general aspect, a method of inducing an immune response against a human immunodeficiency virus (HIV) in an HIV-infected human subject undergoing antiretroviral therapy (ART) comprises:

(i) administering to the human subject a primer vaccine comprising an immunogenically effective amount of one or more Ad26 vectors encoding one or more mosaic HIV gag, pol and/or env antigens and a pharmaceutically acceptable carrier; and (ii) administering to the human subject a booster vaccine comprising an immunogenically effective amount of one or more MVA vectors encoding one or more mosaic HIV gag, pol and/or env antigens and a pharmaceutically acceptable carrier.

In certain embodiments, the booster vaccine is first administered at about 12-52 weeks, e.g. about 16-32, e.g. about 22-26, e.g. about 24 weeks, after the primer vaccine is initially administered. One of ordinary skill in the art will be able to vary the exact timing of the priming and boosting vaccines, frequency of administration thereof, dosage thereof, etc., based upon the teachings herein and clinical experience.

Any of the primer and booster vaccine compositions described herein can be used in a method of inducing an immune response against HIV according to the invention. Embodiments of the primer vaccine; booster vaccine; Ad26 vectors; MVA vectors; mosaic HIV gag, pol and/or env antigens encoded by the Ad26 and MVA vectors, etc. that can be used in the methods of the invention are discussed in detail above and in the illustrative examples below.

According to embodiments of the invention, "inducing an immune response" when used with reference to the methods described herein encompasses causing a desired immune response or effect in a subject in need thereof against an infection, such as HIV infection, preferably for therapeutic purposes. "Inducing an immune response" also encompasses providing a therapeutic immunity for treating against a pathogenic agent, i.e., HIV. As used herein, the term "therapeutic immunity" or "therapeutic immune response" means that the HIV infected vaccinated subject is able to control an infection with the pathogenic agent, i.e., HIV, against which the vaccination was done. In one embodiment, "inducing an immune response" refers to causing or improving cellular immunity, e.g., T cell response, against HIV infection. Typically, the administration of the primer and booster vaccine compositions according to embodiments of the invention will have a therapeutic aim to generate an immune response against HIV after HIV infection or development of symptoms characteristic of HIV infection.

The patient population for treatment according to the methods of the invention described herein is HIV-infected human subjects, particularly HIV-infected human subjects undergoing antiretroviral therapy (ART). The terms "HIV infection" and "HIV-infected" as used herein refer to invasion of a human host by HIV. As used herein, "an HIV-infected human subject" refers to a human subject in whom HIV has invaded and subsequently replicated and propagated within the human host, thus causing the human host to be infected with HIV or have an HIV infection or symptoms thereof.

As used herein, "undergoing antiretroviral therapy" refers to a human subject, particularly an HIV-infected human subject, that is being administered, or who has initiated treatment with antiretroviral drugs. According to embodiments of the invention, the antiretroviral therapy (ART) is started prior to the first administration of the primer vaccine, for instance, about 2 to 6 weeks prior, such as about 2, 3, 4, 5, or 6 weeks prior, or 2-24 months prior, such as about 2, 3, 5, 6, 8, 12, 16, 20 or 24 months prior, or longer. In certain embodiments the ART is started about 4 weeks prior to the first administration of the primer vaccine. In a subject undergoing antiretroviral therapy, the antiretroviral therapy is continued during administration of the prime/boost vaccine regimen of the invention.

In certain embodiments, a human subject undergoing antiretroviral therapy is on current stable ART for at least four weeks and has plasma HIV ribonucleic acid (RNA) levels at less than 50 copies/mL for at least 24 weeks to at least 52 weeks, and preferably at least 48 weeks prior to initiation of a prime/boost vaccine regimen according to the invention. However, the human subject can have one or more blips (i.e., instances) of plasma HIV RNA greater than 50 copies/ml to less than 200 copies/ml within this period, such as within the 48 week period prior to the initiation of a prime/boost vaccine regimen, provided that screening immediately prior to initiation of the prime/boost vaccine regimen is less than 50 copies/ml.

In a preferred embodiment, the subject initiated ART during acute HIV infection. The term "acute HIV infection" refers to the initial stage of HIV infection. In general, there are three stages of HIV infection: (1) acute HIV infection, (2) clinical latency, and (3) acquired immunodeficiency syndrome (AIDS). During acute HIV infection, the host typically develops symptoms such as fever, swollen glands, sore throat, rash, muscle and joint aches and pains, headache, etc., as a result of the body's natural response to the HIV infection. During the acute stage of infection, large amounts of the HIV virus are produced in the host, and CD4 levels can decrease rapidly, because the HIV uses CD4 to replicate and then subsequently destroys the CD4. Once the natural immune response of the host brings the level of HIV in the host to a stable level, also known as viral set point, CD4 count begins to increase, but likely not to pre-infection levels. Acute HIV infection is also characterized as Fiebig stages I, II, III, and IV.

Acute HIV infection is typically within two to four weeks after a host is exposed to and infected with HIV and continues for an additional two to four weeks. The acute HIV infection stage lasts until the host creates its own antibodies against HIV, at which point the clinical latency stage begins. During the clinical latency stage, HIV is living or developing in the host without causing any symptoms, or only causing mild symptoms. HIV reproduces at very low levels during the clinical latency stage, although the HIV is still active. The clinical latency stage is sometimes also referred to as 'chronic HIV infection' or 'asymptomatic HIV infection'. In certain embodiments of the invention, the subject initiated ART within 4, preferably 3, more preferably 2 weeks of diagnosis of primary HIV infection.

According to embodiments of the invention, a subject who initiates ART during acute HIV infection begins treatment with antiretroviral drugs at about 2 weeks to about 8 weeks after being exposed to and infected with HIV, such as about 2, 3, 4, 5, 6, 7, or 8 weeks after exposure and infection. Subjects who began ART during acute HIV infection and have plasma HIV RNA levels of less than 50 copies/mol for at least 24 weeks, preferably at least 48 weeks, have low HIV viral reservoirs and therefore have a high chance for maintained viral suppression in the absence of ART, i.e., HIV remission.

A subject undergoing ART can be administered or treated with any antiretroviral drugs known in the art in view of the present disclosure. ART are medications that treat HIV, although the drugs do not kill or cure the virus. However, when taken in combination they can prevent the growth of the virus. When the virus is slowed down, so is HIV disease. Antiretroviral drugs are referred to as ARV. Combination ARV therapy (cART) is referred to as highly active ART (HAART). One of ordinary skill in the art will be able to determine the appropriate antiretroviral treatment, frequency of administration, dosage of the ART, etc. so as to be compatible with simultaneous administration of the Ad26 prime/MVA boost vaccine regimens of the invention. Examples of antiretroviral drugs used for ART include, but are not limited to nucleoside reverse transcriptase inhibitors (NRTIs, non-limiting examples of which include zidovudine, didanosine, stavudine, lamivudine, abacavir, tenofovir, combivir [combination of zidovudine and lamivudine], trizivir [combination of zidovudine, lamivudine and abacavir], emtricitabine, truvada [combination of emtricitabine and tenofovir], and epzicom [combination of abacavir and lamivudine]), non-nucleoside reverse transcriptase inhibitors (NNRTIs, non-limiting examples of which include nevirapine, delavirdine, efavirenz, etravirine, and rilpivirine), protease inhibitors (PIs, non-limiting examples of which include saquinavir, indinavir, ritonavir, nelfinavir, amprenavir, lopinavir/ritonavir, atazanavir, fosamprenavir, tipranavir, darunavir), integrase inhibitors (INSTIs, non-limiting examples including raltegravir, elvitegravir, and dolutegravir), and fusion inhibitors, entry inhibitors and/or chemokine receptor antagonists (FIs, CCR5 antagonists; non-limiting examples including enfuvirtide, aplaviroc, maraviroc, vicriviroc, and cnicriviroc).

In a method of inducing an immune response against HIV according to the invention, an HIV-infected human subject undergoing ART is administered a primer vaccine at least once and a booster vaccine at least once. According to embodiments of the invention, the booster vaccine is first administered at about 22-26 weeks, such as 22, 23, 24, 25, or 26 weeks after the primer vaccine is initially administered. In certain embodiments, the booster vaccine is first administered at about 24 weeks after the primer vaccine is initially administered.

In some embodiments, the primer vaccine is re-administered after the primer vaccine is initially administered, and preferably re-administered before the booster vaccine is first administered. For example, the primer vaccine can be re-administered at about 10-14 weeks after the primer vaccine is initially administered, such as about 10, 11, 12, 13, or 14 weeks after the primer vaccine is initially administered, preferably at about 12 weeks after the primer vaccine is initially administered.

In other embodiments, the booster vaccine is re-administered after the booster vaccine is first administered. The booster vaccine can be administered at about 46 to 50 weeks, such as 46, 47, 48, 49, or 50 weeks after the primer vaccine is initially administered. In certain preferred embodiments, the booster vaccine is re-administered at about 48 weeks after the primer vaccine is initially administered.

In particular embodiments of the invention, both the primer vaccine and the booster vaccine are re-administered to the subject. The primer vaccine can be re-administered at about 10-14 weeks, such as for instance about 12 weeks after the primer vaccine is initially administered; and the booster vaccine can be re-administered at about 46 to 50 weeks, such as for instance about 48 weeks after the primer vaccine is initially administered.

Further booster administrations are possible, and embodiments of the disclosed methods also contemplate administration of such additional boosting immunizations with immunogenic compositions containing Ad26 vectors and/or MVA vectors. Any of the Ad26 vectors and MVA vectors described herein can be used in additional boosting immunizations. Preferably, any additional booster immunizations are with immunogenic compositions comprising MVA vectors encoding one or more mosaic HIV gag, pol, and env antigens, such as those comprising the amino acid sequences of SEQ ID NOs: 1-4.

The primer and booster vaccine compositions can be administered by any method known in the art in view of the present disclosure, and administration is typically via intramuscular, intradermal or subcutaneous administration, preferably intramuscular. Intramuscular administration can be achieved by using a needle to inject a suspension of the adenovirus and/or MVA vectors. An alternative is the use of a needleless injection device to administer the composition (using, e.g., Biojector™) or a freeze-dried powder containing the vaccine.

Other modes of administration, such as intravenous, cutaneous, intradermal or nasal are also envisaged as well. For intravenous, cutaneous or subcutaneous injection, the vector will be in the form of a parenterally acceptable aqueous solution which is pyrogen-free and has suitable pH, isotonicity and stability. Those of ordinary skill in the art are well able to prepare suitable solutions using, for example, isotonic vehicles such as Sodium Chloride Injection, Ringer's Injection, and Lactated Ringer's Injection. Preservatives, stabilizers, buffers, antioxidants and/or other additives can be included, as required. A slow-release formulation can also be employed.

In one exemplary regimen, the primer vaccine comprising one or more adenovirus 26 vectors is administered (e.g., intramuscularly) in an amount of about 100 µl to about 2 ml, preferably about 0.5 ml, of saline solution containing concentrations of about $10^8$ to $10^{12}$ virus particles/ml. The initial primer vaccination is followed by a boost as described above. The booster vaccine comprising one more MVA vectors is administered (e.g., intramuscularly) in an amount of about 100 µl to about 2 ml, preferably about 0.5 ml, of saline solution containing concentrations of about $10^6$ to $10^9$ particle forming units/ml. The skilled artisan will appreciate that certain factors may influence the dosage required to effectively treat a subject, including but not limited to the severity of the disease or disorder, previous treatments, the general health and/or age of the subject, and other diseases present.

In preferred embodiments, subjects undergo interruption (also referred to as discontinuation, used interchangeably herein) of ART after completion of the vaccine regimen according to embodiments of the invention. In some embodiments, subjects can undergo antiretroviral analytical treatment interruption (ARV ATI) after completion of vaccine regimen according to embodiments of the invention. "Antiretroviral analytical treatment interruption" and "ARV ATI" as used in the invention refer to discontinuation of treatment with antiretroviral drugs in order to assess viral suppression and viremic control in the absence of continued ART. Typically, subjects can undergo ARV ATI, i.e., ART can be discontinued, when the subject has plasma HIV RNA levels at less than 50 copies/mL for at least about 52 weeks, but a subject can still undergo ARV ATI even if the subject has one or more blips (i.e., instances) of plasma HIV RNA greater than 50 copies/ml to less than 200 copies/ml within this period, provided that the screening immediately prior to ARV ATI shows less than 50 copies/ml of plasma HIV RNA.

According to embodiments of the invention, the ART can be stopped at about 10-14 weeks, such as 10, 11, 12, 13, or 14 weeks after the last booster vaccine is administered. In certain embodiments, the last booster vaccine is administered at about 46-50 weeks after the primer vaccine is initially administered. In these embodiments, the ART can be stopped at about 58 to 62 weeks, such as 58, 59, 60, 61, or 62 weeks after the primer vaccine is initially administered, and preferably about 60 weeks after the primer vaccine is initially administered. In other embodiments, for subjects who are on non-nucleoside reverse transcriptase inhibitor (NNRTI)-based ART, a boosted protease inhibitor can be administered in place of the NNRTI for about 1-2 weeks prior to stopping ART to reduce the risk of developing NNRTI resistance. It is also possible to administer an activator (e.g. a histone deacetylase inhibitor) during the ATI stage to activate any (e.g. latent) HIV reservoir and thereby improve the immune response.

Subjects undergoing ARV ATI can be monitored, e.g., by measuring plasma HIV RNA levels. For example, monitoring after the initiation of ARV ATI can occur up to two times per week during the first six weeks when rebound viremia is most likely to occur. "Rebound viremia" is defined as plasma HIV RNA levels of greater than 1,000 copies/ml after ARV ATI. ART can be re-initiated in subjects with rebound viremia. Preferably, a subject treated according to the methods of the invention will maintain viremic control after ART interruption. As used herein, "maintain viremic control" is defined as at least 24 weeks with plasma HIV RNA of less than 50 copies/mL after ARV ATI. The "maintained viremic control" criterion is still deemed to be met if there are one or more instances of plasma HIV RNA greater than 50 copies/ml to less than 1000 copies/ml, as long as the subject does not have plasma HIV RNA levels above 1000 copies/ml on two consecutive determinations at least one week apart.

Typically (not using the methods of the instant invention) human HIV-infected subjects have a return of viremia after 2-3 weeks following ART interruption. Without wishing to be bound by any theories, it is believed that vaccine therapy using an adenovirus primer vaccine and an MVA booster vaccine according to embodiments of the invention among individuals with fully suppressed HIV will result in a measurable immune response and maintain viremic control after ARV ATI. In some embodiments, subjects can discontinue ART after being treated according to a method of the invention. Discontinuation of ART can be for long periods of time (e.g., at least 24 weeks, preferably longer, e.g. at least about 28, 32, 36, 40, 44, 48, 52 weeks, 16 months, 18, 20, 22, 24 months, or even longer). Such periods of time in which ART is stopped or discontinued are referred to as a "holiday" or "ART holiday" or "treatment holiday". In other embodiments, vaccine therapy according to the methods of the invention can provide HIV remission, meaning that viral suppression is maintained in the absence of ART. In certain embodiments of the invention, a human subject that received the priming and boosting vaccines of the invention, discontinues ART and maintains viral suppression for at least 24 weeks after discontinuing ART.

EMBODIMENTS

Embodiment 1 is a method of inducing an immune response against a human immunodeficiency virus (HIV) in an HIV-infected human subject undergoing antiretroviral therapy (ART), the method comprising:
 (i) administering to the human subject a primer vaccine comprising an immunogenically effective amount of one or more adenovirus 26 (Ad26) vectors encoding one or more mosaic HIV gag, pol and/or env antigens and a pharmaceutically acceptable carrier; and
 (ii) administering to the human subject a booster vaccine comprising an immunogenically effective amount of one or more modified vaccinia ankara (MVA) vectors encoding one or more mosaic HIV gag, pol and/or env antigens and a pharmaceutically acceptable carrier.

Embodiment 2 is the method according to embodiment 1, wherein the booster vaccine is first administered at about 12-52 weeks after the primer vaccine is initially administered, preferably wherein the booster vaccine is first administered at about 22-26 weeks after the primer vaccine is initially administered.

Embodiment 3 is the method according to embodiment 1 or embodiment 2, wherein the primer vaccine comprises Ad26 vectors encoding one or more mosaic HIV antigens comprising the amino acid sequences selected from the group consisting of SEQ ID NOs: 1, 3 and 4; and the booster vaccine comprises one or more MVA vectors encoding one or more mosaic HIV antigens comprising the amino acid sequences selected from the group consisting of SEQ ID NOs: 1-4.

Embodiment 4 is the method according to embodiment 3, wherein the primer vaccine comprises Ad26 vectors encoding three mosaic HIV antigens having the amino acid sequences of SEQ ID NO: 1, SEQ ID NO: 3, and SEQ ID NO: 4; and the booster vaccine comprises MVA vectors encoding four mosaic HIV antigens having the amino acid sequences of SEQ ID NO: 1, SEQ ID NO: 2, SEQ ID NO: 3, and SEQ ID NO: 4.

Embodiment 5 is the method according to embodiment 4, wherein the immunogenically effective amount of the Ad26 vectors encoding mosaic HIV antigens of SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen of SEQ ID NO: 4.

Embodiment 6 is the method according to any one of embodiments 1 to 5, wherein the primer vaccine and booster vaccine are administered via intramuscular injection.

Embodiment 7 is the method according to embodiment 5, wherein the first, second, and third Ad26 vectors are administered at a total dose of about $5 \times 10^{10}$ viral particles (vp).

Embodiment 8 is the method according to embodiment 7, wherein the total dose of about $5\times10^{10}$ vps is administered intramuscularly at a volume of 0.5 ml.

Embodiment 9 is the method according to embodiment 7 or embodiment 8, wherein the first, second, and third Ad26 vectors are at a ratio of about 2:1:1, respectively.

Embodiment 10 is the method according to any one of embodiments 3-5, wherein the immunogenically effective amount of the MVA vectors encoding mosaic HIV antigens of SEQ ID NOs: 1, 2, 3, and 4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4.

Embodiment 11 is the method according to embodiment 10, wherein the first and second MVA vectors are administered at a total dose of about $1\times10^8$ plaque forming units (pfus).

Embodiment 12 is the method according to embodiment 11, wherein the total dose of about $1\times10^8$ pfus is administered intramuscularly at a volume of 0.5 ml.

Embodiment 13 is the method according to embodiment 11 or embodiment 12, wherein the first and second MVA vectors are at a ratio of about 1:1.

Embodiment 14 is the method according to any one of claims 1 to 13, further comprising re-administering the primer vaccine at about 10-14 weeks after the primer vaccine is initially administered; and re-administering the booster vaccine at about 46 to 50 weeks after the primer vaccine is initially administered.

Embodiment 15 is the method according to embodiment 14, wherein the primer vaccine is re-administered at about 12 weeks after the primer vaccine is initially administered; the booster vaccine is first administered at about 24 weeks after the primer vaccine is initially administered; and the booster vaccine is re-administered at about 48 weeks after the primer vaccine is initially administered.

Embodiment 16 is the method according to any one of embodiments 1 to 15, wherein the human subject initiated ART during acute HIV infection.

Embodiment 17 is the method according to any one of embodiments 1 to 16, wherein a further booster vaccine is administered, and the further booster vaccine is a composition comprising an immunogenically effective amount of one or more Ad26 vectors encoding one or more mosaic HIV gag, pol and/or env antigens and a pharmaceutically acceptable carrier; or a composition comprising an immunogenically effective amount of one or more MVA vectors encoding one or more mosaic HIV gag, pol, and/or env antigens and a pharmaceutically acceptable carrier.

Embodiment 18 is the method according to embodiment 17, wherein the further booster vaccine is a composition comprising an immunogenically effective amount of one or more MVA vectors encoding one or more mosaic HIV gag, pol, and/or env antigens and a pharmaceutically acceptable carrier.

Embodiment 19 is the method according to embodiment 18, wherein the MVA vectors encode four mosaic HIV antigens having the amino acid sequences of SEQ ID NO: 1, SEQ ID NO: 2, SEQ ID NO: 3, and SEQ ID NO: 4; preferably wherein the immunogenically effective amount of the MVA vectors encoding mosaic HIV antigens of SEQ ID NOs: 1, 2, 3, and 4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4.

Embodiment 20 is the method according to any one of embodiments 1 to 19, wherein the subject is on current stable ART at least four weeks prior to the initial administration of the primer vaccine.

Embodiment 21 is the method according to any one of embodiments 1 to 20, wherein the subject has sustained viremic control defined as plasma HIV RNA of less than 50 copies per ml for at least 48 weeks prior to the initial administration of the primer vaccine, optionally with one or more blips of plasma HIV RNA greater than 50 copies/ml to less than 200 copies/ml, provided that screening immediately prior to the initial administration of the primer vaccine is less than 50 copies/ml.

Embodiment 22 is the method according to any one of embodiments 1-21, wherein the ART is discontinued at about 10-14 weeks after the last booster vaccine is administered.

Embodiment 23 is the method according to embodiment 22, wherein the ART is discontinued at about 12 weeks after the last booster vaccine is administered.

Embodiment 24 is the method according to embodiment 22 or embodiment 23, wherein the subject has sustained viremic control after discontinuing ART.

Embodiment 25 is a method of inducing an immune response against a human immunodeficiency virus (HIV) in an HIV-infected human subject undergoing antiretroviral therapy (ART), the method comprising:
(i) administering to the human subject a primer vaccine comprising an immunogenically effective amount of one or more adenovirus 26 (Ad26) vectors encoding one or more mosaic HIV antigens comprising the amino acid sequences selected from the group consisting of SEQ ID NOs: 1, 3, and 4 and a pharmaceutically acceptable carrier; and
(ii) administering to the human subject a booster vaccine comprising an immunogenically effective amount of one or more MVA vectors encoding one or more mosaic HIV antigens comprising the amino acid sequences selected from the group consisting of SEQ ID NOs: 1-4 and a pharmaceutically acceptable carrier,
wherein the primer vaccine is re-administered at about 10-14 weeks after the primer vaccine is initially administered; the booster vaccine is first administered at about 22-26 weeks after the primer vaccine is initially administered; and the booster vaccine is re-administered at about 46-50 weeks after the primer vaccine is initially administered; and
wherein the human subject initiated ART during acute HIV infection.

Embodiment 26 is the method according to embodiment 25, wherein the immunogenically effective amount of the Ad26 vectors encoding one or more mosaic HIV antigens of SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen of SEQ ID NO: 4; and wherein the immunogenically effective amount of the MVA vectors encoding one or more mosaic HIV antigens of SEQ ID NOs: 1-4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4.

Embodiment 27 is the method according to embodiment 26, wherein the first, second, and third Ad26 vectors are administered at a total dose of about $5\times10^{10}$ vp; and the first and second MVA vectors are administered at a total dose of about $1\times10^8$ pfu.

Embodiment 28 is the method according to embodiment 26 or embodiment 27, wherein the first, second, and third Ad26 vectors are at a ratio of about 2:1:1, respectively; and the first and second MVA vectors are at a ratio of about 1:1, respectively.

Embodiment 29 is the method according to any one of embodiments 25-28, wherein the primer vaccine is re-administered at about 12 weeks after the primer vaccine is initially administered, the booster vaccine is first administered at about 24 weeks after the primer vaccine is initially administered, and the booster vaccine is re-administered at about 48 weeks after the primer vaccine is initially administered.

Embodiment 30 is the method according to any one of embodiments 25-29, wherein a further booster vaccine is administered, and the further booster vaccine is a composition comprising an immunogenically effective amount of one or more MVA vectors encoding one or more mosaic HIV antigens comprising the amino acid sequences selected from the group consisting of SEQ ID NOs: 1-4 and a pharmaceutically acceptable carrier, preferably encoding four mosaic HIV antigens having the amino acid sequences of SEQ ID NO: 1, SEQ ID NO: 2, SEQ ID NO: 3, and SEQ ID NO: 4.

Embodiment 31 is the method according to any one of embodiments 25-30, wherein the primer vaccine and booster vaccine are administered intramuscularly.

Embodiment 32 is the method according to any one of embodiments 25-31, wherein the subject is on current stable ART at least four weeks prior to the initial administration of the primer vaccine.

Embodiment 33 is the method according to any one of embodiments 25-32, wherein the subject has sustained viremic control defined as plasma HIV RNA of less than 50 copies per ml for at least 48 weeks prior to the initial administration of the primer vaccine, optionally with one or more blips of plasma HIV RNA greater than 50 copies/ml to less than 200 copies/ml, provided that screening immediately prior to the initial administration of the primer vaccine is less than 50 copies/ml.

Embodiment 34 is the method according to any one of embodiments 25-33, wherein the ART is discontinued at about 10-14 weeks after the last booster vaccine is administered.

Embodiment 35 is the method according to embodiment 34, wherein the ART is discontinued at about 12 weeks after the last booster vaccine is administered.

Embodiment 36 is the method according to embodiment 34 or 35, wherein the subject has sustained viremic control after discontinuing ART.

Embodiment 37 is a method according to any one of embodiments 1-36, wherein administration of the primer vaccine and booster vaccine induces an immune response against multiple clades of HIV in the subject.

Embodiment 38 is a method according to any one of embodiments 1-37, wherein a human subject to which the primer vaccine and the booster vaccine has been administered, discontinues ART and maintains viral suppression for at least 24 weeks after discontinuing ART.

The following examples of the invention are to further illustrate the nature of the invention. It should be understood that the following examples do not limit the invention and the scope of the invention is to be determined by the appended claims.

EXAMPLES

Example 1

Study of HIV Vaccine Regimens in HIV-Infected Humans Undergoing Antiretroviral Therapy (ART)

Clinical studies in humans are conducted to investigate the effect of Ad26 vector priming immunizations and MVA vector boosting immunizations in HIV-infected human adults after antiretroviral analytical treatment interruption (ARV ATI).

Objectives

The primary objectives of the study include: (1) determining the safety and tolerability of an Ad26 primer/MVA boost vaccine regimen versus placebo in subjects on suppressive ART that was initiated during acute HIV infection; and (2) measuring the frequency and duration of sustained viremic control after receiving Ad26 prime/MVA boost or placebo, defined as greater than 24 weeks with plasma HIV RNA of less than 50 copies/ml after antiretroviral analytical treatment interruption (ARV ATI). The secondary objectives of the study include: (1) determining the immunogenicity of Ad26 prime/MVA boost vaccine regimen in subjects on suppressive ART that was initiated during acute HIV infection; (2) characterizing biomarkers of HIV reservoir at baseline, after vaccine therapy prior to ARV ATI (weeks 48-60 of the study), and after ARV ATI (weeks 60-96 of the study); (3) comparing the duration of viremic control (plasma HIV RNA less than 50 copies/ml) between vaccine and placebo recipients who failed to achieve sustained viremic control at week 24 after ARV ATI; and (4) describing the frequency, magnitude, specificity and functional capacity of humoral and cellular immune responses to vaccines.

Vaccination and Experimental Design

A single-center, randomized, parallel-group, placebo-controlled, double-blind combined Phase 1/2a clinical study in HIV-infected adults aged 18 to 50 years is performed. A target of 36 human subjects are participating in this study. The subjects in the study started on antiretroviral therapy (ART) during acute HIV infection, and are on a current stable ART for at least four weeks prior to initiation of vaccine/placebo, and have achieved absence of viremia (plasma HIV RNA of less than 50 copies/ml) for at least 48 weeks prior to initiation of vaccine/placebo. The subjects are divided into two groups: the test group (24 subjects) and the control group (12 subjects). The subjects in the test group receive the study vaccine, and the subjects in control group receive placebo.

The study continues for 96 weeks and will be carried out in two stages, including a vaccination period of 48 weeks (stage 1), a 12 week period between the final vaccination and antiretroviral analytical treatment interruption (ARV ATI) (stage 1), and a follow-up period of 36 weeks in which all antiretroviral drugs are discontinued, i.e., ARV ATI (stage 2).

Dosage and Administration

Subjects receive four doses of study vaccine: adenovirus 26 vectors encoding mosaic HIV antigens ($Ad26_{mos}$) or placebo is administered at weeks 0 and 12; and MVA vectors encoding mosaic HIV antigens ($MVA_{mos}$) or placebo is administered at Weeks 24 and 48. Study vaccines ($Ad26_{mos}$, and $MVA_{mos}$) and placebo with the administered doses are as follows:
  (i) $Ad26_{mos}$ is composed of the following three vaccine products supplied in the same vial and administered in a 2:1:1 ratio: Ad26.Mos1Env, Ad26.Mos1Gag-Pol, and Ad26.Mos2Gag-Pol expressing HIV mosaic Env1 (SEQ ID NO: 1), mosaic GagPol1 (SEQ ID: NO 3), and mosaic GagPol2 (SEQ ID NO: 4) genes, respectively; total dose is about $5 \times 10^{10}$ viral particles (vp) per 0.5 ml injection;

(ii) $MVA_{mos}$ is composed of the following two vaccine products supplied in separate vials and administered in a 1:1 ratio: MVA-Mosaic1 (MVA virus expressing Mosaic1 HIV-1 Gag, Pol, and Env proteins having SEQ ID NOs: 1 and 3) and MVA-Mosaic2 (MVA virus expressing Mosaic2 HIV-1 Gag, Pol, and Env proteins having SEQ ID NOs: 2 and 4); total dose is about $1 \times 10^8$ plaque forming units (pfu) per 0.5 ml injection; and (iii) Placebo is 0.9% sodium chloride (0.5 ml injection).

Subjects receive the study vaccines or placebo according to the schedule in Table 1 below in four doses administered by intramuscular injection. Subjects in both the test and control groups receive standard ART for HIV treatment during the first 60 weeks of the trial prior to ARV ATI. Blood and genital secretions are taken at specific clinical visits to assess immune responses (cellular and humoral immune responses) and viremic control throughout the study.

TABLE 1

Schedule for administration of study vaccines

| Group | N | Week 0 | Week 12 | Week 24 | Week 48 |
|---|---|---|---|---|---|
| Test | 24 | $Ad26_{mos}$ | $Ad26_{mos}$ | $MVA_{mos}$ | $MVA_{mos}$ |
| Control | 12 | Placebo | Placebo | Placebo | Placebo |

At week 60, all treatment with antiretroviral drugs is stopped to initiate ARV ATI (stage 2). Subjects on non-nucleoside reserve transcriptase inhibitor (NNRTI)-based antiretroviral drugs are administered a boosted protease inhibitor (lopinavir/ritonavir; atazanavir/ritonavir; or darunavir/ritonavir) instead of NNRTI from weeks 58 to 60 to reduce the risk of NNRTI resistance. Virological monitoring after ATI is performed up to two times per week during the first 6 weeks when rebound viremia is most likely to occur. ARV ATI is initiated in subjects who have plasma HIV RNA of less than 50 copies/ml for the previous 52 weeks. Subjects who have blips of more than 50 copies/ml but less than 200 copies/ml of plasma HIV RNA start ARV ATI provided that the most recent result is less than 50 copies/ml. During ARV ATI, the duration of viral control is determined and follow-up for subjects who resume therapy, i.e., fail to maintain viremic control, is performed.

ART is re-initiated in the subjects at the end of the trial at week 96, and if the subjects fail to maintain viremic control during ARV ATI (weeks 60 to 96). ART is re-initiated in subjects during ARV ATI with rebound viremia who have plasma HIV RNA levels above 1000 copies/ml on two consecutive determinations at least one week apart. The main endpoint for efficacy is the proportion of subjects with plasma HIV RNA of less than 50 copies/ml at 24 weeks after the initiation of ARV ATI.

It is understood that the examples and embodiments described herein are for illustrative purposes only, and that changes could be made to the embodiments described above without departing from the broad inventive concept thereof. It is understood, therefore, that this invention is not limited to the particular embodiments disclosed, but it is intended to cover modifications within the spirit and scope of the invention as defined by the appended claims.

SEQUENCE LISTING

SEQ ID NO: 1 (Mos1.Env) 685 aa:
MRVTGIRKNYQHLWRWGTMLLGILMICSAAGKLWVTVYYGVPVWKEATTTLFCASDAKAYDTEVHNVWAT

HACVPTDPNPQEVVLENVTENFNMWKNNMVEQMHEDIISLWDQSLKPCVKLTPLCVTLNCTDDVRNVTNN

ATNTNSSWGEPMEKGEIKNCSFNITTSIRNKVQKQYALFYKLDVVPIDNDSNNTNYRLISCNTSVITQAC

PKVSFEPIPIHYCAPAGFAILKCNDKKFNGTGPCTNVSTVQCTHGIRPVVSTQLLLNGSLAEEEVVIRSE

NFTNNAKTIMVQLNVSVEINCTRPNNNTRKSIHIGPGRAFYTAGDIIGDIRQAHCNISRANWNNTLRQIV

EKLGKQFGNNKTIVFNHSSGGDPEIVMHSFNCGGEFFYCNSTKLFNSTWTWNNSTWNNTKRSNDTEEHIT

LPCRIKQIINMWQEVGKAMYAPPIRGQIRCSSNITGLLLTRDGGNDTSGTEIFRPGGGDMRDNWRSELYK

YKVVKIEPLGVAPTKAKRRVVQSEKSAVGIGAVFLGFLGAAGSTMGAASMTLTVQARLLLSGIVQQQNNL

LRAIEAQQHLLQLTVWGIKQLQARVLAVERYLKDQQLLGIWGCSGKLICTTTVPWNASWSNKSLDKIWNN

MTWMEWEREINNYTSLIYTLIEESQNQQEKNEQELLELDKWASLWNWFDISNWLW

SEQ ID NO: 2 (Mos2.Env) 684 aa:
MRVRGIQRNWPQWWIWGILGFWMIICRVMGNLWVTVYYGVPVWKEAKTTLFCASDAKAYEKEVHNVWAT

HACVPTDPNPQEMVLENVTENFNMWKNDMVDQMHEDIIRLWDQSLKPCVKLTPLCVTLECRNVRNVSSNG

TYNIIHNETYKEMKNCSFNATTVVEDRKQKVHALFYRLDIVPLDENNSSEKSSENSSEYYRLINCNTSAI

TQACPKVSFDPIPIHYCAPAGYAILKCNNKTFNGTGPCNNVSTVQCTHGIKPVVSTQLLLNGSLAEEEII

IRSENLTNNAKTIIVHLNETVNITCTRPNNNTRKSIRIGPGQTFYATGDIIGDIRQAHCNLSRDGWNKTL

QGVKKKLAEHFPNKTINFTSSSGGDLEITTHSFNCRGEFFYCNTSGLFNGTYMPNGTNSNSSSNITLPCR

IKQIINMWQEVGRAMYAPPIAGNITCRSNITGLLLTRDGGSNNGVPNDTETFRPGGGDMRNNWRSELYKY

KVVEVKPLGVAPTEAKRRVVESEKSAVGIGAVFLGILGAAGSTMGAASITLTVQARQLLSGIVQQQSNLL

SEQUENCE LISTING

```
RAIEAQQHMLQLTVWGIKQLQTRVLAIERYLQDQQLLGLWGCSGKLICTTAVPWNTSWSNKSQTDIWDNM

TWMQWDKEIGNYTGEIYRLLEESQNQQEKNEKDLLALDSWKNLWNWFDITNWLW

SEQ ID NO: 3 (Mos1.Gag-Pol) 1350 aa:
MGARASVLSGGELDRWEKIRLRPGGKKKYRLKHIVWASRELERFAVNPGLLETSEGCRQILGQLQPSLQT

GSEELRSLYNTVATLYCVHQRIEIKDTKEALEKIEEEQNKSKKKAQQAAADTGNSSQVSQNYPIVQNIQG

QMVHQAISPRTLNAWVKVVEEKAFSPEVIPMFSALSEGATPQDLNTMLNTVGGHQAAMQMLKETINEEAA

EWDRVHPVHAGPIAPGQMREPRGSDIAGTTSTLQEQIGWMTNNPPIPVGEIYKRWIILGLNKIVRMYSPV

SILDIRQGPKEPFRDYVDRFYKTLRAEQASQDVKNWMTETLLVQNANPDCKTILKALGPAATLEEMMTAC

QGVGGPGHKARVLAEAMSQVTNSATIMMQRGNFRNQRKTVKCFNCGKEGHIAKNCRAPRKKGCWKCGKEG

HQMKDCTERQANFLGKIWPSNKGRPGNFLQNRPRPTAPPEESFRFGEETTTPSQKQEPIDKEMYPLASLK

SLFGNDPSSQMAPISPIETVPVKLKPGMDGPRVKQWPLTEEKIKALTAICEEMEKEGKITKIGPENPYNT

PVFAIKKKDSTKWRKLVDFRELNKRTQDFWEVQLGIPHPAGLKKKKSVTVLAVGDAYFSVPLDEGFRKYT

AFTIPSTNNETPGIRYQYNVLPQGWKGSPAIFQCSMTRILEPFRAKNPEIVIYQYMAALYVGSDLEIGQH

RAKIEELREHLLKWGFTTPDKKHQKEPPFLWMGYELHPDKWTVQPIQLPEKDSWTVNDIQKLVGKLNWAS

QIYPGIKVRQLCKLLRGAKALTDIVPLTEEAELELAENREILKEPVHGVYYDPSKDLIAEIQKQGHDQWT

YQIYQEPFKNLKTGKYAKMRTAHTNDVKQLTEAVQKIAMESIVIWGKTPKFRLPIQKETWETWWTDYWQA

TWIPEWEFVNTPPLVKLWYQLEKDPIAGVETFYVAGAANRETKLGKAGYVTDRGRQKIVSLTETTNQKTA

LQAIYLALQDSGSEVNIVTASQYALGIIQAQPDKSESELVNQIIEQLIKKERVYLSWVPAHKGIGGNEQV

DKLVSSGIRKVLFLDGIDKAQEEHEKYHSNWRAMASDFNLPPVVAKEIVASCDQCQLKGEAMHGQVDCSP

GIWQLACTHLEGKIILVAVHVASGYIEAEVIPAETGQETAYFILKLAGRWPVKVIHTANGSNFTSAAVKA

ACWWAGIQQEFGIPYNPQSQGVVASMNKELKKIIGQVRDQAEHLKTAVQMAVFIHNFKRKGGIGGYSAGE

RIIDIIATDIQTKELQKQIIKIQNFRVYYRDSRDPIWKGPAKLLWKGEGAVVIQDNSDIKVVPRRKVKII

KDYGKQMAGADCVAGRQDED

SEQ ID NO: 4 (Mos2.Gag-Pol) 1341 aa:
MGARASILRGGKLDKWEKIRLRPGGKKHYMLKHLVWASRELERFALNPGLLETSEGCKQIIKQLQPALQT

GTEELRSLFNTVATLYCVHAEIEVRDTKEALDKIEEEQNKSQQKTQQAKEADGKVSQNYPIVQNLQGQMV

HQPISPRTLNAWVKVIEEKAFSPEVIPMFTALSEGATPQDLNTMLNTVGGHQAAMAMLKDTINEEAAEWD

RLHPVHAGPVAPGQMREPRGSDIAGTTSNLQEQIAWMTSNPPIPVGDIYKRWIILGLNKIVRMYSPTSIL

DIKQGPKEPFRDYVDRFFKTLRAEQATQDVKNWMTDTLLVQNANPDCKTILRALGPGATLEEMMTACQGV

GGPSHKARVLAEAMSQTNSTILMQRSNFKGSKRIVKCFNCGKEGHIARNCRAPRKKGCWKCGKEGHQMKD

CTERQANFLGKIWPSHKGRPGNFLQSRPEPTAPPAESFRFEETTPAPKQEPKDREPLTSLRSLFGSDPLS

QMAPISPIETVPVKLKPGMDGPKVKQWPLTEEKIKALVEICTEMEKEGKISKIGPENPYNTPIFAIKKKD

STKWRKLVDFRELNKRTQDFWEVQLGIPHPAGLKKKKSVTVLAVGDAYFSVPLDEDFRKYTAFTIPSINN

ETPGIRYQYNVLPQGWKGSPAIFQSSMTKILEPFRKQNPDIVIYQYMAALYVGSDLEIGQHRTKIEELRQ

HLLRWGFTTPDKKHQKEPPFLWMGYELHPDKWTVQPIVLPEKDSWTVNDIQKLVGKLNWASQIYAGIKVK

QLCKLLRGTKALTEVVPLTEEAELELAENREILKEPVHGVYYDPSKDLIAEIQKQGQGQWTYQIYQEPFK

NLKTGKYARMRGAHTNDVKQLTEAVQKIATESIVIWGKTPKFKLPIQKETWEAWWTEYWQATWIPEWEFV

NTPPLVKLWYQLEKEPIVGAETFYVAGAANRETKLGKAGYVTDRGRQKVVSLTDTTNQKTALQAIHLALQ

DSGLEVNIVTASQYALGIIQAQPDKSESELVSQIIEQLIKKEKVYLAWVPAHKGIGGNEQVDKLVSRGIR
```

KVLFLDGIDKAQEEHEKYHSNWRAMASEFNLPPIVAKEIVASCDKCQLKGEAIHGQVDCSPGIWQLACTH

LEGKVILVAVHVASGYIEAEVIPAETGQETAYFLLKLAGRWPVKTIHTANGSNFTSATVKAACWWAGIKQ

EFGIPYNPQSQGVVASINKELKKIIGQVRDQAEHLKTAVQMAVFIHNFKRKGGIGEYSAGERIVDIIASD

IQTKELQKQITKIQNFRVYYRDSRDPLWKGPAKLLWKGEGAVVIQDNSDIKVVPRRKAKIIRDYGKQMAG

DDCVASRQDED

SEQ ID NO: 5 (Mos1.Env DNA)
ATGCGGGTGACCGGCATCCGGAAGAACTACCAGCACCTGTGGCGGTGGGGCACCATGCTGCTGGGCATCC

TGATGATTTGCTCTGCCGCCGGAAAGCTGTGGGTGACCGTGTACTACGGCGTGCCCGTGTGGAAAGAGGC

CACCACCACCCTGTTCTGCGCCAGCGACGCCAAGGCCTACGACACCGAGGTGCACAACGTGTGGGCCACC

CACGCCTGCGTGCCCACCGACCCCAACCCCCAGGAAGTGGTCCTGGAAAACGTGACCGAGAACTTCAACA

TGTGGAAGAACAACATGGTGGAGCAGATGCACGAGGACATCATCAGCCTGTGGGACCAGAGCCTGAAGCC

CTGCGTGAAGCTGACCCCCCTGTGCGTGACCCTGAACTGCACCGACGACGTGCGGAACGTGACCAACAAC

GCCACCAACACCAACAGCAGCTGGGGCGAGCCTATGGAAAAGGGCGAGATCAAGAACTGCAGCTTCAACA

TCACCACCTCCATCCGGAACAAGGTGCAGAAGCAGTACGCCCTGTTCTACAAGCTGGACGTGGTGCCCAT

CGACAACGACAGCAACAACACCAACTACCGGCTGATCAGCTGCAACACCAGCGTGATCACCCAGGCCTGC

CCCAAGGTGTCCTTCGAGCCCATCCCCATCCACTACTGCGCCCCTGCCGGCTTCGCCATCCTGAAGTGCA

ACGACAAGAAGTTCAACGGCACCGGCCCTGCACCAACGTGAGCACCGTGCAGTGCACCCACGGCATCCG

GCCCGTGGTGTCCACCCAGCTGCTGCTGAACGGCAGCCTGGCCGAGGAAGAGGTGGTGATCAGAAGCGAG

AATTTCACCAACAATGCCAAGACCATCATGGTGCAGCTGAACGTGAGCGTGGAGATCAACTGCACCCGGC

CCAACAACAACACCCGGAAGAGCATCCACATCGGCCCTGGCAGGGCCTTCTACACAGCCGGCGACATCAT

CGGCGACATCCGGCAGGCCCACTGCAACATCAGCCGGGCCAACTGGAACAACACCCTGCGGCAGATCGTG

GAGAAGCTGGGCAAGCAGTTCGGCAACAACAAGACCATCGTGTTCAACCACAGCAGCGGCGGAGACCCCG

AGATCGTGATGCACAGCTTCAACTGTGGCGGCGAGTTCTTCTACTGCAACAGCACCAAGCTGTTCAACAG

CACCTGGACCTGGAACAACTCCACCTGGAATAACACCAAGCGGAGCAACGACACCGAAGAGCACATCACC

CTGCCCTGCCGGATCAAGCAGATTATCAATATGTGGCAGGAGGTCGGCAAGGCCATGTACGCCCCTCCCA

TCCGGGCCAGATCCGGTGCAGCAGCAACATCACCGGCCTGCTGCTGACCCGGGACGGCGGCAACGATAC

CAGCGGCACCGAGATCTTCCGGCCTGGCGGCGGAGATATGCGGGACAACTGGCGGAGCGAGCTGTACAAG

TACAAGGTGGTGAAGATCGAGCCCCTGGGCGTGGCTCCCACCAAGGCCAAGCGGCGGGTGGTGCAGAGCG

AGAAGAGCGCCGTGGGCATCGGCGCCGTGTTTCTGGGCTTCCTGGGAGCCGCCGGAAGCACCATGGGAGC

CGCCAGCATGACCCTGACCGTGCAGGCCCGGCTGCTGCTGTCCGGCATCGTGCAGCAGCAGAACAACCTG

CTCCGGGCCATCGAGGCCCAGCAGCACCTGCTGCAGCTGACCGTGTGGGGCATCAAGCAGCTGCAGGCCA

GGGTGCTGGCCGTGGAGAGATACCTGAAGGATCAGCAGCTCCTGGGGATCTGGGCTGCAGCGGCAAGCT

GATCTGCACCACCACCGTGCCCTGGAACGCCAGCTGGTCCAACAAGAGCCTGGACAAGATCTGGAACAAT

ATGACCTGGATGGAATGGGAGCGCGAGATCAACAATTACACCAGCCTGATCTACACCCTGATCGAGGAAA

GCCAGAACCAGCAGGAAAAGAACGAGCAGGAACTGCTGGAACTGGACAAGTGGGCCAGCCTGTGGAACTG

GTTCGACATCAGCAACTGGCTGTGG

SEQ ID NO: 6 (Mos2.Env DNA)
ATGAGAGTGCGGGGCATCCAGCGGAACTGGCCCCAGTGGTGGATCTGGGCATCCTGGGCTTTTGGATGA

TCATCATCTGCCGGGTGATGGGCAACCTGTGGGTGACCGTGTACTACGGCGTGCCCGTGTGGAAAGAGGC

CAAGACCACCCTGTTCTGCGCCAGCGACGCCAAGGCCTACGAGAAAGAGGTGCACAACGTGTGGGCCACC

CACGCCTGCGTGCCCACCGACCCCAACCCCCAGGAAATGGTCCTGGAAAACGTGACCGAGAACTTCAACA

TGTGGAAGAACGACATGGTGGACCAGATGCACGAGGACATCATCCGGCTGTGGGACCAGAGCCTGAAGCC

CTGCGTGAAGCTGACCCCCCTGTGCGTGACCCTGGAATGCCGGAACGTGAGAAACGTGAGCAGCAACGGC

ACCTACAACATCATCCACAACGAGACCTACAAAGAGATGAAGAACTGCAGCTTCAACGCCACCACCGTGG

TGGAGGACCGGAAGCAGAAGGTGCACGCCCTGTTCTACCGGCTGGACATCGTGCCCCTGGACGAGAACAA

CAGCAGCGAGAAGTCCAGCGAGAACAGCTCCGAGTACTACCGGCTGATCAACTGCAACACCAGCGCCATC

ACCCAGGCCTGCCCCAAGGTGTCCTTCGACCCCATCCCCATCCACTACTGCGCCCCTGCCGGCTACGCCA

TCCTGAAGTGCAACAACAAGACCTTCAACGGCACCGGCCCCTGCAACAACGTGAGCACCGTGCAGTGCAC

CCACGGCATCAAGCCCGTGGTGTCCACCCAGCTGCTGCTGAACGGCAGCCTGGCCGAGGAAGAGATCATC

ATCCGGTCCGAGAACCTGACCAACAACGCCAAGACCATCATCGTGCACCTGAATGAGACCGTGAACATCA

CCTGCACCCGGCCCAACAACAACACCCGGAAGAGCATCCGGATCGGCCCTGGCCAGACCTTTTACGCCAC

CGGCGACATCATCGGCGACATCCGGCAGGCCCACTGCAACCTGAGCCGGGACGGCTGGAACAAGACCCTG

CAGGGCGTGAAGAAGAAGCTGGCCGAGCACTTCCCCAATAAGACCATCAACTTCACCCAGCAGCAGCGGCG

GAGACCTGGAAATCACCACCCACAGCTTCAACTGCAGGGGCGAGTTCTTCTACTGCAATACCTCCGGCCT

GTTCAATGGCACCTACATGCCCAACGGCACCAACAGCAACAGCAGCAGCAACATCACCCTGCCCTGCCGG

ATCAAGCAGATCATCAATATGTGGCAGGAGGTCGGCAGGGCCATGTACGCCCCTCCCATCGCCGGCAATA

TCACCTGCCGGTCCAACATCACCGGCCTGCTGCTGACCAGGGACGGCGGCAGCAACAACGGCGTGCCTAA

CGACACCGAGACCTTCCGGCCTGGCGGCGGAGATATGCGGAACAACTGGCGGAGCGAGCTGTACAAGTAC

AAGGTGGTGGAGGTGAAGCCCCTGGGCGTGGCTCCTACCGAGGCCAAGCGGCGGGTGGTGGAGAGCGAGA

AGAGCGCCGTGGGCATCGGCGCCGTGTTTCTGGGCATTCTGGGAGCCGCCGGAAGCACCATGGGAGCCGC

CAGCATCACCCTGACCGTGCAGGCCCGGCAGCTGCTGTCCGGCATCGTGCAGCAGCAGAGCAACCTGCTG

AGAGCCATCGAGGCCCAGCAGCACATGCTGCAGCTGACCGTGTGGGGCATCAAGCAGCTGCAGACCCGGG

TGCTGGCCATCGAGAGATACCTGCAGGATCAGCAGCTCCTGGGCCTGTGGGGCTGCAGCGGCAAGCTGAT

CTGCACCACCGCCGTGCCCTGGAACACCAGCTGGTCCAACAAGAGCCAGACCGACATCTGGGACAACATG

ACCTGGATGCAGTGGGACAAAGAGATCGGCAACTACACCGGCGAGATCTACAGGCTGCTGGAAGAGAGCC

AGAACCAGCAGGAAAAGAACGAGAAGGACCTGCTGGCCCTGGACAGCTGGAAGAACCTGTGGAACTGGTT

CGACATCACCAACTGGCTGTGG

SEQ ID NO: 7 (Mos1.Gag-Pol DNA)
ATGGGAGCCAGAGCCAGCGTGCTGTCCGGAGGGGAGCTGGACCGCTGGGAGAAGATCAGGCTGAGGCCTG

GAGGGAAGAAGAAGTACAGGCTGAAGCACATCGTGTGGGCCAGCAGAGAGCTGGAACGGTTTGCCGTGAA

CCCTGGCCTGCTGGAAACCAGCGAGGGCTGTAGGCAGATTCTGGGACAGCTGCAGCCCAGCCTGCAGACA

GGCAGCGAGGAACTGCGGAGCCTGTACAACACCGTGGCCACCCTGTACTGCGTGCACCAGCGGATCGAGA

TCAAGGACACCAAAGAAGCCCTGGAAAAGATCGAGGAAGAGCAGAACAAGAGCAAGAAGAAAGCCCAGCA

GGCTGCCGCTGACACAGGCAACAGCAGCCAGGTGTCCCAGAACTACCCCATCGTGCAGAACATCCAGGGA

CAGATGGTGCACCAGGCCATCAGCCCTCGGACCCTGAACGCCTGGGTGAAGGTGGTGGAGGAAAAGGCCT

TCAGCCCTGAGGTGATCCCCATGTTCTCTGCCCTGAGCGAGGGAGCCACACCCCAGGACCTGAACACCAT

GCTGAACACCGTGGGAGGGCACCAGGCTGCCATGCAGATGCTGAAAGAGACAATCAACGAGGAAGCTGCC

GAGTGGGACAGGGTCCACCCAGTGCACGCTGGACCTATCGCTCCTGGCCAGATGAGAGAGCCCAGAGGCA

GCGATATTGCTGGCACCACCTCCACACTGCAGGAACAGATCGGCTGGATGACCAACAACCCTCCCATCCC

-continued

SEQUENCE LISTING

```
TGTGGGAGAGATCTACAAGCGGTGGATCATTCTGGGACTGAACAAGATCGTGCGGATGTACAGCCCTGTG

AGCATCCTGGACATCAGGCAGGGACCCAAAGAGCCCTTCAGGGACTACGTGGACCGGTTCTACAAGACCC

TGAGAGCCGAGCAGGCCAGCCAGGACGTGAAGAACTGGATGACCGAGACACTGCTGGTGCAGAACGCCAA

CCCTGACTGCAAGACCATCCTGAAAGCCCTGGGACCTGCTGCCACCCTGGAAGAGATGATGACAGCCTGC

CAGGGAGTGGGAGGACCTGGCCACAAGGCCAGGGTGCTGGCCGAGGCCATGAGCCAGGTGACCAACTCTG

CCACCATCATGATGCAGAGAGGCAACTTCCGGAACCAGAGAAAGACCGTGAAGTGCTTCAACTGTGGCAA

AGAGGGACACATTGCCAAGAACTGCAGGGCTCCCAGGAAGAAAGGCTGCTGGAAGTGCGGAAAAGAAGGC

CACCAGATGAAGGACTGCACCGAGAGGCAGGCCAACTTCCTGGGCAAGATCTGGCCTAGCAACAAGGGCA

GGCCTGGCAACTTCCTGCAGAACAGACCCGAGCCCACCGCTCCTCCCGAGGAAAGCTTCCGGTTTGGCGA

GGAAACCACCACCCCTAGCCAGAAGCAGGAACCCATCGACAAAGAGATGTACCCTCTGGCCAGCCTGAAG

AGCCTGTTCGGCAACGACCCCAGCAGCCAGATGGCTCCCATCAGCCCAATCGAGACAGTGCCTGTGAAGC

TGAAGCCTGGCATGGACGGACCCAGGGTGAAGCAGTGGCCTCTGACCGAGGAAAAGATCAAAGCCCTGAC

AGCCATCTGCGAGGAAATGGAAAAGAGGGCAAGATCACCAAGATCGGACCCGAGAACCCCTACAACACC

CCTGTGTTCGCCATCAAGAAGAAAGACAGCACCAAGTGGAGGAAACTGGTGGACTTCAGAGAGCTGAACA

AGCGGACCCAGGACTTCTGGGAGGTGCAGCTGGGCATCCCTCACCCTGCTGGCCTGAAGAAAAAGAAAAG

CGTGACCGTGCTGGCTGTGGGAGATGCCTACTTCAGCGTGCCTCTGGACGAGGGCTTCCGGAAGTACACA

GCCTTCACCATCCCCAGCACCAACAACGAGACACCTGGCATCAGATACCAGTACAACGTGCTGCCTCAGG

GCTGGAAAGGCAGCCCTGCCATCTTCCAGTGCAGCATGACCAGAATCCTGGAACCCTTCAGAGCCAAGAA

CCCTGAGATCGTGATCTACCAGTATATGGCTGCCCTCTACGTGGGCAGCGACCTGGAAATCGGACAGCAC

AGAGCCAAAATCGAAGAACTCCGCGAGCACCTGCTGAAGTGGGGATTCACCACCCCTGACAAGAAGCACC

AGAAAGAGCCTCCCTTCCTGTGGATGGGCTACGAGCTGCACCCTGACAAGTGGACCGTGCAGCCCATCCA

GCTGCCAGAGAAGGACTCCTGGACCGTGAACGACATCCAGAAACTGGTCGGCAAGCTGAACTGGGCCAGC

CAGATCTACCCTGGCATCAAAGTCAGACAGCTGTGTAAGCTGCTGAGGGGAGCCAAAGCACTGACCGACA

TCGTGCCTCTGACAGAAGAAGCCGAGCTGGAACTGGCCGAGAACAGAGAGATCCTGAAAGAACCCGTGCA

CGGAGTGTACTACGACCCCTCCAAGGACCTGATTGCCGAGATCCAGAAACAGGGACACGACCAGTGGACC

TACCAGATCTATCAGGAACCTTTTCAAGAACCTGAAAACAGGCAAGTACGCCAAGATGCGGACAGCCCACA

CCAACGACGTGAAGCAGCTGACCGAAGCCGTGCAGAAAATCGCCATGGAAAGCATCGTGATCTGGGGAAA

GACACCCAAGTTCAGGCTGCCCATCCAGAAAGAGACATGGGAAACCTGGTGGACCGACTACTGGCAGGCC

ACCTGGATTCCCGAGTGGGAGTTCGTGAACACCCCACCCCTGGTGAAGCTGTGGTATCAGCTGGAAAAGG

ACCCTATCGCTGGCGTGGAGACATTCTACGTGGCTGGAGCTGCCAACAGAGAGACAAAGCTGGGCAAGGC

TGGCTACGTGACCGACAGAGGCAGACAGAAAATCGTGAGCCTGACCGAAACCACCAACCAGAAAACAGCC

CTGCAGGCCATCTATCTGGCACTGCAGGACAGCGGAAGCGAGGTGAACATCGTGACAGCCAGCCAGTATG

CCCTGGGCATCATCCAGGCCCAGCCTGACAAGAGCGAGAGCGAGCTGGTGAACCAGATCATCGAGCAGCT

GATCAAGAAGAACGGGTGTACCTGAGCTGGGTGCCAGCCCACAAGGGCATCGGAGGGAACGAGCAGGTG

GACAAGCTGGTGTCCAGCGGAATCCGGAAGGTGCTGTTCCTGGACGGCATCGATAAAGCCCAGGAAGAGC

ACGAGAAGTACCACAGCAATTGGAGAGCCATGGCCAGCGACTTCAACCTGCCTCCCGTGGTGGCCAAAGA

AATCGTGGCCAGCTGCGACCAGTGCCAGCTGAAAGGCGAGGCCATGCACGGACAGGTGGACTGCTCCCCT

GGCATCTGGCAGCTGGCATGCACCCACCTGGAAGGCAAGATCATTCTGGTGGCCGTGCACGTGGCCAGCG
```

```
GATACATCGAAGCCGAAGTGATCCCTGCCGAGACAGGGCAGGAAACAGCCTACTTCATCCTGAAGCTGGC

TGGCAGATGGCCTGTGAAGGTGATCCACACAGCCAACGGCAGCAACTTCACCTCTGCTGCCGTGAAGGCT

GCCTGTTGGTGGGCTGGCATTCAGCAGGAATTTGGCATCCCCTACAATCCCCAGTCTCAGGGAGTGGTGG

CCAGCATGAACAAAGAGCTGAAGAAGATCATCGGACAGGTCAGGGATCAGGCCGAGCACCTGAAAACTGC

CGTCCAGATGGCCGTGTTCATCCACAACTTCAAGCGGAAGGGAGGGATCGGAGGGTACTCTGCTGGCGAG

CGGATCATCGACATCATTGCCACCGATATCCAGACCAAAGAGCTGCAGAAACAGATCATCAAGATCCAGA

ACTTCAGGGTGTACTACAGGGACAGCAGGGACCCCATCTGGAAGGGACCTGCCAAGCTGCTGTGGAAAGG

CGAAGGAGCCGTCGTCATCCAGGACAACAGCGACATCAAGGTGGTGCCCAGACGGAAGGTGAAAATCATC

AAGGACTACGGCAAACAGATGGCTGGAGCCGACTGTGTCGCTGGCAGGCAGGACGAGGAC

SEQ ID NO: 8 (Mos2.Gag-Pol DNA)
ATGGGAGCCAGAGCCAGCATCCTGCGAGGAGGGAAGCTGGACAAGTGGGAGAAGATCAGGCTGAGGCCTG

GAGGGAAGAAACACTACATGCTGAAGCACCTGGTCTGGGCCAGCAGAGAGCTGGAACGGTTTGCCCTCAA

TCCTGGCCTGCTGGAAACCAGCGAGGGCTGCAAGCAGATCATCAAGCAGCTGCAGCCTGCCCTGCAGACA

GGCACCGAGGAACTGCGGAGCCTGTTCAACACCGTGGCCACCCTGTACTGCGTGCATGCCGAGATCGAAG

TGAGGGACACCAAAGAAGCCCTGGACAAGATCGAGGAAGAGCAGAACAAGAGCCAGCAGAAAACCCAGCA

GGCCAAAGAAGCCGACGGCAAGGTCTCCCAGAACTACCCCATCGTGCAGAACCTGCAGGGACAGATGGTG

CACCAGCCCATCAGCCCTCGGACACTGAATGCCTGGGTGAAGGTGATCGAGGAAAAGGCCTTCAGCCCTG

AGGTGATCCCCATGTTCACAGCCCTGAGCGAGGGAGCCACACCCCAGGACCTGAACACCATGCTGAACAC

CGTGGGAGGGCACCAGGCTGCCATGCAGATGCTGAAGGACACCATCAACGAGGAAGCTGCCGAGTGGGAC

AGGCTGCACCCTGTGCACGCTGGACCTGTGGCTCCTGGCCAGATGAGAGAGCCCAGAGGCAGCGATATTG

CTGGCACCACCTCCAATCTGCAGGAACAGATCGCCTGGATGACCAGCAACCCTCCCATCCCTGTGGGAGA

CATCTACAAGCGGTGGATCATCCTGGGACTGAACAAGATCGTGCGGATGTACAGCCCTACCTCCATCCTG

GACATCAAGCAGGGACCCAAAGAGCCTTTCAGGGACTACGTGGACCGGTTCTTCAAGACCCTGAGAGCCG

AGCAGGCCACCCAGGACGTGAAGAACTGGATGACCGACACCCTGCTGGTGCAGAACGCCAACCCTGACTG

CAAGACCATCCTGAGAGCCCTGGGACCTGGAGCCACCCTGGAAGAGATGATGACAGCCTGCCAGGGAGTG

GGAGGACCCTCTCACAAGGCTAGGGTGCTGGCCGAGGCCATGAGCCAGACCAACAGCACCATCCTGATGC

AGCGGAGCAACTTCAAGGGCAGCAAGCGGATCGTGAAGTGCTTCAACTGTGGCAAAGAGGGACACATTGC

CAGAAACTGTAGGGCACCCAGGAAGAAAGGCTGCTGGAAGTGCGGAAAAGAAGGCCACCAGATGAAGGAC

TGCACCGAGAGGCAGGCCAACTTCCTGGGCAAGATCTGGCCTAGCCACAAGGGCAGACCTGGCAACTTCC

TGCAGAGCAGACCCGAGCCCACCGCTCCTCCAGCCGAGAGCTTCCGGTTCGAGGAAACCACCCCTGCTCC

CAAGCAGGAACCTAAGGACAGAGAGCCTCTGACCAGCCTGAGAAGCCTGTTCGGCAGCGACCCTCTGAGC

CAGATGGCTCCCATCTCCCCTATCGAGACAGTGCCTGTGAAGCTGAAGCCTGGCATGGACGGACCCAAGG

TGAAACAGTGGCCTCTGACCGAGGAAAAGATCAAAGCCCTGGTGGAGATCTGTACCGAGATGGAAAAAGA

GGGCAAGATCAGCAAGATCGGACCCGAGAACCCCTACAACACCCCTATCTTCGCCATCAAGAAGAAAGAC

AGCACCAAGTGGAGGAAACTGGTGGACTTCAGAGAGCTGAACAAGCGGACCCAGGACTTCTGGGAGGTGC

AGCTGGGCATCCCTCACCCTGCTGGCCTGAAGAAAAAGAAAAGCGTGACCGTGCTGGCCGTGGGAGATGC

CTACTTCAGCGTGCCTCTGGACGAGGACTTCAGAAAGTACACAGCCTTCACCATCCCCAGCATCAACAAC

GAGACACCTGGCATCAGATACCAGTACAACGTGCTGCCTCAGGGATGGAAGGGCTCTCCTGCAATCTTCC

AGAGCAGCATGACCAAGATCCTGGAACCCTTCCGGAAGCAGAACCCTGACATCGTGATCTACCAGTACAT
```

SEQUENCE LISTING

```
GGCAGCCCTGTACGTCGGCAGCGACCTGGAAATCGGACAGCACCGGACCAAGATCGAAGAACTCAGGCAG
CACCTGCTGCGGTGGGGATTCACCACCCCTGACAAGAAGCACCAGAAAGAGCCTCCCTTCCTGTGGATGG
GCTACGAGCTGCACCCAGACAAGTGGACCGTGCAGCCCATCGTGCTGCCTGAGAAGGACTCCTGGACCGT
GAACGACATCCAGAAACTGGTCGGCAAGCTGAACTGGGCCAGCCAGATCTACGCTGGCATCAAAGTGAAG
CAGCTGTGTAAGCTCCTGAGAGGCACCAAAGCCCTGACCGAGGTGGTGCCACTGACAGAGGAAGCCGAGC
TGGAACTGGCCGAGAACAGAGAGATCCTGAAAGAACCCGTGCACGGAGTGTACTACGACCCCAGCAAGGA
CCTGATTGCCGAGATCCAGAAGCAGGGACAGGGACAGTGGACCTACCAGATCTACCAGGAACCCTTCAAG
AACCTGAAAACAGGCAAGTACGCCAGGATGAGGGGAGCCCACACCAACGACGTCAAACAGCTGACCGAAG
CCGTGCAGAAGATCGCCACCGAGAGCATCGTGATTTGGGGAAAGACACCCAAGTTCAAGCTGCCCATCCA
GAAAGAGACATGGGAGGCCTGGTGGACCGAGTACTGGCAGGCCACCTGGATTCCCGAGTGGGAGTTCGTG
AACACCCCACCCCTGGTGAAGCTGTGGTATCAGCTGGAAAAAGAACCCATCGTGGGAGCCGAGACATTCT
ACGTGGCTGGAGCTGCCAACAGAGAGACAAAGCTGGGCAAGGCTGGCTACGTGACCGACAGAGGCAGGCA
GAAAGTGGTGTCCCTGACCGATACCACCAACCAGAAAACAGCCCTGCAGGCCATCCACCTGGCTCTGCAG
GACTCTGGCCTGGAAGTGAACATCGTGACAGCCAGCCAGTATGCCCTGGGCATCATTCAGGCACAGCCTG
ACAAGAGCGAGAGCGAGCTGGTGTCTCAGATCATTGAGCAGCTGATCAAGAAAGAAAAGGTGTACCTGGC
CTGGGTGCCAGCCCACAAGGGGATCGGAGGGAACGAGCAGGTGGACAAGCTGGTGTCCAGGGGCATCCGG
AAGGTGCTGTTTCTGGACGGCATCGACAAAGCCCAGGAAGAGCACGAGAAGTACCACAGCAATTGGAGAG
CCATGGCCAGCGAGTTCAACCTGCCTCCCATCGTGGCCAAAGAAATCGTGGCCTCTTGCGACAAGTGCCA
GCTGAAAGGCGAGGCCATTCACGGACAGGTGGACTGCAGCCCAGGCATCTGGCAGCTGGCCTGCACCCAC
CTGGAAGGCAAGGTGATCCTGGTGGCCGTGCACGTGGCCTCTGGATACATCGAAGCCGAAGTGATCCCTG
CCGAGACAGGCCAGGAAACAGCCTACTTCCTGCTGAAGCTGGCTGGCAGGTGGCCTGTGAAAACCATCCA
CACAGCCAACGGCAGCAACTTCACCTCTGCCACCGTGAAGGCTGCCTGTTGGTGGGCTGGCATTAAGCAG
GAATTTGGCATCCCCTACAACCCTCAGTCTCAGGGAGTGGTGGCCTCCATCAACAAAGAGCTGAAGAAGA
TCATCGGACAGGTCAGGGATCAGGCCGAGCATCTGAAAACAGCCGTCCAGATGGCCGTGTTCATCCACAA
CTTCAAGCGGAAGGGAGGGATCGGAGAGTACTCTGCTGGCGAGAGGATCGTGGACATTATCGCCAGCGAT
ATCCAGACCAAAGAACTGCAGAAGCAGATCACAAAGATCCAGAACTTCAGGGTGTACTACAGGGACAGCA
GAGATCCCCTGTGGAAGGGACCTGCCAAGCTGCTGTGGAAAGGCGAAGGAGCCGTCGTCATCCAGGACAA
CAGCGACATCAAGGTGGTGCCCAGACGGAAGGCCAAGATCATCAGAGACTACGGCAAACAGATGGCTGGC
GACGACTGCGTCGCCTCTAGGCAGGACGAGGAC
```

REFERENCES

1. Chen et al. *Nat Med.* (2001) 7(11), 1225-31
2. UNAIDS Report on the Global AIDS Epidemic 2013
3. Carcelain et al. Immunol Rev. (2013) 254(1), 355-71
4. Katlama Lancet. (2013) 381(9883), 2109-17
5. Gianella et al. Antiviral therapy. (2011) 16(4), 535-45
6. Goujard et al. (2012) Antiviral therapy. 17(6), 1001-9
7. Hamlyn et al. (2012) PloS one. 7(8), e43754
8. Lodi et al. (2012) Archives of internal medicine. 172(16), 1252-5
9. Saez-Cirion et al. (2013) PLoS pathogens 9(3), e1003211
10. US20120076812
11. Barouch et al., Nat Med 2010, 16:319-323
12. Barouch et al., Cell 155:1-9, 2013
13. Fischer et al, Nat Med, 2007. 13(1): p. 100-6
14. Havenga, et al., 2006, J Gen Virol 87: 2135-43
15. WO 03/104467
16. WO 2007/104792
17. Abbink et al., (2007) Virol 81(9): 4654-63
18. Mayr et al. (1975) Infection 3, 6-14
19. Mayr, A. & Danner, K. (1978), Dev. Biol. Stand. 41: 225-234
20. Stickl (1974), Prev. Med. 3: 97-101
21. Stickl and Hochstein-Mintzel (1971), Munch. Med. Wochenschr. 113: 1149-1153
22. Mayr et al. (1978), Zentralbl. Bacteriol. (B) 167:375-390
23. Blanchard et al. (1998), J. Gen. Virol. 79:1159-116779
24. Carroll & Moss (1997), Virology 238:198-211

25. U.S. Pat. No. 5,185,146; 81
26. WO 02/42480 (US 2003/0206926)
27. WO 03/048184 (US 2006/0159699)
28. U.S. Pat. No. 6,761,893
29. US20110159036
30. U.S. Pat. No. 8,197,825
31. WO 2011/092029
32. Williams et al. (2014) Elife 3, e03821

---

What is claimed is:

1. A method of inducing an immune response against a human immunodeficiency virus (HIV) in an HIV-infected human subject undergoing antiretroviral therapy (ART), the method comprising:
   (i) administering to the human subject a primer vaccine comprising an immunogenically effective amount of one or more adenovirus 26 (Ad26) vectors encoding one or more mosaic HIV gag, pol and/or env antigens and a pharmaceutically acceptable carrier; and
   (ii) administering to the human subject a booster vaccine comprising an immunogenically effective amount of one or more modified vaccinia ankara (MVA) vectors encoding one or more mosaic HIV gag, pol and/or env antigens and a pharmaceutically acceptable carrier.

2. The method of claim 1, wherein the booster vaccine is administered about 22-26 weeks after the primer vaccine is initially administered.

3. The method according to claim 1, wherein the primer vaccine comprises Ad26 vectors encoding three mosaic HIV antigens having the amino acid sequences of SEQ ID NO: 1, SEQ ID NO: 3, and SEQ ID NO: 4; and the booster vaccine comprises MVA vectors encoding four mosaic HIV antigens having the amino acid sequences of SEQ ID NO: 1, SEQ ID NO: 2, SEQ ID NO: 3, and SEQ ID NO: 4.

4. The method according to claim 3, wherein the immunogenically effective amount of the Ad26 vectors encoding mosaic HIV antigens of SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen of SEQ ID NO: 4.

5. The method according to claim 4, wherein the first, second, and third Ad26 vectors are administered at a total dose of about $5\times10^{10}$ viral particles (vp).

6. The method according to claim 3, wherein the immunogenically effective amount of the MVA vectors encoding mosaic HIV antigens of SEQ ID NOs: 1, 2, 3, and 4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4.

7. The method according to claim 6, wherein the first and second MVA vectors are administered at a total dose of about $1\times10^8$ plaque forming units (pfu).

8. The method according to claim 1, further comprising re-administering the primer vaccine at about 10-14 weeks after the primer vaccine is initially administered; and re-administering the booster vaccine at about 46 to 50 weeks after the primer vaccine is initially administered.

9. The method according to claim 8, wherein the primer vaccine is re-administered at about 12 weeks after the primer vaccine is initially administered; the booster vaccine is first administered at about 24 weeks after the primer vaccine is initially administered; and the booster vaccine is re-administered at about 48 weeks after the primer vaccine is initially administered.

10. The method according to claim 1, wherein the human subject initiated ART during acute HIV infection.

11. The method according to claim 1, wherein the ART is discontinued at about 10-14 weeks after the last booster vaccine is administered.

12. A method of inducing an immune response against a human immunodeficiency virus (HIV) in an HIV-infected human subject undergoing antiretroviral therapy (ART), the method comprising:
   (i) administering to the human subject a primer vaccine comprising an immunogenically effective amount of one or more adenovirus 26 (Ad26) vectors encoding one or more mosaic HIV antigens comprising the amino acid sequences selected from the group consisting of SEQ ID NOs: 1, 3, and 4 and a pharmaceutically acceptable carrier; and
   (ii) administering to the human subject a booster composition comprising an immunogenically effective amount of one or more MVA vectors encoding one or more mosaic HIV antigens comprising the amino acid sequences selected from the group consisting of SEQ ID NOs: 1-4 and a pharmaceutically acceptable carrier,
   wherein the primer vaccine is re-administered at about 10-14 weeks after the primer vaccine is initially administered; the booster vaccine is first administered at about 22-26 weeks after the primer vaccine is initially administered; and the booster vaccine is re-administered at about 46-50 weeks after primer vaccine is initially administered; and
   wherein the human subject initiated ART during acute HIV infection.

13. The method according to claim 12, wherein the immunogenically effective amount of the Ad26 vectors encoding one or more mosaic HIV antigens of SEQ ID NOs: 1, 3, and 4 consists of three Ad26 vectors of which a first Ad26 vector encodes mosaic HIV antigen of SEQ ID NO: 1, a second Ad26 vector encodes mosaic HIV antigen of SEQ ID NO: 3, and a third Ad26 vector encodes mosaic HIV antigen of SEQ ID NO: 4.

14. The method according to claim 13, wherein the first, second, and third Ad26 vectors are administered at a total dose of about $5\times10^{10}$ vp.

15. The method according to claim 12, wherein the primer vaccine is re-administered at about 12 weeks after the primer vaccine is initially administered, the booster vaccine is first administered at about 24 weeks after the primer vaccine is initially administered, and the booster vaccine is re-administered at about 48 weeks after the primer vaccine is initially administered.

16. The method according to claim 12, wherein the ART is discontinued at about 10-14 weeks after the last booster vaccine is administered.

17. The method according to claim 1, wherein a human subject to which the primer vaccine and the booster vaccine has been administered, discontinues ART and maintains viral suppression for at least 24 weeks after discontinuing ART.

18. The method according to claim 12, wherein a human subject to which the primer vaccine and the booster vaccine has been administered, discontinues ART and maintains viral suppression for at least 24 weeks after discontinuing ART.

19. The method according to claim 13, wherein the immunogenically effective amount of the MVA vectors encoding one or more mosaic HIV antigens of SEQ ID NOs: 1-4 consists of two MVA vectors of which a first MVA vector encodes mosaic HIV antigens of SEQ ID NOs: 1 and 3, and a second MVA vector encodes mosaic HIV antigens of SEQ ID NOs: 2 and 4.

20. The method according to claim 19, wherein the first, second, and third Ad26 vectors are administered at a total dose of about $5 \times 10^{10}$ vp, and the first and second MVA vectors are administered at a total dose of about $1 \times 10^8$ pfu.

* * * * *

UNITED STATES PATENT AND TRADEMARK OFFICE
CERTIFICATE OF CORRECTION

PATENT NO. : 10,307,477 B2
APPLICATION NO. : 15/693650
DATED : June 4, 2019
INVENTOR(S) : Frank Tomaka et al.

Page 1 of 1

It is certified that error appears in the above-identified patent and that said Letters Patent is hereby corrected as shown below:

In the Specification

The following paragraph should be inserted at Column 1, Line 15, as follows:
--STATEMENT REGARDING FEDERALLY SPONSORED RESEARCH OR DEVELOPMENT
This invention was made with government support under W81XWH-11-2-0174 awarded by the United States Army Medical Research and Materiel Command. The government has certain rights in this invention.--

Signed and Sealed this
Twentieth Day of August, 2019

Andrei Iancu
*Director of the United States Patent and Trademark Office*